(12) United States Patent
Flikweert et al.

(10) Patent No.: US 11,149,085 B2
(45) Date of Patent: Oct. 19, 2021

(54) MANUFACTURING METHODS TO CONTROL C-TERMINAL LYSINE, GALACTOSE AND SIALIC ACID CONTENT IN RECOMBINANT PROTEINS

(71) Applicants: Janssen Biotech, Inc., Horsham, PA (US); Janssen Biologies B.V., Leiden (NL)

(72) Inventors: Marcel Flikweert, Leiden (NL); Charles Goochee, Malvern, PA (US); Francis C. Maslanka, Malvern, PA (US); Franciscus Johannes Ignatius Nagel, Leiden (NL); James R. Ryland, Malvern, PA (US); Eugene Schaefer, Malvern, PA (US)

(73) Assignees: JANSSEN BIOTECH, INC., Horsham, PA (US); JANSSEN BIOLOGICS B.V., Leiden (NL)

( * ) Notice: Subject to any disclaimer, the term of this patent is extended or adjusted under 35 U.S.C. 154(b) by 372 days.

(21) Appl. No.: 14/757,691

(22) Filed: Dec. 23, 2015

(65) Prior Publication Data
US 2016/0237149 A1 Aug. 18, 2016

Related U.S. Application Data

(63) Continuation of application No. 14/207,915, filed on Mar. 13, 2014, now abandoned.

(60) Provisional application No. 61/791,094, filed on Mar. 15, 2013.

(51) Int. Cl.
*C07K 16/24* (2006.01)
*C07K 16/00* (2006.01)

(52) U.S. Cl.
CPC ............ *C07K 16/241* (2013.01); *C07K 16/00* (2013.01); *C07K 2317/14* (2013.01); *C07K 2317/21* (2013.01); *C07K 2317/24* (2013.01); *C07K 2317/40* (2013.01); *C07K 2317/41* (2013.01); *C07K 2317/52* (2013.01); *C07K 2317/54* (2013.01); *C07K 2317/55* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,376,110 A | 3/1983 | David et al. |
| 5,231,024 A | 7/1993 | Moeller et al. |
| 5,919,452 A | 7/1999 | Le et al. |
| 6,790,444 B2 | 9/2004 | Le et al. |
| 7,070,775 B2 | 7/2006 | Le et al. |
| 7,169,388 B2 | 1/2007 | Le et al. |
| 7,250,165 B2 | 7/2007 | Heavner et al. |
| 7,252,823 B2 | 8/2007 | Le et al. |
| 2004/0185047 A1 | 9/2004 | Giles-Komar et al. |
| 2012/0259095 A1 | 10/2012 | Beliard et al. |
| 2013/0280274 A1 | 10/2013 | Subramanian et al. |
| 2014/0120583 A1 | 5/2014 | Prentice |
| 2014/0142286 A1 | 5/2014 | Prentice |
| 2016/0046708 A1 | 2/2016 | Subramanian et al. |

FOREIGN PATENT DOCUMENTS

| | | |
|---|---|---|
| CA | 2 895 402 A1 | 9/2014 |
| EP | 0 218 868 A2 | 4/1987 |
| EP | 0 288 088 B1 | 3/1994 |
| JP | 2011-516080 A | 5/2011 |
| JP | 2012-087144 A | 5/2012 |
| WO | WO 91/02078 | 2/1991 |
| WO | 92/16553 A1 | 10/1992 |
| WO | WO 2004/085474 A2 | 10/2004 |
| WO | WO 2006/108455 A1 | 10/2006 |
| WO | WO 2009/126564 A1 | 10/2009 |
| WO | WO 2012/147053 A1 | 11/2012 |
| WO | WO 2013/009648 A2 | 1/2013 |
| WO | 2013/158273 A1 | 10/2013 |
| WO | WO 2014/143184 A1 | 9/2014 |

OTHER PUBLICATIONS

Vajdos et al. (J Mol Biol. Jul. 5, 2002;320(2):415-428 ) (Year: 2002).*
Brown et al. (J Immunol. May 1996;156(9):3285-91) (Year: 1996).*
Abbott, W.M., et al., "Current Approaches to Fine Mapping of Antigen-Antibody Interactions", *Immunology*, 142(4):526-535 (2014).
Cai, B., et al., "C-Terminal Lysine Processing of Human Immunoglobulin G2 Heavy Chain in vivo", *Biotecnol, Bioeng.*, 108: 404-412 (2011).
Cabilly,S., et al., "Generation of Antibody Activity from Immunoglobulin Polypeptide Chains Produced in *Escherichia coli*", *Proc. Natl. Acad. Sci.*, 81:3273-3277 (1984).
Morrison, S. L., et al., "Chimeric Human Antibody Molecules: Mouse Antigen-Binding Domains with Human Constant Region Domains", *Proc Natl. Acad. Sci.*, 81:6851-6855 (1984).
Neuberger, M.S., et al., "A Hapten-Specific Chimeric IgE Antibody with Human Physiological Effector Function", *Nature*, 314:268-270 (1985).
Köhler, G. and Milstein, C., "Continuous Cultures of Fused Cells Secreting Antibody of Predefined Specificity", *Nature*, 256:495-497 (1975).

(Continued)

*Primary Examiner* — Brian Gangle
*Assistant Examiner* — Andrea K Mccollum
(74) *Attorney, Agent, or Firm* — Hamilton, Brook, Smith & Reynolds, P.C.

(57) ABSTRACT

Provided herein is a method for producing an antibody, such as an anti-TNFα antibody (e.g., infliximab) having a C-terminal lysine content of about 20% to about 70%, and a sialic acid content of about 1% to about 20%, comprising culturing a zinc-responsive host cell transfected with DNA encoding the antibody in a culture medium comprising at least 0.5 µM zinc; and controlling the concentration of zinc in the culture medium, thereby producing the antibody.

33 Claims, 47 Drawing Sheets

Specification includes a Sequence Listing.

(56) References Cited

OTHER PUBLICATIONS

Wahl, R.L., et al., "Improved Radioimaging and Tumor Localization with Monoclonal F(ab')$_2$", *J. Nucl. Med.*, 24:316-325 (1983).
Müller, R., "Determination of Affinity and Specificity of Anti-Hapten Antibodies by Competitive Radioimmunoassay", *Meth. Enzymol*, 92:589-601(1983).
Smith, R.A. and Baglioni, C., "The Active Form of Tumor Necrosis Factor is a Trimer", *J. Biol., Chem.*, 262:6951-6954 (1987).
Kriegler, M., et al., "A Novel Form of TNF/Cachectin is a Cell Surface Cytotoxic Transmembrane Protein: Ramifications for the Complex Physiology of TNF", *Cell*, 53:45-53 (1988).
Beutler, B. and Ceramin, A., "Cachectin and Tumour Necrosis Factor as Two Sides of the Same Biological Coin", *Nature*, 320:584 (1986).
Old, L. J., "Tumour Necrosis Factor (TNF)", *Science*, 230:630 (1986).
Le, J. and Vilcek, J., "Tumor Necrosis Factor and Interleukin 1: Cytokines with Multiple Overlapping Biological Activities", *Lab Inves.*, 56(3):234-248 (1987).
Pennica, D., et al., "Human Tumour Necrosis Factor: Precursor Structure, Expression and Homology to Lymphotoxin", *Nature*, 312:724-729 (1984).
Eck, M.J. and Sprang, S.R., "The Structure of Tumor Necrosis Faction —αat 2.6Å Resolution", *J. Biol. Chem.*, 264(29):17595-17605 (1989).
Katsube, Y., et al., "Analysis of $_K$ Light Chain Contribution to Anti-DNA Antibody Activity of a Human VH4-21-Encoded Monoclonal Antibody (NE-1) by Antibody-Phage Display Technique", *Int. J. Mol. Med.*, 1(5):863-868 (1998).
Möller, A., et al., "Monoclonal Antibodies to Human Tumore Necrosis Factor α: In Vitro and In Vivo Application", *Cytokine*, 2(3):162-169 (1990).
Liang, et al., "Production and Characterization of Monoclonal Antibodies Against Recombinant Human Tumor Necrosis Factor/Cachetin", Biochem. Biophys. Res. Comm., 137:847-854 (1986).
Meager, A., et al., "Preparation and Characterization of Monoclonal Antibodies Directed Against Antigenic Determinants of Recombinant Human Tumour Necrosis Factor (rTNF)", Hybridoma, 6:305-311 (1987).
Fendly, B.M., et al., "Murine Monoclonal Antibodies Defining Neutralizing Epitopes on Tumor Necrosis Factor", *Hybridoma*, 6:359-369 (1987).
Bringman, T.S. and Aggarwal, B.B., "Monoclonal Antibodies to Human Tumor Necrosis Factors Alpha and Beta: Application for Affinity Purification Immunoassays, and as Structural Probes", *Hybridoma*, 6:489-507 (1987).
Hirai, et al., "Production and Characterization of Monoclonal Antibodies to Human Tumor Necrosis Factor", J. Immunol., Meth., 96:57-62 (1987).
Luo, J., et al., "Probing of C-Terminal Lysine Variation in a Recombinant Monoclonal Antibody Producting using Chinese Hamster Ovary Cells with Chemically Defined Media", *Biotechnol. Bioeng.*, 109(9):2306-2315 (2012).

Ghaderi, D., et al., "Products Platforms for Biotherapeutic Glycoproteins. Occurrence, Impact and Challenges of Non-Human Sialylation", *Biotechnol. Genet Eng. Rev.*, 28:147-175 (2002).
Dick, Jr., L.W., et al., "C-Terminal Lysine Variants in Fully Human Monoclonal Antibodies; Investigation of Test Methods and Possible Causes", *Biotechnol Bioeng.*, 100(6): 1132-1143 (2008).
International Search Report for PCT/US2014/021574, dated Jun. 16, 2014.
EP 14768761.0 Extended Search Report dated Aug. 10, 2016 entitled "Manufacturing Methods to Control C-Terminal Lysine, Galactose and Sialic Acid Content in Recombinant Proteins.".
Luo, J., et al., "Probing of C-Terminal Lysine Variation in a Recombinant Monoclonal Antibody Production Using Chinese Hamster Ovary Cells With Chemically Defined Media", *Biotechnology and Bioengineering*, vol. 109; No. 9; 2306-2315 (2012).
Dinnis, D.M. and James D.C., "Engineering Mammalian Cell Factories for Improved Recombinant Monoclonal Antibody Production: Lessons From Nature?," Biotechnology and Bioengineering, vol. 91;No. 2: 180-189 (2005).
Kim, D.Y. et al., "Development of serum-free media for a recombinant CHO cell line producing recombinant antibody," Enzyme and Microbial Technology, vol. 39; 426-433 (2006).
Park, J.Y. and Jongstra-Bilen, J., "Interactions between membrane IgM and the cytoskeleton involve the cytoplasmic domain of the immunoglobulin receptor," Eur. J. Immunol., vol. 27; No. 11; 3001-3009 (1997).
Raju, T.S., "Terminal sugars of Fc glycans influence antibody effector functions of IgGs," Current Opinion in Immunology, vol. 20; 471-478 (2008).
Communication of a Notice of Opposition for European Patent Application No. 14768761.0, entitled: "Manufacturing Methods to Control C-Terminal Lysine, Galactose and Sialic Acid Content in Recombinant Proteins," mailed May 20, 2019 (35 pages).
Notice of Opposition for European Patent Application No. 14768761. 0, entitled: "Manufacturing Methods to Control C-Terminal Lysine, Galactose and Sialic Acid Content in Recombinant Proteins," mailed May 15, 2019 (35 pages).
Reply of the Patent Proprietor to the Notice of Opposition for European Patent Application No. 14768761.0, entitled: "Manufacturing Methods to Control C-Terminal Lysine, Galactose and Sialic Acid Content in Recombinant Proteins," mailed Oct. 14, 2019 (91 pages).
Summons to Attend Oral Proceedings for the Opposition for European Patent Application No. 14768761.0, entitled: "Manufacturing Methods to Control C-Terminal Lysine, Galactose and Sialic Acid Content in Recombinant Proteins," mailed Jan. 30, 2020 (17 pages).
International Nonproprietary Names for Pharmaceutical Substances (INN)—WHO Drug Information, Col. 12; No. 1; 39-66 (1998).
Summons to Attend Oral Proceedings for the Opposition for European Patent Application No. 14768761.0, titled: "Manufacturing Methods to Control C-Terminal Lysine, Galactose and Sialic Acid Content in Recombinant Proteins," mailed Oct. 1, 2020 (4 pages).
Opponent's written submissions in preparation for oral proceedings for the Opposition for European Patent Application No. 14768761. 0, titled: "Manufacturing Methods to Control C-Terminal Lysine, Galactose and Sialic Acid Content in Recombinant Proteins," mailed Aug. 19, 2020 (15 pages).

\* cited by examiner

```
1
Val Arg Ser Ser Arg Thr Pro Ser Asp Lys Pro Val Ala His Val Val Ala Asn Pro
                                 10
21
Gln Ala Glu Gly Gln Leu Gln Trp Leu Asn Arg Arg Ala Asn Ala Leu Leu Ala Asn Gly
                                 30
41
Val Glu Leu Arg Asp Asn Gln Leu Val Val Pro Ser Glu Gly Leu Tyr Leu Ile Tyr Ser
                                 50
61
Gln Val Leu Phe Lys Gly Gln Gly Cys Pro Ser Thr His Val Leu Leu Thr His Thr Ile
                                 70
81
Ser Arg Ile Ala Val Ser Tyr Gln Thr Lys Val Asn Leu Leu Ser Ala Ile Lys Ser Pro
                                 90
101
Cys Gln Arg Glu Thr Pro Glu Gly Ala Glu Ala Lys Pro Trp Tyr Glu Pro Ile Tyr Leu
                                 110
121
Gly Gly Val Phe Gln Leu Glu Lys Gly Asp Arg Leu Ser Ala Glu Ile Asn Arg Pro Asp
                                 130
141
Tyr Leu Asp Phe Ala Glu Ser Gly Gln Val Tyr Phe Gly Ile Ile Ala Leu
                                 150
```

*FIG. 28*

GACATCTTGCTGACTCAGTCCTCCAGCCATCCCTGTCTGTGAGTCCAGGAGAAAGAGTCAGT
AspIleLeuLeuThrGlnSerProAlaIleLeuSerValSerProGlyGluArgValSer

TTCTCCTGCAGGGCCAGTCAGTTCGTTGGCTCAAGCATCCACTGGTATCAGCAAAGAACA
PheSerCysArgAlaSerGlnPheValGlySerSerIleHisTrpTyrGlnGlnArgThr

AATGGTTCTCCAAGGCTTCTCATAAAGTATGCTTCTGAGTCTTATGTCTGGGATCCCTTCC
AsnGlySerProArgLeuLeuIleLysTyrAlaSerGluSerMetSerGlyIleProSer

AGGTTTAGTGGCAGTGGATCAGGGACAGATTTTACTCTTAGCATCAACACTGTGGAGTCT
ArgPheSerGlySerGlySerGlyThrAspPheThrLeuSerIleAsnThrValGluSer

GAAGATATTGCAGATTATTACTGTCAACAAAGTCATAGCTGGCCATTCACGTTCCGGCTCG
GluAspIleAlaAspTyrTyrCysGlnGlnSerHisSerTrpProPheThrPheGlySer

GGGACAAATTTGGAAGTAAAA
GlyThrAsnLeuGluValLys

FIG. 29A

GAA GTG AAG CTT GAG GAG TCT GGA GGA GGC TTG GTG CAA CCT GGA GGA TCC ATG AAA CTC
Glu Val Lys Leu Glu Glu Ser Gly Gly Gly Leu Val Gln Pro Gly Gly Ser Met Lys Leu

TCC TGT GTT GCC TCT GGA TTC ATT TTC AGT AAC CAC TGG ATG AAC TGG GTC CGC CAG TCT
Ser Cys Val Ala Ser Gly Phe Ile Phe Ser Asn His Trp Met Asn Trp Val Arg Gln Ser

CCA GAG AAG GGG CTT GAG TGG GTT GCT GAA ATT AGA TCA AAA TCT ATT AAT TCT GCA ACA
Pro Glu Lys Gly Leu Glu Trp Val Ala Glu Ile Arg Ser Lys Ser Ile Asn Ser Ala Thr

CAT TAT GCG GAG TCT GTG AAA GGG AGG TTC ACC ATC TCA AGA GAT GAT TCC AAA AGT GCT
His Tyr Ala Glu Ser Val Lys Gly Arg Phe Thr Ile Ser Arg Asp Asp Ser Lys Ser Ala

GTC TAC CTG CAA ATG ACC GAC TTA AGA ACT GAA GAC ACT GGC GTT TAT TAC TGT TCC AGG
Val Tyr Leu Gln Met Thr Asp Leu Arg Thr Glu Asp Thr Gly Val Tyr Tyr Cys Ser Arg

AAT TAC TAC GGT AGT ACC TAC GAC TAC TGG GGC CAA GGC ACC ACT CTC ACA GTC TCC
Asn Tyr Tyr Gly Ser Thr Tyr Asp Tyr Trp Gly Gln Gly Thr Thr Leu Thr Val Ser

FIG. 29B

MANUFACTURING METHODS TO CONTROL C-TERMINAL LYSINE, GALACTOSE AND SIALIC ACID CONTENT IN RECOMBINANT PROTEINS

RELATED APPLICATIONS

This application is a continuation of U.S. application Ser. No. 14/207,915, filed on Mar. 13, 2014, which claims the benefit of U.S. Provisional Application No. 61/791,094, filed on Mar. 15, 2013. The entire teachings of the above applications are incorporated herein by reference.

BACKGROUND OF THE INVENTION

C-terminal lysine (CTL) is rapidly removed from injected antibodies, including infliximab, by endogenous circulating carboxypeptidases in the blood stream (Cai, B. et al., "C-terminal Lysine Processing of Human Immunoglobulin G2 Heavy Chain in Vivo," *Biotechnol. Bioeng.* 2011; 108:404-412) and, therefore, is believed to have little, if any, impact on product safety and efficacy. However, CTL content in recombinant proteins having CTL residues can be used as a measure of manufacturing consistency and product homogeneity.

INCORPORATION BY REFERENCE OF MATERIAL IN ASCII TEXT FILE

This application incorporates by reference the Sequence Listing contained in the following ASCII text file:

a) File name: 01482007002_SEQLIST.txt; created Apr. 29, 2016, 8 KB in size.

In contrast to CTL content, sialic acid content in recombinant proteins has been associated with many phenomena of physiological importance in humans. For example, the presence of sialic acid in glycoproteins, such as erythropoietin, promotes a long circulatory half-life, while the absence of sialic acid in erythropoietin leads to rapid clearance of the protein from circulation. In addition, increased sialic acid content in proteins may modulate immunogenicity of the protein in humans. Due to the importance of sialic acid in product safety and efficacy, sialic acid content should be kept within a range reflective of the range used in the clinic.

Therefore, there is a need to understand and control process-related factors that affect CTL and sialic acid content in recombinant proteins, particularly recombinant proteins, such as REMICADE® (infliximab) or HUMIRA® (adalimumab), being administered to humans.

SUMMARY OF THE INVENTION

Disclosed herein are methods for producing an antibody, for example, an anti-tumor necrosis factor alpha (TNFα) antibody, such as monoclonal antibody cA2 (also referred to herein as infliximab), having a desired C-terminal lysine (CTL) content, sialic acid content, galactose content and/or ratio of sialic acid to galactose by controlling culture conditions, including zinc concentration, ethylenediaminetetraacetic acid (EDTA) concentration and harvest time.

One embodiment of the invention is a method for producing an antibody having a C-terminal lysine content of about 20% to about 70%, and a sialic acid content of about 1% to about 20%, the method comprising culturing a zinc-responsive host cell transfected with DNA encoding the antibody in a culture medium comprising at least 0.5 μM zinc; and controlling the concentration of zinc in the culture medium, thereby producing the antibody. In some embodiments, the C-terminal lysine content of the antibody is about 40% to about 70%, e.g., about 55% to about 65%, e.g., or about 60%. In some embodiments, the sialic acid content of the antibody is about 3% to about 14%. In some embodiments, the antibody has a galactose content of about 50% to about 90%, or about 45% to about 85%. In some embodiments, the antibody has a ratio of sialic acid to galactose of about 0.05 to about 0.20.

In some embodiments, the antibody is an anti-TNFα antibody or antigen-binding fragment thereof, wherein said anti-TNFα antibody or antigen-binding fragment thereof (i) competitively inhibits binding of A2 (ATCC Accession No. PTA-7045) to human TNFα; and (ii) binds to a neutralizing epitope of human TNFα with an affinity of at least $1 \times 10^8$ liter/mole, measured as an association constant (Ka). The anti-TNFα antibody or antigen-binding fragment thereof can be, e.g., a chimeric antibody, a human antibody, or a humanized antibody. In some embodiments, the anti-TNFα antibody or antigen-binding fragment thereof can be of immunoglobulin class IgG1, IgG2, IgG3, IgG4 or IgM and, in some embodiments, comprises an IgG1 constant region. In some embodiments, the anti-TNFα antibody or antigen-binding fragment thereof is selected from the group consisting of Fab, Fab', F(ab')$_2$ and Fv.

In some embodiments, the anti-TNFα antibody or antigen-binding fragment thereof comprises a human constant region and a non-human variable region, or a human constant region and a human variable region.

In some embodiments, the antibody or antigen-binding fragment thereof comprises at least one human light chain and at least one human heavy chain. In some embodiments, the light chain comprises all antigen-binding regions of the light chain of A2 (ATCC Accession No. PTA-7045). In some embodiments, the heavy chain comprises all antigen-binding regions of the heavy chain of A2 (ATCC Accession No. PTA-7045). In yet other embodiments, the light chain comprises all antigen-binding regions of the light chain of A2 (ATCC Accession No. PTA-7045) and the heavy chain comprises all antigen-binding regions of the heavy chain of A2 (ATCC Accession No. PTA-7045).

In some embodiments, the anti-TNFα antibody or antigen-binding fragment thereof comprises an IgG1 human constant region and a non-human variable region comprising an amino acid sequence selected from the group consisting of SEQ ID NO: 3 and SEQ ID NO: 5, or encoded by a nucleic acid sequence selected from the group consisting of SEQ ID NO: 2 and SEQ ID NO: 4.

In some embodiments, the anti-TNFα antibody or antigen-binding fragment thereof has epitopic specificity identical to monoclonal antibody cA2 and, in some embodiments, the anti-TNFα antibody or antigen-binding fragment thereof is monoclonal antibody cA2.

In some embodiments, the concentration of zinc in the culture medium is in the range of about 0.6 μM to about 6.5 μM, or about 0.6 μM to about 1.1 μM.

In some embodiments, the culture medium further comprises EDTA in a concentration range of about 2.5 μM to about 30 μM, or about 5 μM to about 16 μM, and the method further comprises controlling the concentration of EDTA in the culture medium.

In some embodiments, the method further comprises recovering the antibody, for example, when the zinc-responsive host cells in the culture medium reach a cell density of about 1.5 million cells per mL to about 11 million cells per mL, or about 3 million cells per mL to about 11 million cells per mL. In some embodiments, the concentration of zinc is controlled until the antibody is recovered, or during an exponential growth phase of the zinc-responsive host cells.

In some embodiments of the invention, controlling the concentration of zinc comprises monitoring the concentration of zinc in the culture medium, and regulating the concentration of zinc in the culture medium, such that the concentration of zinc in the culture medium is at least 0.5 µM or in the range of about 0.6 µM to about 6.5 µM.

In some embodiments of the invention, the zinc-responsive host cell is an SP2/0 cell.

Another embodiment of the invention is a method for controlling C-terminal lysine content of an antibody having a C-terminal lysine content of about 20% to about 70%, in a process for biosynthesizing the antibody in a culture medium, the method comprising monitoring a level of zinc in the culture medium during biosynthesis of the antibody; and regulating the level of zinc in the culture medium during biosynthesis of the antibody.

Yet another embodiment of the invention is a method for controlling sialic acid content of an antibody having a sialic acid content of about 1% to about 20% in a process for biosynthesizing the antibody in a culture medium, the method comprising monitoring a level of zinc in the culture medium during biosynthesis of the antibody; and regulating the level of zinc in the culture medium during biosynthesis of the antibody.

Yet another embodiment of the invention is a method for controlling galactose content of an antibody having a galactose content of about 50% to about 90% in a process for biosynthesizing the antibody in a culture medium, the method comprising monitoring a level of zinc in the culture medium during biosynthesis of the antibody; and regulating the level of zinc in the culture medium during biosynthesis of the antibody.

Yet another embodiment of the invention is a method for controlling the ratio of sialic acid to galactose in an antibody having a ratio of sialic acid to galactose of about 0.05 to about 0.20 in a process for biosynthesizing the antibody in a culture medium, the method comprising monitoring a level of zinc in the culture medium during biosynthesis of the antibody; and regulating the level of zinc in the culture medium during biosynthesis of the antibody.

In some embodiments of a method for controlling CTL, sialic acid or galactose content, or ratio of sialic acid to galactose, the antibody is an anti-TNFα antibody or antigen-binding fragment thereof, and/or the antibody is biosynthesized by an SP2/0 cell.

In one embodiment, the antibody is a mAb which binds amino acids of an epitope of TNF, which is produced by a hybridoma or by a recombinant host. In one embodiment, the antibody is a chimeric antibody which recognizes an epitope recognized by A2. In another embodiment, the antibody is a chimeric antibody designated as chimeric A2 (cA2) (i.e., infliximab).

Characterization and methods of making and using anti-TNF antibodies are disclosed and described in detail in, for example, "Anti-TNF antibodies, compositions, methods and uses", George Heavner et al., U.S. Pat. No. 7,250,165, filed on Aug. 1, 2001, issued on Jul. 31, 2007 and "Anti-TNF antibodies, compositions, methods and uses", Jill Giles-Komar et al., U.S. application Ser. No. 10/394,471, Publication number US 2004/0185047 A1, filed on Mar. 21, 2003, and "Recombinant A2-specific TNFα-specific antibodies", Junming Le et al., U.S. Pat. No. 7,252,823, filed on Feb. 6, 2004, issued on 7 Aug. 2007 (all incorporated herein by reference in their entirety).

In some embodiments, the antibodies include murine mAb A2, which is produced by a cell line designated c134A and chimeric antibody cA2, which is produced by a cell line designated c168A. Cell line c134A is stored at Janssen Research & Development, Welsh & McKean Road, Springhouse, Pa. Cell line c168A is stored at Janssen Research & Development, 200 Great Valley Parkway, Malvern, Pa., 19355, Janssen Biologics BV, Leiden, The Netherlands.

The methods disclosed herein can be used to improve batch homogeneity in, for example, a commercial manufacturing process, such as the manufacturing process used to produce infliximab, a monoclonal anti-TNFα antibody used in the treatment of, for example, autoimmune diseases in humans.

BRIEF DESCRIPTION OF THE FIGURES

The foregoing will be apparent from the following more particular description of example embodiments of the invention, as illustrated in the accompanying figures.

The patent or application file contains at least one drawing executed in color. Copies of this patent or patent application publication with color drawings will be provided by the Office upon request and payment of the necessary fee.

FIG. 28 is an amino acid sequence of human TNF as SEQ ID NO:1.

FIGS. 29A-29B. FIG. 29A is a nucleic acid sequence (SEQ ID NO:2) and corresponding amino acid sequence (SEQ ID NO:3) of a cloned cA2 light chain variable region. FIG. 29B is a nucleic acid sequence (SEQ ID NO:4) and corresponding amino acid sequence (SEQ ID NO:5) of a cloned cA2 heavy chain variable region.

DETAILED DESCRIPTION OF THE INVENTION

Figure 1:
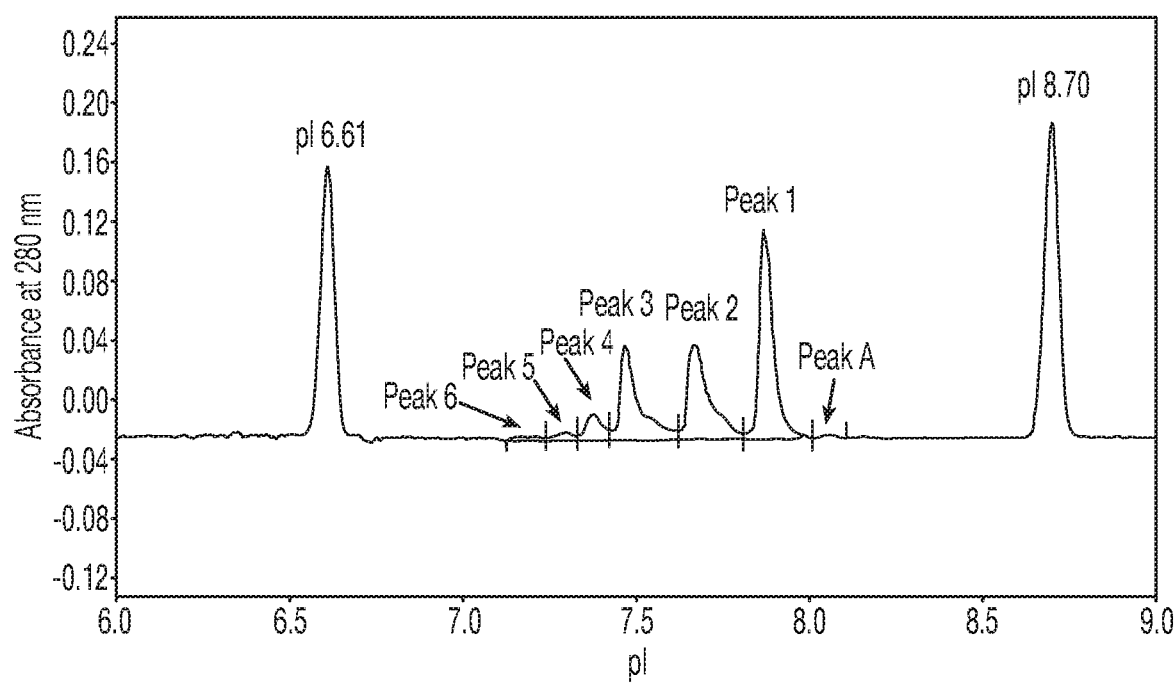
FIG. 1 shows a capillary isoelectric focusing (cIEF) electropherogram of a sample of infliximab.

A description of example embodiments of the invention follows.

One embodiment provides a method for producing an antibody having a C-terminal lysine content of about 20% to about 70%, and a sialic acid content of about 1% to about 20%, comprising culturing a zinc-responsive host cell transfected with DNA encoding the antibody in a culture medium comprising at least 0.5 µM zinc; and controlling the concentration of zinc in the culture medium, thereby producing the antibody.

CTL content is expressed herein as the percentage of heavy chains possessing a C-terminal lysine and can be calculated using the following equation: CTL content (%)= (number of heavy chains possessing a CTL)/(total number of heavy chains)×100. CTL removal is expressed herein as the percentage of heavy chains lacking a C-terminal lysine (des-Lys). So, "80% Des-Lys" is equivalent to 20% CTL content. In some embodiments of the methods described herein, CTL content of the antibody or anti-TNFα antibody, or antigen binding fragment thereof, is about 40% to about 70%, specifically, about 55% to about 65%, and more specifically, about 60%.

Sialic acid content is expressed herein as the percentage of oligosaccharides containing sialic acid, and can be calculated using the following equation: sialic acid content (%)=(number of oligosaccharides containing a sialic acid)/ (total number of oligosaccharides)×100. This equation applies independently of the number of sialic acid residues in the oligosaccharide. In other words, regardless of whether there are, for example, one or two sialic acid residues in the oligosaccharide, the oligosaccharide is only counted once for the purposes of calculating sialic acid content. In some embodiments of the methods described herein, sialic acid content of the antibody or anti-TNFα antibody, or antigen binding fragment thereof, is about 3% to about 14%.

Galactose content is expressed herein as the percentage of oligosaccharides containing galactose, and can be calculated using the following equation: galactose content (%)=(number of oligosaccharides containing a galactose)/(total number of oligosaccharides)×100. This equation applies independently of the number of galactose units in the oligosaccharide. In other words, regardless of whether there are, for example, one or two galactose residues in the oligosaccharide, the oligosaccharide is only counted once for the purposes of calculating galactose content. In some embodiments of the methods described herein, an antibody or anti-TNFα antibody, or antigen binding fragment thereof, has a galactose content of about 50% to about 90% and, specifically, of about 45% to about 85%.

Typically, both heavy chains of an antibody, such as infliximab, are glycosylated. However, in some circumstances, some of the heavy chains remain aglycosylated. For example, in some embodiments, approximately 94% of antibody molecules are glycosylated on both chains, approximately 6% of antibody molecules are hemi-glycosylated, and approximately 0.1% of antibody molecules are fully aglycosylated.

The ratio of sialic acid to galactose is calculated from the molar ratio of sialic acid to galactose in the oligosaccharides of infliximab. In some embodiments of the methods described herein, the antibody or anti-TNFα antibody, or antigen binding fragment thereof, has a ratio of sialic acid to galactose of about 0.05 to about 0.20.

"Zinc-responsive host cell," as used herein, means a host cell that responds to fluctuations in zinc concentration in its culture medium. Responsiveness of a host cell to fluctuations in zinc concentration can be evaluated, for example, by measuring the effect of varying zinc concentrations on CTL content, sialic acid content, galactose content, and ratio of sialic acid to galactose in an antibody produced by the host cell. Methods for assessing CTL content, sialic acid content, galactose content, and ratio of sialic acid to galactose in an antibody produced by a host cell are described in the Exemplification.

The invention provides a culture medium comprising an amount of zinc greater than about 0.5 µM. In some embodiments, the concentration of zinc in the culture medium is in the range of about 0.6 µM to about 6.5 µM and, preferably, in the range of about 0.6 µM to about 1.1 µM. In some embodiments, the amount or concentration of zinc in the culture medium is non-toxic to the zinc-responsive host cells, for example, does not reduce or substantially reduce cell viability, cell growth or antibody production, particularly in the first 20-25 days of the culture.

In some embodiments, the culture medium further comprises ethylenediaminetetraacetic acid (EDTA) ("EDTA" or "total EDTA" as referred herein) in a concentration range of about 2.5 µM to about 30 µM and, preferably, in a concentration range of about 5 µM to about 16 µM. "Iron-free EDTA" as used herein, refers to EDTA that is not chelated to iron ($Fe^{+3}$). The amount or concentration of iron-free EDTA (abbreviated [EDTA-$Fe^{+3}$]) can be calculated by subtracting the amount or concentration of $Fe^{3+}$ from the amount or concentration of total EDTA. The ion Fe+3 has the highest affinity for EDTA of the metal ions in the culture medium. Therefore, Fe+3, when present will preferentially bind EDTA in the cell culture medium. The concentration of iron-free EDTA represents the EDTA available to bind Zn+2 and other metal ions in the culture medium.

In some embodiments of the methods described herein, the amount or concentration of EDTA and/or iron-free EDTA in the culture medium is non-toxic to the zinc-responsive host cells, for example, does not reduce or substantially reduce cell viability, cell growth or antibody production, particularly in the first 20-25 days of the culture.

"Controlling," as used herein, means to verify and/or regulate. Controlling includes sensing/measuring a substance being controlled (directly or indirectly) and using those measurements to provide feedback to make corrections toward the desired result. Controlling includes both monitoring and regulating, for example, the concentration of zinc and/or EDTA and/or iron-free EDTA in a culture medium. Typically, the concentration of zinc and/or EDTA and/or iron-free EDTA is controlled for the duration of the culture. In some embodiments of the methods described herein, the concentration of zinc and/or EDTA and/or iron-free EDTA is controlled during an exponential growth phase of the zinc-responsive host cells, or during the first approximately 10-25 days of culture.

The concentration of zinc and/or EDTA and/or iron-free EDTA in the culture medium can be controlled by, for example, monitoring a level of zinc and/or EDTA and/or iron-free EDTA in the culture medium; and regulating the level of zinc and/or EDTA and/or iron-free EDTA in the culture medium. Therefore, in some embodiments of the methods described herein, controlling the concentration of zinc comprises monitoring the concentration of zinc in the culture medium, and regulating the concentration of zinc in the culture medium, such that the concentration of zinc in the culture medium is at least 0.5 µM, or about 0.6 µM to about 6.5 µM.

Methods of monitoring the level of zinc and/or EDTA and/or iron-free EDTA are known to those of skill in the art. For example, the concentration of zinc and other metal ions may be measured by inductively coupled plasma mass spectrometry (ICP-MS), while the concentration EDTA may be measured by an HPLC method.

To "regulate," as used herein, means to put or maintain in order. Regulating includes maintaining, for example, the concentration of zinc and/or EDTA in a culture medium, and adjusting, for example, the concentration of zinc and/or EDTA in a culture medium, as necessary. Thus, zinc (e.g., a non-toxic amount of zinc) can be included in the culture medium at an initial concentration of, for example, greater than about 5 µM, then adjusted to a concentration of for example, 0.6 µM to about 1.1 µM. The adjustment can be made, for example, concurrently with or just after the transition from the exponential growth phase to the steady-state phase. Alternatively, the concentration of zinc can be maintained at a concentration of, for example, 0.6 µM to about 1.1 µM for the duration of the culture.

Regulation of the level of zinc and/or EDTA and/or iron-free EDTA can be achieved, for example, through direct addition of zinc, iron and/or EDTA to the culture medium; through blending of raw materials that contain zinc, iron and/or EDTA; through treatment of raw materials to adjust the zinc, iron and/or EDTA concentrations thereof; and/or through modification of the manufacturing process of the raw materials to achieve desired levels of zinc, iron and/or EDTA. Methods of regulating components of a culture medium are known to those of skill in the art.

The culture medium can comprise other ingredients in addition to zinc and/or EDTA. The choice of a suitable culture medium is within the knowledge of one skilled in the art. In some embodiments, the culture medium is a serum-free medium.

Any host cells known in the art for use to produce antibodies can be used, including mammalian cells, such as SP2/0 cells, e.g., mouse SP2/0 cell (American Type Culture Collection (ATCC), Manassas, Va., CRL-1581), Other exemplary host cells are NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44. Cells can be cultured in single-cell suspension or in an anchorage-dependent fashion.

A variety of culture systems are known in the art, including flasks, roller bottles, and bioreactors, e.g., stirred-tank bioreactors. Culture medium can be added in a batch process, in which culture medium is added once to the cells in a single batch or, preferably, in a fed batch process, in which small batches of culture medium are periodically added. The host cells can also be cultured in a perfusion culture, which involves continuously removing a volume of culture medium from the culture, and replacing the removed volume with a comparable volume of fresh medium. Typically, perfused cultures can be operated to achieve higher cell densities than batch cultures, and can be maintained for longer periods of time. Perfused cultures also enable repeated harvests.

Methods for producing an antibody can further comprise recovering the antibody. In some embodiments, the antibody can be recovered when the zinc-responsive host cells in the culture medium reach a cell density of about 1.5 million cells per mL to about 11 million cells per mL and, preferably, about 3 million cells per mL to about 11 million cells per mL. An antibody can be recovered, for example, by direct product capture (DPC). In some embodiments of the methods described herein, the concentration of zinc is controlled until the antibody is recovered.

CTL and sialic acid content can be yet more precisely controlled by controlling the cell age at the time of product harvest or recovery. Therefore, in some embodiments of the methods described herein, the antibody is recovered concurrently with or just after the transition from the exponential growth phase to the steady-state phase. In other embodiments, the antibody is recovered during the steady-state phase of culture growth. In some embodiments, the antibody is recovered within the first 25 days of culture, for example, at Days 10-25, Days 15-20, or around Day 20. In other embodiments, the antibody is recovered after the first 25 days of culture.

Also provided herein is a method for controlling C-terminal lysine content of an antibody having a C-terminal lysine content of about 20% to about 70%, in a process for biosynthesizing the antibody in a culture medium, the method comprising monitoring a level of zinc in the culture medium during biosynthesis of the antibody; and regulating the level of zinc in the culture medium during biosynthesis of the antibody.

Also provided herein is a method for controlling sialic acid content of an antibody having a sialic acid content of about 1% to about 20% in a process for biosynthesizing the antibody in a culture medium, the method comprising monitoring a level of zinc in the culture medium during biosynthesis of the antibody; and regulating the level of zinc in the culture medium during biosynthesis of the antibody.

Also provided herein is a method for controlling galactose content of an antibody having a galactose content of about 50% to about 90% in a process for biosynthesizing the antibody in a culture medium, the method comprising monitoring a level of zinc in the culture medium during biosynthesis of the antibody; and regulating the level of zinc in the culture medium during biosynthesis of the antibody.

Also provided herein is a method for controlling the ratio of sialic acid to galactose in an antibody having a ratio of sialic acid to galactose of about 0.05 to about 0.20 in a process for biosynthesizing the antibody in a culture medium, the method comprising monitoring a level of zinc in the culture medium during biosynthesis of the antibody; and regulating the level of zinc in the culture medium during biosynthesis of the antibody.

In some embodiments of a method for controlling CTL, sialic acid or galactose content, or ratio of sialic acid to galactose, the antibody is an anti-TNFα antibody or antigen-binding fragment thereof, and/or the antibody is biosynthesized by an SP2/0 cell or a CHO cell.

Antibodies and Fragments Thereof

As used herein, an "antibody" includes a whole antibody and any antigen binding fragment or a single chain thereof.

Antibodies can include at least one of a heavy chain constant region ($H_c$), a heavy chain variable region ($H_v$), a light chain variable region ($L_v$) and a light chain constant region ($L_c$), wherein a polyclonal Ab, monoclonal Ab, fragment and/or regions thereof include at least one heavy chain variable region ($H_v$) or light chain variable region ($L_v$) which binds a portion of an antigen and inhibits and/or neutralizes at least one biological activity of the antigen.

An antibody or antigen-binding fragment can comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

An antibody can be primate, mammalian, murine, chimeric, humanized, or human. An antibody can include, for example, at least one of murine-human chimeric antibodies, murine antibodies, human antibodies or any portions thereof, having at least one antigen binding fragment or region of an immunoglobulin variable region.

Chimeric antibodies are molecules different portions of which are derived from different animal species, such as those having variable region derived from a murine mAb and a human immunoglobulin constant region. For example, they can retain at least one distinct domains, usually the variable domain, from one species and the remainder from another species; e.g., mouse-human chimeric antibodies. They are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., *Proc. Natl. Acad. Sci. USA* 81:3273-3277 (1984); Morrison et al., *Proc. Natl. Acad. Sci. USA* 81:6851-6855 (1984); Neuberger et al., *Nature* 314:268-270 (1985); and Harlow and Lane *Antibodies: a Laboratory Manual* Cold Spring Harbor Laboratory (1988)). These references are incorporated herein by reference in their entirety.

As used herein, the term "chimeric antibody" includes monovalent, divalent or polyvalent immunoglobulins. A monovalent chimeric antibody is a dimer (HL) formed by a chimeric H chain associated through disulfide bridges with a chimeric L chain. A divalent chimeric antibody is a tetramer ($H_2L_2$) formed by two HL dimers associated through at least one disulfide bridge. A polyvalent chimeric antibody can also be produced, for example, by employing a $C_H$ region that aggregates (e.g., from an IgM H chain, or μ chain).

"Humanized" antibodies (also known as CDR-grafted antibodies) are produced by a process to reduce the immunogenicity of monoclonal antibodies (mAbs) from xenogeneic sources (commonly rodent) and for improving the effector functions (e.g., ADCC, complement activation, and/or C1q binding). Generally, a humanized antibody has one or more amino acid residues from a source which is non-human, for example, but not limited to, mouse, rat, rabbit, non-human primate or other mammal. The engineered mAb can be engineered using molecular biology techniques. Simple CDR-grafting of rodent complementarity-determining regions (CDRs) into human frameworks often results in loss of binding affinity and/or specificity of the original mAb. In order to humanize an antibody, the design of the humanized antibody can include variations such as conservative amino acid substitutions in residues of the CDRs, and back substitution of residues from the rodent mAb into the human framework regions (back mutations). Methods for engineering or humanizing non-human or human antibodies are well known in the art.

The term "human antibody", as used herein, includes antibodies having variable and constant regions derived from or closely matching human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Thus, as used herein, the term "human antibody" refers to an antibody in which substantially every part of the protein (e.g., CDR, framework, CL, CH domains (e.g., CH1, CH2, CH3), hinge, (VL, VH)) is substantially similar to a human germline antibody.

As used herein, the term "human antibody" also refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. A human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Antibodies may be of any immunoglobulin class, including IgG, IgM, IgE, IgA, GILD and any subclass thereof. As used herein, "isotype" refers to the antibody class (e.g., IgM or IgG1) that is encoded by heavy chain constant region genes. In humans, there are five heavy chain isotypes and two light chain isotypes. For heavy chain, IgA1 and 2; IgD; IgG1, 2, 3, and 4; IgE; and IgM are isotypes of heavy chains. Kappa and lambda are isotypes of light chains. In certain embodiments, the heavy chain is an IgG class heavy chain. In other embodiments, the heavy chain is an IgM class heavy chain. In certain embodiments, the heavy chain further comprises at least about 8 amino acids of a J region.

Antibodies can be polyclonal antibodies, monoclonal antibodies (mAbs), anti-idiotypic (anti-Id) antibodies to antibodies that can be labeled in soluble or bound form, and fragments, regions or derivatives thereof, provided by any known technique, such as, but not limited to, enzymatic cleavage, peptide synthesis or recombinant techniques. Such antibodies can be capable of binding portions of an antigen (e.g., TNF) that inhibit the binding of antigen to antigen receptors.

Polyclonal antibodies are heterogeneous populations of antibody molecules derived from the sera of animals immunized with an antigen.

A monoclonal antibody (mAb) contains a substantially homogeneous population of antibodies specific to an antigen, A monoclonal antibody composition displays a single binding specificity for a particular epitope.

MAbs may be obtained by methods known to those skilled in the art. See, for example, Kohler and Milstein, Nature 256:495-497 (1975); U.S. Pat. No. 4,376,110; Ausubel et al., eds., Current Protocols in Molecular Biology, Greene Publishing Assoc. and Wiley Interscience, N.Y., (1987, 1992); and Harlow and Lane ANTIBODIES: A Laboratory Manual Cold Spring Harbor Laboratory (1988); Colligan et al., eds., Current Protocols in Immunology, Greene Publishing Assoc. and Wiley Interscience, N.Y., (1992, 1993), the contents of which references are incorporated entirely herein by reference.

An anti-idiotypic (anti-Id) antibody is an antibody which recognizes unique determinants generally associated with the antigen-binding site of an antibody. The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Antibody fragments include, for example, Fab, Fab', $F(ab')_2$ and Fv. These fragments lack the Fc fragment of an intact antibody, clear more rapidly from the circulation, and can have less non-specific tissue binding than an intact antibody (Wahl et al., J. Nucl. Med. 24:316-325 (1983)). These fragments are produced from intact antibodies using methods well known in the art, for example by proteolytic cleavage with enzymes such as papain (to produce Fab fragments) or pepsin (to produce $F(ab')_2$ fragments).

As used herein, the term "antigen binding fragment" refers to that portion of an antibody molecule which contains the amino acid residues that interact with an antigen and confer on the antibody its specificity and affinity for the antigen. An "antigen" is a molecule or a portion of a molecule capable of being bound by an antibody which is additionally capable of inducing an animal to produce antibody capable of binding to an epitope of that antigen. An antigen can have one or more than one epitope. The antibody region includes the "framework" amino acid residues necessary to maintain the proper conformation of the antigen-binding residues.

An "antigen binding fragment" or portion thereof includes, e.g., single chain antibodies and fragments thereof. Examples of antigen binding fragments include (i) a Fab fragment, a monovalent fragment consisting of the VL, VH, CL and CH, domains; (ii) a $F(ab')_2$ fragment, a bivalent fragment comprising two Fab fragments linked by a disulfide bridge at the hinge region; (iii) a Fd fragment consisting of the VH and CH, domains; (iv) a Fv fragment consisting of the VL and VH domains of a single arm of an antibody, (v) a dAb fragment in which the VH and VL domains are expressed on a single polypeptide chain; and (vi) one or more isolated complementarity determining regions (CDRs). Such fragments can be produced by enzymatic cleavage, synthetic or recombinant techniques, as known in the art and/or as described herein. In some embodiments, fragments can include one or more portions of the antibody chain, such as the heavy chain constant, joining, diversity or variable regions, or the light chain constant, joining or variable regions.

The antigen binding region can be of non-human, e.g., murine origin. In some embodiments, the antigen binding region can be derived from a rabbit or a rodent, such as a rat or hamster.

A antigen binding fragment of a chimeric antibody can be derived from a non-human antibody specific for a human antigen. In some embodiments, sources for the DNA encoding such a chimeric antibody include cell lines which produce antibody, preferably hybrid cell lines commonly known as hybridomas. In one embodiment, the hybridoma is the A2 hybridoma cell line.

The term "epitope" means a protein determinant capable of specific binding to an antibody. Epitopes usually consist of chemically active surface groupings of molecules such as amino acids or sugar side chains and usually have specific three-dimensional structural characteristics, as well as specific charge characteristics. An "epitope" can be that portion of any molecule capable of being recognized by and bound by an antibody at one or more of the Ab's antigen binding regions. By "inhibiting and/or neutralizing epitope" is intended an epitope, which, when bound by an antibody, results in loss of biological activity of the molecule or organism containing the epitope, in vivo, in vitro or in situ, more preferably in vivo, for example, binding of TNF to a TNF receptor.

The antibodies can be, for example, isolated, recombinant and/or synthetic antibodies.

A "recombinant antibody", as used herein, includes all antibodies that are prepared, expressed, created or isolated by recombinant means. The term "recombinant host cell" (or simply "host cell"), refers to a cell into which a recombinant expression vector has been introduced. Recombinant host cells include, for example, CHO cell lines or a mouse myeloma SP2/0 derived cell line. Recombinant antibodies, such as murine or chimeric murine-human or human-human antibodies can be produced using known techniques. See, e.g., Ausubel et al., eds. *Current Protocols in Molecular Biology*, Wiley Interscience, N.Y. (1987, 1992, 1993); and Sambrook et al. *Molecular Cloning: A Laboratory Manual*, Cold Spring Harbor Laboratory Press (1989), the entire contents of which are incorporated herein by reference.

Antibodies, fragments or derivatives having chimeric H chains and L chains of the same or different variable region binding specificity, can be prepared, for example, by appropriate association of the individual polypeptide chains, according to known method steps, e.g., according to Ausubel supra, Harlow infra, and Colligan infra, the contents of which references are incorporated entirely herein by reference.

With this approach, hosts expressing chimeric H chains (or their derivatives) are separately cultured from hosts expressing chimeric L chains (or their derivatives), and the immunoglobulin chains are separately recovered and then associated. Alternatively, the hosts can be co-cultured and the chains allowed to associate spontaneously in the culture medium, followed by recovery of the assembled immunoglobulin, fragment or derivative.

The hybrid cells are formed by the fusion of a non-human anti-hTNFα antibody-producing cell, typically a spleen cell of an animal immunized against either natural or recombinant human TNF, or a peptide fragment of the human TNFα protein sequence. Alternatively, the non-human anti-TNFα antibody-producing cell can be a B lymphocyte obtained from the blood, spleen, lymph nodes or other tissue of an animal immunized with TNF.

The second fusion partner, which provides the immortalizing function, can be a lymphoblastoid cell or a plasmacytoma or myeloma cell, which is not itself an antibody producing cell, but is malignant. In some embodiments, the fusion partner cells include the hybridoma SP2/0-Ag14, abbreviated as SP2/0 (ATCC CRL1581) and the myeloma P3X63Ag8 (ATCC TIB9), or its derivatives. See, e.g, Ausubel infra, Harlow infra, and Colligan infra, the contents of which references are incorporated entirely herein by reference.

An "isolated antibody," as used herein, is intended to refer to an antibody which is substantially free of other antibodies having different antigenic specificities. An isolated antibody that specifically binds to an epitope of a human antigen may, however, have cross-reactivity to other related antigens. Moreover, an isolated antibody may be substantially free of other cellular materials and/or chemicals.

Methods for determining mAb specificity and affinity by competitive inhibition can be found, for example, in Harlow, et al., *Antibodies: A Laboratory Manual*, Cold Spring Harbor Laboratory Press, Cold Spring Harbor, N.Y., 1988), Colligan et al., eds., *Current Protocols in Immunology*, Greene Publishing Assoc. and Wiley Interscience, N.Y., (1992, 1993), and Muller, *Meth. Enzymol.* 92:589-601 (1983), which references are entirely incorporated herein by reference.

In some embodiments, the antibody can be a biologically active antibody. Biologically active antibodies have a specific activity at least 20%, 30%, or 40%, and preferably at least 50%, 60%, or 70%, and most preferably at least 80%, 90%, or 95%-100% of that of the native (non-synthetic), endogenous or related and known antibody. Methods of assaying and quantifying measures of enzymatic activity and substrate specificity, are well known to those of skill in the art.

Anti-TNFα Antibodies

In some embodiments, the antibodies produced by the methods described herein are anti-tumor necrosis factor-α (TNFα) antibodies. As used herein, tumor necrosis factor-α (TNFα) and tumor necrosis factor (TNF) are used interchangeably to refer to tumor necrosis factor-α (TNFα), unless otherwise specifically noted. Likewise, tumor necrosis factor-α (TNFα) and tumor necrosis factor (TNF) antibodies and anti-tumor necrosis factor-α (TNFα) and anti-tumor necrosis factor (TNF) antibodies are used interchangeably, unless otherwise specifically noted.

TNFα is a soluble homotrimer of 17 kD protein subunits (Smith, et al., *J. Biol. Chem.* 262:6951-6954 (1987)). A membrane-bound 26 kD precursor form of TNF also exists (Kriegler et al., *Cell* 53:45-53 (1988)). For reviews of TNF, see Beutler, et al., *Nature* 320:584 (1986), Old, *Science* 230:630 (1986), and Le, et al., *Lab. Invest.* 56:234. The complete primary sequence of human TNFα, according to Pennica et al., *Nature* 312:724-729 (1984) is shown in FIG. 28 (SEQ ID NO:1).

TNFα can cause pro-inflammatory actions which result in tissue injury. Tumor necrosis factor (TNFα) mediates or is involved in many pathologies, such as, but not limited to, bacterial, viral or parasitic infections, chronic inflammatory diseases, autoimmune diseases, malignancies, and/or neurodegenerative diseases. Accordingly, in some embodiments, the antibodies have neutralizing and/or inhibiting activity against TNF.

In some embodiments, the antibodies are high affinity human-murine chimeric anti-TNF antibodies, and fragments or regions thereof, that have potent inhibiting and/or neutralizing activity in vivo against human TNFα. Such antibodies and chimeric antibodies can include those generated by immunization using purified recombinant hTNFα (SEQ ID NO:1) or peptide fragments thereof.

In some embodiments, the antibodies and fragments bind specifically to TNFα. In some embodiments, they can also decrease, block, abrogate, interfere, prevent and/or inhibit TNF RNA, DNA or protein synthesis, TNF release, TNF receptor signaling, membrane TNF cleavage, TNF activity, TNF production and/or synthesis in vitro, in situ and/or in vivo.

In some embodiments, the antibody is cA2. Chimeric antibody cA2 consists of the antigen binding variable region of the high-affinity neutralizing mouse anti-human TNFα IgG1 antibody, designated A2, and the constant regions of a human IgG1, kappa immunoglobulin. The human IgG1 Fc region improves allogeneic antibody effector function, increases the circulating serum half-life and decreases the immunogenicity of the antibody. The avidity and epitope specificity of the chimeric antibody cA2 is derived from the variable region of the murine antibody A2. In a particular embodiment, a source for nucleic acids encoding the variable region of the murine antibody A2 is the A2 hybridoma cell line.

In one embodiment, murine monoclonal antibody A2 is produced by a cell line designated c134A. In one embodiment, chimeric antibody cA2 is produced by a cell line designated c168A.

In some embodiments, the antibody or antigen-binding fragment can comprise at least one of the heavy chain CDR3 of cA2 and/or a light chain CDR3 of cA2. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3 of cA2. In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3 of cA2. In one embodiment, the three heavy chain CDRs and the three light chain CDRs of the antibody or antigen-binding fragment have the amino acid sequence of the corresponding CDRs of at least one of mAb A2 or cA2, as described herein.

The avidity and epitope specificity of the chimeric A2 is derived from the variable region of the murine A2. In a solid phase ELISA, cross-competition for TNF has been observed between chimeric and murine A2, indicating an identical epitope specificity of cA2 and murine A2. The specificity of cA2 for TNF-α was confirmed by its inability to neutralize the cytotoxic effects of lymphotoxin (TNF-β). Chimeric A2 neutralizes the cytotoxic effect of both natural and recombinant human TNF in a dose dependent manner. From binding assays of cA2 and recombinant human TNF, the affinity constant of cA2 was calculated to be $1.8 \times 10^9$ $M^{-1}$.

Screening methods which can be used to determine TNF neutralizing activity of a TNF neutralizing compound can include in vitro or in vivo assays. Such in vitro assays can include a TNF cytotoxicity assay, such as a radioimmuno assay, which determines a decrease in cell death by contact with TNF, such as chimpanzee or human TNF in isolated or recombinant form, wherein the concurrent presence of a TNF neutralizing compound reduces the degree or rate of cell death. The cell death can be determined using ID50 values which represent the concentration of a TNF neutralizing compound which decreases the cell death rate by 50%. For example, mAb's A2 and cA2 are found to have ID50 about 17 mg/ml+/−3 mg/ml, such as 14-20 mg/ml, or any range or value therein.

In some embodiments, the antibodies can competitively inhibit in vivo the binding to human TNFα of anti-TNFα murine mAb A2, chimeric mAb cA2, or an antibody having substantially the same specific binding characteristics, e.g., epitopic specificity, as A2 and/or cA2.

Epitopes recognized by antibodies, and fragments and regions thereof, can include 5 or more amino acids comprising at least one amino acid of each or both of the following amino acid sequences of TNF, which provide a topographical or three dimensional epitope of TNF which is recognized by, and/or binds with anti-TNF activity, a TNF antibody, or fragments thereof:

```
59-80:
Tyr-Ser-Gln-Val-Leu-Phe-Lys-Gly-Gln-Gly-
Cys-Pro-Ser-Thr-His-Val-Leu-Leu-Thr-His-
Thr-Ile (AA 59-80 of SEQ ID NO: 1);
and 87-108:
Tyr-Gln-Thr-Lys-Val-Asn-Leu-Leu-Ser-Ala-
Ile-Lys-Ser-Pro-Cys-Gln-Arg-Glu-Thr-Pro-
Glu-Gly (AA 87-108 of SEQ ID NO: 1).
```

In some embodiments, antibodies, fragments and regions of anti-TNF antibodies recognize epitopes including 5 amino acids comprising at least one amino acid from amino acids residues 87-108 or both residues 59-80 and 87-108 of hTNFα (of SEQ ID NO:1). In some embodiments, the antibodies, fragments and regions of anti-TNF antibodies do not recognize epitopes from at least one of amino acids 11-13, 37-42, 49-57 or 155-157 of hTNFα (of SEQ ID NO:1). (The putative receptor binding locus as presented by Eck and Sprang (*J. Biol. Chem.* 264(29): 17595-17605 (1989)).

In one embodiment, the antibody is an anti-hTNF chimeric antibody comprising two light chains and two heavy chains, each of the chains comprising at least part of a human constant region and at least part of a variable (V) region of non-human origin having specificity to human TNF, said antibody binding with high affinity to a inhibiting and/or neutralizing epitope of human TNF.

In one embodiment, the antibody is for use in diagnostic methods for detecting TNF in patients or animals suspected of suffering from conditions associated with abnormal TNF production. In some embodiments, the TNF antibodies are used for alleviating symptoms or pathologies involving TNF, such as, by not limited to bacterial, viral or parasitic infections, chronic inflammatory diseases, autoimmune diseases, malignancies, and/or neurodegenerative diseases.

Murine hybridomas which produce mAb specific for human TNFα or TNFβ are formed by the fusion of a mouse fusion partner cell, such as SP2/0, and spleen cells from mice immunized against purified hTNFα, recombinant hTNFα, natural or synthetic TNF peptides, including peptides including 5 or more amino acids selected from residues 59-80, and 87-108 of TNF (of SEQ ID NO:1) or other biological preparations containing TNF. To immunize the mice, a variety of different conventional protocols can be followed. For example, mice can receive primary and boosting immunizations of TNF.

The antibodies described herein can bind human TNF with a wide range of affinities ($K_D$). In one embodiment, at least one human mAb can optionally bind human TNF with high affinity. For example, a human mAb can bind human TNF with a $K_D$ equal to or less than about $10^{-7}$ M, such as but not limited to, 0.1-9.9 (or any range or value therein)× $10^{-7}, 10^{-8}, 10^{-9}, 10^{-10}, 10^{-11}, 10^{-12}, 10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

The anti-TNF antibody can comprise at least one of a heavy or light chain variable region having a defined amino acid sequence. For example, in one embodiment, the anti-TNF antibody comprises at least one of at least one light chain variable region, optionally having the amino acid sequence of SEQ ID NO:3 and/or at least one heavy chain variable region, optionally having the amino acid sequence of SEQ ID NO:5. Antibodies that bind to human TNF and that comprise a defined heavy or light chain variable region can be prepared using suitable methods, such as phage display (Katsube, Y., et al., *Int J Mol. Med*, 1(5):863-868 (1998)) or methods that employ transgenic animals, as known in the art and/or as described herein. In one embodiment, the anti-TNF antibody comprises the light chain CDRs CDR1, CDR2 and CDR3 sequences corresponding to amino acid residues 24-34, 50-56 and 89-97 of SEQ ID NO: 3, respectively, and the heavy chain CDRs HCDR1, HCDR2 and HCDR3 corresponding to amino acid residues 31-35, 50-68 and 101-109 of SEQ ID NO: 5, respectively, delineated according to Kabat.

An anti-TNF antibody can further optionally comprise a polypeptide of at least one of 70-100% of the contiguous amino acids of at least one of SEQ ID NOS:3 and 5.

In some embodiments, the amino acid sequence of an immunoglobulin chain, or portion thereof (e.g., variable region) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the corresponding chain of at least one of SEQ ID NOS:3 and 5, for example, the amino acid sequence of a light chain variable region, or the amino acid sequence of a heavy chain CDR3. Preferably, 70-100% amino acid identity (i.e., 90, 91, 92, 93, 94, 95, 96, 97, 98, 99, 100 or any range or value therein) is determined using a suitable computer algorithm, as known in the art.

Exemplary heavy chain and light chain variable regions sequences are provided in SEQ ID NOs: 3 and 5. The antibodies can comprise any number of contiguous amino acid residues from an antibody, wherein that number is selected from the group of integers consisting of from 10-100% of the number of contiguous residues in an anti-TNF antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

Antibodies also include high affinity and/or potent in vivo TNF-inhibiting and/or neutralizing antibodies, fragments or regions thereof, for both TNF immunoassays and therapy of TNF-mediated pathology. Such antibodies, fragments, or regions, will preferably have an affinity for hTNFα, expressed as Ka, of at least $10^8 M^{-1}$, more preferably, at least $10^9 M^{-1}$, such as $10^8$-$10^{10}$ $M^{-1}$, $5\times10^8 M^{-1}$, $8\times10^8 M^{-1}$, $2\times10^9 M^{-1}$, $4\times10^9 M^{-1}$, $6\times10^9 M^{-1}$, $8\times10^9 M^{-1}$, or any range or value therein.

TNF antibodies also include high affinity murine and chimeric antibodies, and fragments, regions and derivatives having potent in vivo TNFα-inhibiting and/or neutralizing activity that block TNF-induced IL-6 secretion. In some embodiments, antibodies for human therapeutic uses include high affinity murine and chimeric anti-TNFα antibodies, and fragments, regions and derivatives thereof, that block TNF-induced procoagulant activity, including blocking of TNF-induced expression of cell adhesion molecules such as ELAM-I and ICAM-I and blocking of TNF mitogenic activity, in vivo, in situ, and in vitro.

Additional examples of monoclonal anti-TNF antibodies are described in the art (see, e.g., U.S. Pat. No. 5,231,024; Möller, A. et al., *Cytokine* 2(3):162-169 (1990); U.S. application Ser. No. 07/943,852 (filed Sep. 11, 1992); Rathjen et al., International Publication No. WO 91/02078 (published Feb. 21, 1991); Rubin et al., EPO Patent Publication No. 0 218 868 (published Apr. 22, 1987); Yone et al., EPO Patent Publication No. 0 288 088 (Oct. 26, 1988); Liang, et al., *Biochem. Biophys. Res. Comm.* 137:847-854 (1986); Meager, et al., *Hybridoma* 6:305-311 (1987); Fendly et al., *Hybridoma* 6:359-369 (1987); Bringman, et al., *Hybridoma* 6:489-507 (1987); and Hirai, et al., *J. Immunol. Meth.* 96:57-62 (1987), which references are entirely incorporated herein by reference).

The results of the Examples described below demonstrate a number of important findings:

CTL removal can be controlled to less than the maximum level by control of extracellular Zn+2. For example, as demonstrated by the experimental arms in the SMF-10.1 Experiment, DOE3 Experiment, BSA Blending Experiment No. 1, and BSA Blending Experiment No. 2 described below, CTL content can be controlled within a range (e.g., 40 to 70%) by controlling the extracellular concentration of Zn+2 to a value of ≤1.2 μM. Further, as demonstrated in the DOE3 Experiment, control to a higher range of CTL content is possible with higher Zn+2 concentrations up to 6.3 μM.

Moreover, as demonstrated by the experimental arms in DOE3 Experiment, BSA Blending Experiment No. 1, and BSA Blending Experiment No. 2, within a range of extracellular Zn+2 concentration, CTL content can be further controlled by controlling the extracellular [EDTA] or [EDTA-Fe+3].

In addition, sialic acid content can be controlled to less than the maximum level by control of extracellular Zn+2. For example, as demonstrated by the experimental arms in the DOE3 Experiment, BSA Blending Experiment No. 1, and BSA Blending Experiment No. 2, sialic acid can be controlled within a range (e.g., 4 to 13%) by controlling the extracellular concentration of Zn+2 to a value of ≤1.2 μM. Moreover, as demonstrated in the DOE3 Experiment, control to a higher range of sialic acid content is possible with higher Zn+2 concentrations up to 6.3 μM.

Further, as demonstrated in the DOE3 Experiment, BSA Blending Experiment No. 1, and BSA Blending Experiment No. 2, within a range of extracellular Zn+2 concentration, sialic acid content can be further controlled by controlling the extracellular [EDTA] or [EDTA-Fe+3].

Moreover, as demonstrated in the SFM-10.3 Experiment and DOE3 Experiment, antibody production can also be controlled by controlling the extracellular concentration of $Zn+2$.

The control of $Zn+2$, $Fe+3$ and EDTA concentrations to achieve control of sialic acid addition, CTL removal and antibody production can be achieved through a variety of means, including any of the following, alone or in combination: 1) Direct addition of $Zn+2$, $Fe+3$ and EDTA to the culture medium, 2) through blending of raw materials that have $Zn+2$, $Fe+3$ or EDTA as components, 3) through treatment of raw materials to adjust the $Zn+2$, $Fe+3$ or EDTA concentrations, and/or 4) through modification of the manufacturing processes of the complex raw materials to achieve desired levels of $Zn+2$, $Fe+3$, and/or EDTA.

EXEMPLIFICATION

Materials and Methods

The experiments described herein were conducted in controlled, 3L Applikon® bioreactors, with operating conditions that have been demonstrated to provide results that are representative of the commercial infliximab process.

On the indicated day, infliximab was purified by direct product capture (DPC) using a Protein A column. It was then characterized by capillary isoelectric focusing (cIEF) or the WAX assay. Infliximab that has been purified by DPC using a Protein A column is referred to herein as a "DPC sample" or "DPC eluate."

Example 1

The cIEF Method cIEF was used to calculate the CTL content of infliximab oligosaccharides. There are three sources of charge heterogeneity evident in analysis of infliximab pre-formulated bulk (PFB): (1) CTL variability; (2) sialic acid content; and (3) deamidation. Typical infliximab eluates from early, middle and late commercial bioreactor samples exhibit CTL removal from the heavy chain of infliximab from approximately 30% to 80%, with an average CTL removal in PFB of approximately 40% to 60%. The light chain CTL is not subject to removal. CTL removal tends to be lower for early bioreactor samples and increases for middle and late bioreactor samples. Typical infliximab eluates from early and late bioreactor samples exhibit sialic acid contents of approximately 3% to 14% of the IgG oligosaccharides. Sialic acid addition is typically lower for early bioreactor samples and higher for middle and late bioreactor samples. Reversed-phase peptide mapping revealed consistent, low levels of deamidation at several deamidation sites for infliximab on the heavy chain and the light chain.

This charge heterogeneity typically leads to 4 to 6 peaks in a cIEF electropherogram. Peak 1 corresponds to infliximab containing no excess charges; that is, this peak or band contains both C-terminal lysines, no sialic acid, and no deamidation. The second, third, fourth, fifth and sixth peaks or bands contain 1, 2, 3, 4 and 5 excess charges, respectively, due to a combination of CTL removal, sialic acid addition and deamidation.

FIG. 1 is a cIEF electropherogram of a sample of infliximab, and shows the pI values for Peaks 1-6.

Figure 2:
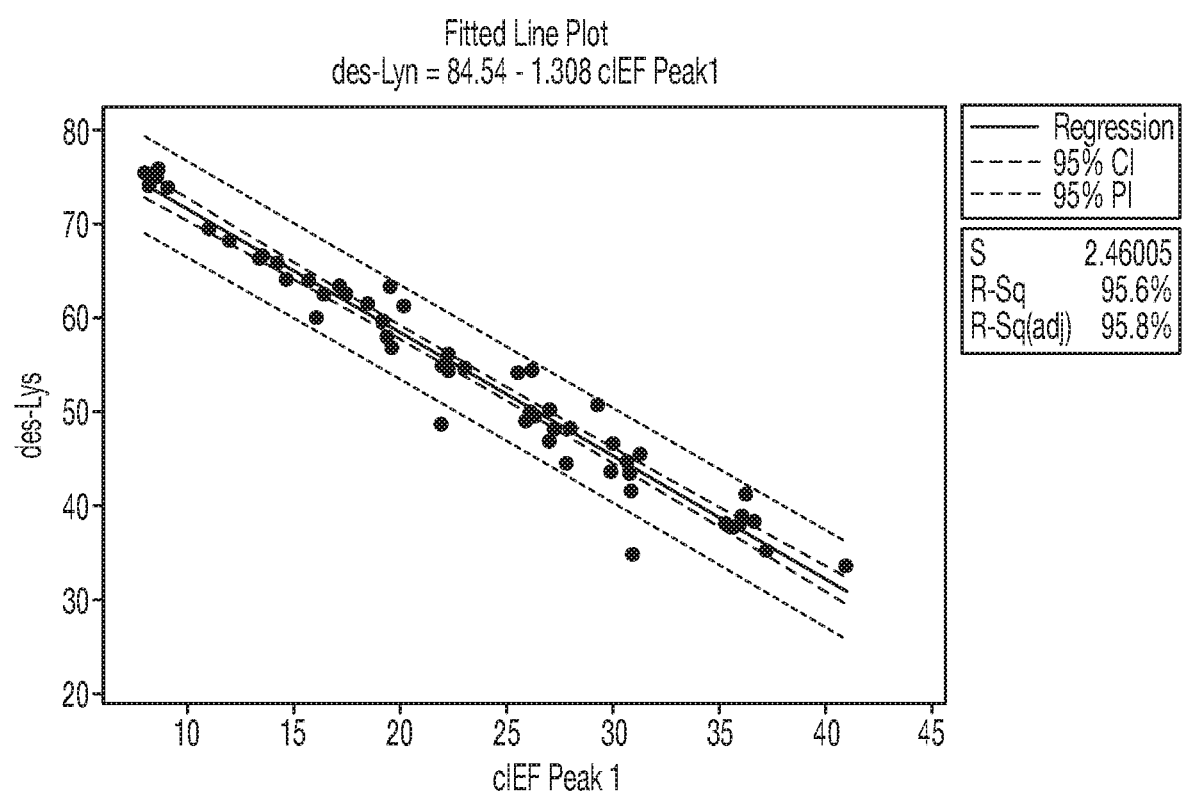
FIG. 2 is a fitted line plot of percentage of des-lysine (% lacking C-terminal lysine, abbreviated des-Lys) from reverse phase peptide mapping as a function of percentage of cIEF Peak 1, and shows the correlation between CTL content (expressed as percentage of des-Lys) and the percentage of Peak 1.

Due to the relatively high level of CTL removal, the low level of sialic acid addition, and the consistency of deamidation, the relative percentage of Peak 1 is highly correlated with CTL removal. FIG. 2 is a fitted line plot of percentage of des-lysine (des-Lys) as a function of percentage of Peak 1, and shows the correlation between CTL content (expressed as percentage of des-Lys) and the percentage of Peak 1 across a range of experimental conditions. The correlation depicted in FIG. 2 was created from infliximab samples for which percentage of des-Lys was determined by peptide mapping and percentage of Peak 1 was determined by cIEF.

CTL content is expressed herein as the percentage of heavy chains possessing a C-terminal lysine and can be calculated using the following equation: CTL content (%)= (number of heavy chains possessing a CTL)/(total number of heavy chains)×100. CTL removal is expressed herein as the percentage of heavy chains lacking a C-terminal lysine (des-Lys). So, "80% Des-Lys" is equivalent to 20% CTL content. The correlation between percentage of des-Lysine and percentage of Peak 1 (as measured by cIEF) holds for infliximab samples that exhibit typical percentages of CTL removal, sialic acid addition, and deamidation. This correlation would, therefore, apply to experiments described herein because: (1) sialic acid addition by WAX has been determined for many of DPC samples from these experiments, and the results indicate that sialic acid remained in the typical range of 3% for early bioreactor samples to approximately 14% for late bioreactor samples (that is, the percentage of sialic acid remained in the range of the data employed to generate the correlation of FIG. 1); and (2) it is reasonable to assume that the percentages of deamidation remained low and consistent, as was the case for the experimental samples employed to generate the correlation of FIG. 1.

CTL removal in these experiments ranged from the typical values of 30-60%, to higher values. Under these conditions, CTL removal would continue to be the dominant determinant of percentage of Peak 1.

Example 2

The Wax Assay

The WAX assay was used to determine the sialic acid content and the galactose content of infliximab oligosaccharides. In the assay, N-linked oligosaccharides are released from the IgG using PNGase F, then are derivatized using a solution of anthranilic acid and sodium cyanoborohydride. Samples are purified using 0.45-micron nylon ACRODISC® filters, and analyzed on an Agilent 1100 HPLC with a fluorescence detector. Peak identities are resolved using commercially available N-glycan standards.

In the WAX assay described herein, Component 5A is the percentage of infliximab oligosaccharides containing sialic acid. Component 1 is highly correlated with the percentage of infliximab oligosaccharides that lack galactose. Therefore, (100−percentage of Component 1) represents a reasonable estimate of the percentage of infliximab oligosaccharides that contain galactose.

In the heavy chain of infliximab, one asparagine (Asn) residue is glycosylated with an oligosaccharide, which can contain, for example, one or two galactose residues and one or two sialic acid residues. Galactose content of infliximab is expressed herein as the percentage of oligosaccharides containing galactose, and can be calculated using the following equation: galactose content (%)=(number of oligosaccharides containing a galactose)/(total number of oligosaccharides)×100. This equation applies independently of the number of galactose units in the oligosaccharide. In other words, regardless of whether there are, for example, one or two galactose residues in the oligosaccharide, the oligosaccharide is only counted once for the purposes of calculating galactose content.

Sialic acid content of infliximab is expressed herein as the percentage of oligosaccharides containing sialic acid, and can be calculated using the following equation: sialic acid content (%)=(number of oligosaccharides containing a sialic acid)/(total number of oligosaccharides)×100. This equation applies independently of the number of sialic acid residues in the oligosaccharide. In other words, regardless of whether there are, for example, one or two sialic acid residues in the oligosaccharide, the oligosaccharide is only counted once for the purposes of calculating sialic acid content.

Typically, both heavy chains of infliximab are glycosylated. However, in some circumstances, some of the heavy chains remain aglycosylated. For example, in some embodiments, approximately 94% of infliximab molecules are glycosylated on both chains, approximately 6% of infliximab molecules are hemi-glycosylated, and approximately 0.1% of infliximab molecules are fully aglycosylated.

The ratio of sialic acid to galactose is calculated from the molar ratio of sialic acid to galactose in the oligosaccharides of infliximab.

Example 3

Harvest Hold Studies

Two studies were conducted in which cell-free infliximab harvest was held for extended periods. The purpose of these studies was to understand if CTL removal could occur extracellularly (i.e., post-secretion).

Sialic acid is known to be added to glycoproteins intracellularly, prior to secretion. However, extracellular removal of sialic acid from secreted recombinant glycoproteins has been reported for chinese hamster ovary (CHO) cell cultures. For CHO cells, the sialidase is released into the extracellular medium from lysed cells. So, a second purpose of these harvest hold studies was to clarify whether there is extracellular removal of sialic acid in the cell-free harvest for the infliximab process.

A harvest hold study using harvest from manufacturing scale bioreactors demonstrated that holding harvest under varying conditions (clarified, cell-free harvest held for 30 days at 2 to 14° C.; unclarified harvest held for 14 days at 2-8° C.) and varying bioreactor ages had no impact on the cIEF gel profile of infliximab.

To buttress these results, another harvest hold study was conducted. The infliximab cell-free harvest was collected from two bioreactors. For each bioreactor, one part of the harvest was immediately purified by Protein A chromatography to produce DPC eluate. The other part of the harvest was stored for 7 days at temperatures between 10-14° C. (a typical storage temperature), before processing to a DPC eluate. The temperature of harvest on hold was monitored by a probe in a refrigerator and controlled by manual adjustment. The four DPC eluate samples were then analyzed by cIEF for any evidence of charge distribution change that would indicate CTL or sialic acid removal in the harvest.

This hold study revealed no significant difference in the cIEF patterns for DPC eluates made immediately from harvest or from harvest held for 7 days at a temperature of 10-12° C. prior to Protein A purification.

The harvest hold studies demonstrate that the removal of CTL from the heavy chain of infliximab is likely occurring intracellularly. Likewise, the sialic acid content of infliximab oligosaccharides is determined intracellularly.

Example 4

The SFM-10.1 Experiment

The term SFM-10.1 corresponds to infliximab SFM-10 medium lacking BSA and CM2 (Part B) liquid (including zinc-containing insulin). The purpose of the SFM-10.1 Experiment was to probe the impact of $Zn^{+2}$ supplementation on the production of infliximab.

The four experimental conditions represent SFM-10.1 medium supplemented with zinc sulfate heptahydrate, which was added in an amount sufficient to add 0.25, 0.5, 1.0 or 2.0 µM $Zn^{+2}$ to the final medium concentration. The total $Zn^{+2}$ concentration in each experiment was the sum of this supplementation plus the $Zn^{+2}$ contributed from PRIMATONE® (available from Kerry Ingredients and Flavours, Beloit, Wis.), which was determined to be 0.49 µM (based on metals analysis). Thus, the total zinc concentrations in these four bioreactors are reasonably estimated as 0.74, 1.0, 1.5 and 2.5 µM. The $Fe^{+3}$ concentration in these bioreactors was 5.8 µM, based on metals analysis of the PRIMATONE® lot employed. The EDTA concentration is estimated to be 2 µM, contributed from transferrin. EDTA has a much stronger affinity for Fe+3 than for Zn+2 and other divalent cations. Therefore, the computation of [EDTA-Fe+3] may represent the concentration of EDTA that is available to chelate Zn+2. Therefore, in this first set of experiments, it can be expected that there is no free EDTA available to bind extracellular $Zn^{2+}$.

TABLE 1

Concentrations of Zn + 2, Fe + 3, EDTA, and [EDTA − Fe + 3] in the four bioreactors of the SFM-10.1 Experiment (concentrations are in µM).

| Bioreactor Arm | [Zn + 2] | [Fe + 3] | [EDTA] | [EDTA − Fe] |
|---|---|---|---|---|
| Zn: 0.74 µM | 0.74 | 5.8 | 2 | −3.8 |
| Zn: 1.0 µM | 0.99 | 5.8 | 2 | −3.8 |
| Zn: 1.5 µM | 1.5 | 5.8 | 2 | −3.8 |
| Zn: 2.5 µM | 2.5 | 5.8 | 2 | −3.8 |

Figure 3:
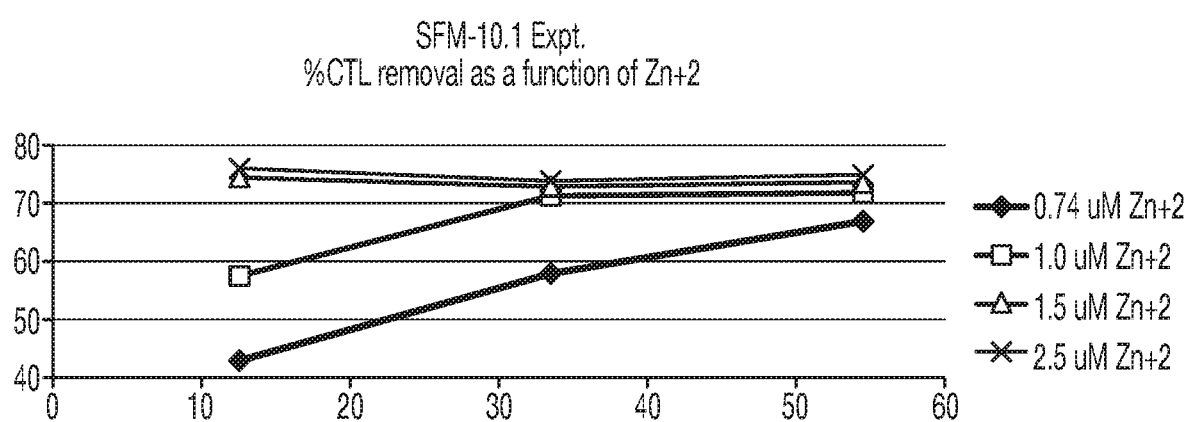
FIG. 3 is a graph of CTL removal (expressed as percentage of des-Lys and computed using the cIEF method from Peak 1 data) as a function of bioreactor age, and shows the effect of varying $Zn^{+2}$ concentrations on CTL removal. Y-axis: % des1-Lys; X-axis: bioreactor age in days.

FIG. 3 is a graph of CTL removal (expressed as percentage of des-Lys and computed using the cIEF method from the Peak 1 data) as a function of bioreactor age, and shows the effect of varying $Zn^{+2}$ concentrations on CTL removal. The bioreactors with total Zn+2 concentrations of approximately 1.5 and 2.5 µM exhibited 70% to 80% CTL removal at all time points. There is no change in charge distribution as a function of bioreactor age, as all time points (early, middle and late bioreactor samples) have high CTL removal. The bioreactor with a Zn+2 concentration of 1.0 µM exhibited 60% CTL removal early in the study and approximately 70% removal at the middle and late sample points. The bioreactor with a Zn+2 concentration of approximately 0.74 µM exhibited increasing CTL removal as a function of bioreactor age.

Figure 4:
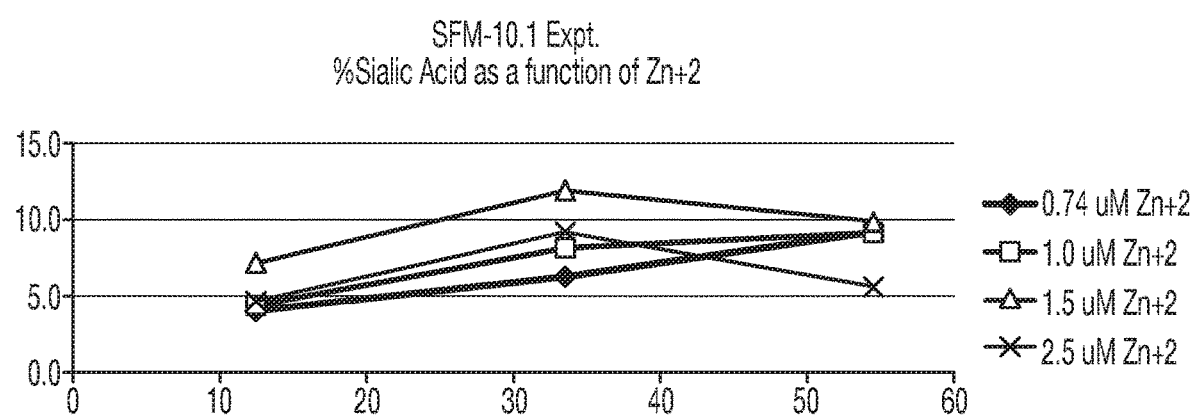
FIG. 4 is a graph of percentage of infliximab oligosaccharides with sialic acid, as determined by the WAX method, as a function of bioreactor age, and shows the effect of varying $Zn^{+2}$ concentrations on the percentage of sialic acid. Y-axis: % sialic acid; X-axis: bioreactor age in days.

FIG. 4 is a graph of percentage of infliximab oligosaccharides with sialic acid, as determined by the WAX method, as a function of bioreactor age, and shows the effect of varying $Zn^{+2}$ concentrations on the percentage of sialic acid. FIG. 4 shows there was no clear trend in sialic acid addition as a function of Zn+2 concentration in this experiment.

It is not known whether this lack of impact represents a true insensitivity of sialic acid content to extracellular $Zn^{+2}$ concentration in the context of SFM-10.1 medium, whether it is a reflection of experimental noise given the small number of bioreactors, or whether there could have been a procedural issue with experimental implementation.

Figure 5:
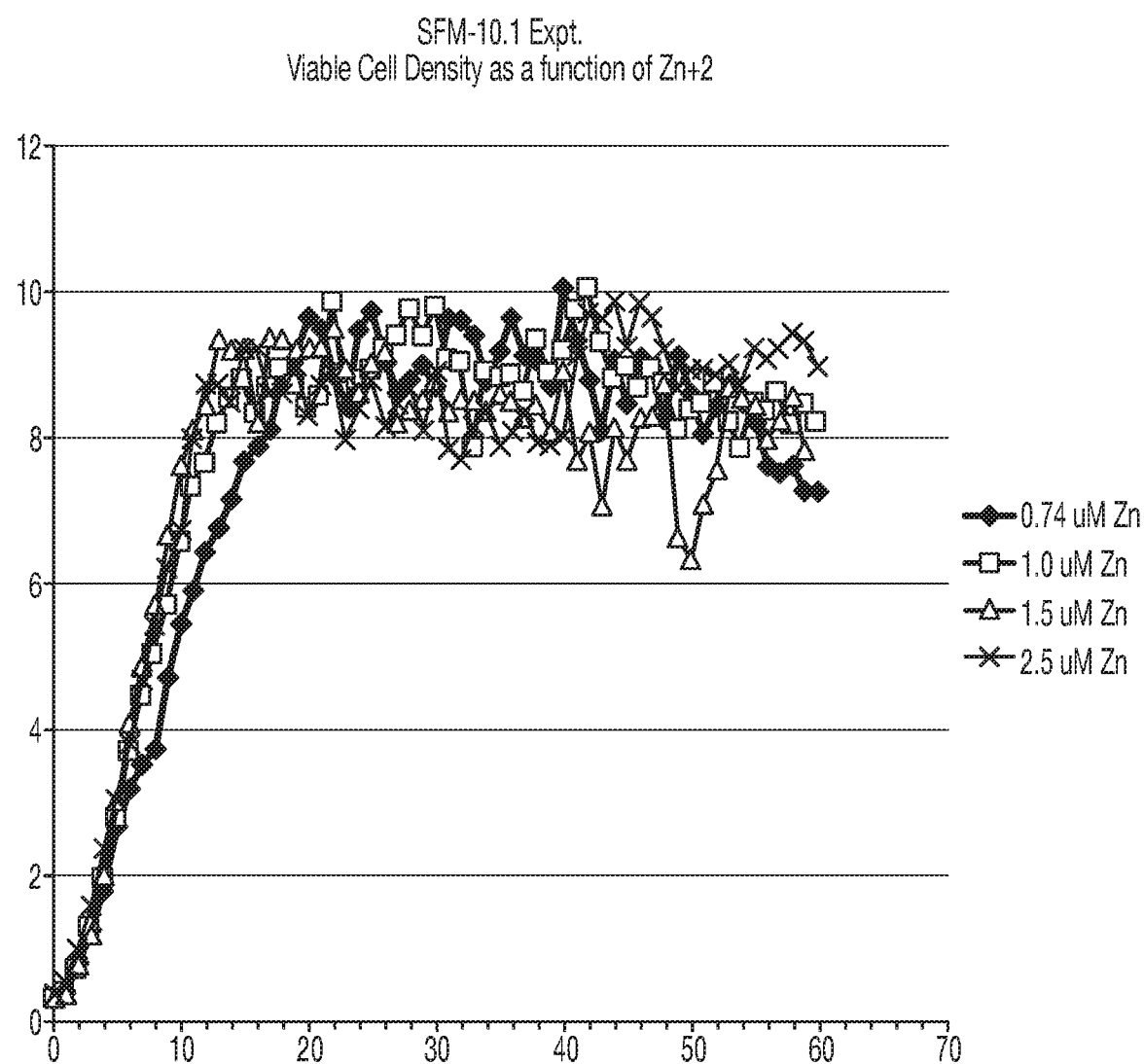
FIG. 5 is a graph of viable cell density as a function of bioreactor age, and shows the effect of varying $Zn^{+2}$ concentrations on the viable cell density. Y-axis: viable cell density (millions of viable cells/mL); X-axis: bioreactor age in days.
Figure 6:
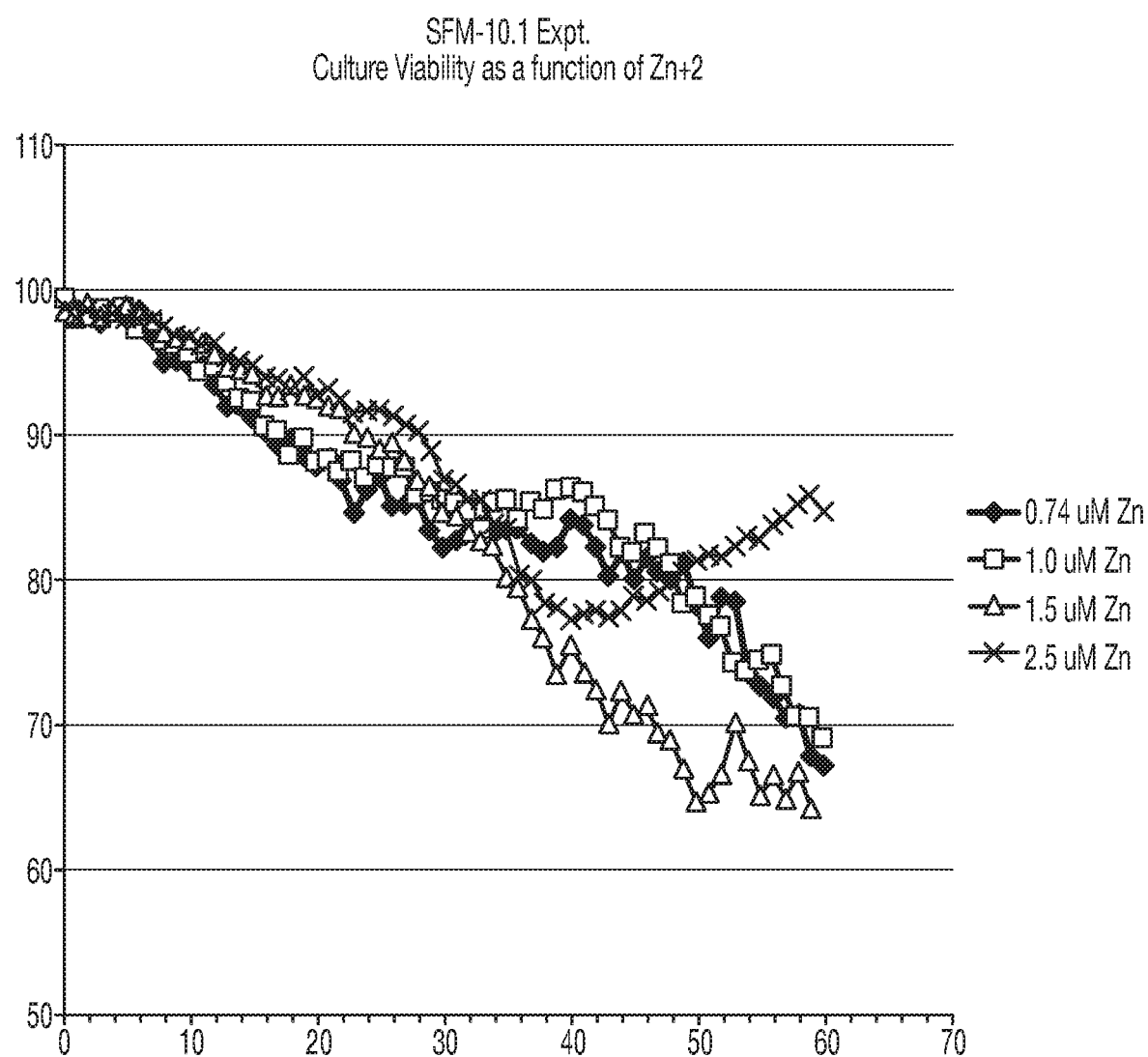
FIG. 6 is a graph of percentage of viable cells as a function of bioreactor age, and shows the effect of varying $Zn^{+2}$ concentrations on the culture viability. Y-axis: % viable cells, X-axis: bioreactor age in days.
Figure 7:
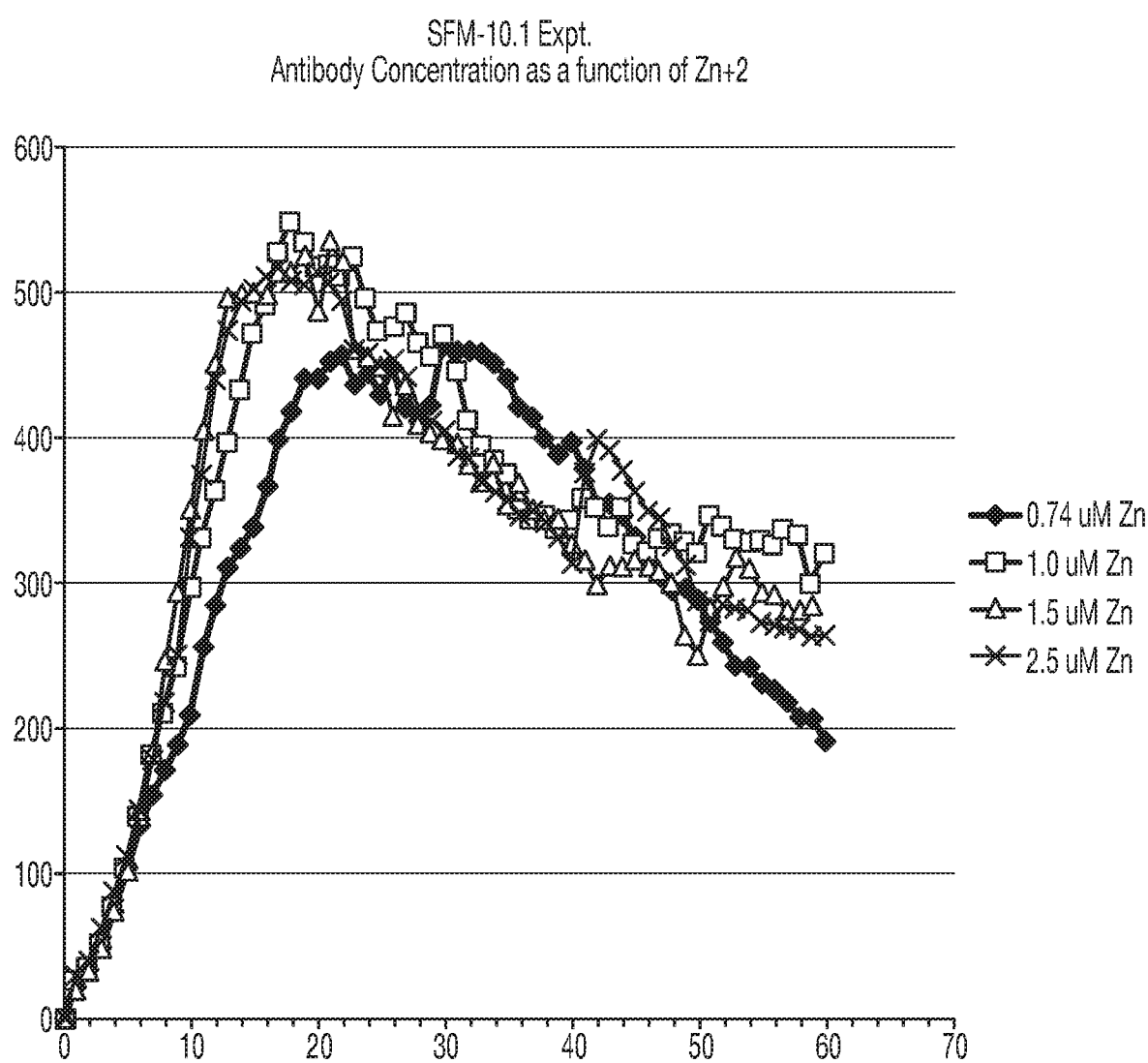
FIG. 7 is a graph of infliximab concentration as a function of bioreactor age, and shows the effect of varying $Zn^{+2}$ concentrations on the concentration of infliximab. The y-axis concentration mg/mL as indicated contains a typographical error. The concentration is mg/L. Y-axis: infliximab concentration (mg/L), X-axis: bioreactor age in days.

FIGS. 5-7 are graphs of the viable cell density, culture viability and infliximab concentration, respectively, as a function of time, and show the effect of varying concentrations of $Zn^{+2}$ in the SFM-10.1 experiment. The results in the period prior to reaching target cell density at approximately Day 15-20 are the most revealing, as this represents a period in which every bioreactor is operated consistently. After reaching target cell density, cells are removed from the cultures daily in an attempt to maintain the target cell concentration, and variations in this removal procedure can cause fluctuations in cell density, culture viability and antibody concentration.

In the SFM-10.1 experiment, the bioreactor with 0.74 μM $Zn^{+2}$ had lower cell growth rate, lower culture viability and a lower antibody concentration prior to reaching target cell density than the bioreactors containing 1.5 and 2.5 μM $Zn^{+2}$. The bioreactor with 1.0 μM $Zn^{+2}$ exhibited performance in each case that was intermediate between the bioreactors with 0.74 μM and the bioreactors with 1.5 or 2.5 μM $Zn^{+2}$.

The conditions of this experiment were favorable to $Zn^{+2}$ accumulation by the SP2/0 cells. The [EDTA-Fe+3] is less than zero, indicating that all EDTA is chelated to $Fe^{+3}$ and not available to chelate $Zn^{+2}$ in the extracellular medium. Furthermore, another potential chelator, BSA, was absent from the medium.

In spite of these favorable conditions for $Zn^{+2}$ accumulation, the experimental results indicate an impact of extracellular $Zn^{+2}$ concentrations of 0.74 and 1.0 μM on CTL removal, initial cell growth, culture viability, and antibody concentration, particularly in the first 20 days of the culture. The results do not show a clear impact of $Zn^{+2}$ on sialic acid addition under the conditions of this experiment.

Although not wishing to be bound by any particular theory, these results are consistent with the following hypotheses:

The SP2/0 cells must accumulate intracellular $Zn^{+2}$ to support intracellular processes associated with enzymes having $Zn^{+2}$ cofactor requirements. This includes enzymes responsible for CTL removal, cell growth, cell division, and antibody production.

$Zn^{+2}$ concentrations on the order of 0.74 to 1.0 μM do not provide sufficient extracellular $Zn^{+2}$ to adequately supply these $Zn^{+2}$-requiring intracellular processes during the initial stages of the production bioreactor process.

The effect is most pronounced in the first 20 days of culture. This is the period where the amount of intracellular $Zn^{+2}$ per cell is being continuously reduced due to cell division. That is, every time a cell divides, the accumulated $Zn^{+2}$ is split between the daughter cells. At 0.74 to 1.0 μM of extracellular $Zn^{+2}$, cellular incorporation of $Zn^{+2}$ cannot keep up with cellular reduction of $Zn^{+2}$ due to cell doubling. Thus, the cells are deficient in $Zn^{+2}$ and exhibit non-optimal cell growth, culture viability and antibody productivity.

After about Day 20, the cells are close to their target cell density for perfusion culture, and cell division slows. From that point onward, the rate of intracellular $Zn^{+2}$ reduction due to cell division slows, and cellular incorporation is adequate to assure increasing $Zn^{+2}$ accumulation per cell over time. Under these conditions and after Day 20, the cells gradually increase their intracellular stores of $Zn^{+2}$.

For the bioreactor with 0.74 μM $Zn^{+2}$, the pattern of $Zn^{+2}$ accumulation as a function of bioreactor age is responsible for the observed changes in cIEF pattern as a function of bioreactor age. That is, CTL removal is at a minimum at Day 20, the point in the culture when the intracellular enzyme carboxypeptidase will be most deficient in the required $Zn^{+2}$ cofactor. After cell division slows and after Day 20, CTL removal increases due to increasing $Zn^{+2}$ accumulation, leading to increased carboxypeptidase function.

For the experimental arms with 1.5 μM and 2.5 μM $Zn^{+2}$, the extracellular $Zn^{+2}$ concentration is sufficiently high that the cellular enzymes do not experience $Zn^{+2}$ deficiency at any point in the culture. Thus, CTL removal is at a high rate from Day 20 through Day 60. Likewise, cell growth, culture viability and antibody production proceed at high rates as a function of culture day.

Example 5

The DOE3 Experiment

Following the leads generated in the SFM-10.1 experiment, a more detailed experiment was performed using commercial infliximab SFM-10 medium to probe the impacts of extracellular $Zn^{+2}$, EDTA, and $Fe^{+3}$ concentration on CTL removal, sialic acid addition, cell growth, culture viability and antibody production.

It was reasoned that extracellular binding of $Zn^{+2}$ to EDTA could hypothetically inhibit intracellular accumulation of $Zn^{+2}$. Since extracellular $Fe^{+3}$ would have a much higher binding affinity to EDTA than $Zn^{+2}$, it was reasoned that the key factor in determining intracellular accumulation of $Zn^{+2}$ could be [EDTA-Fe+3].

The DOE3 experiment included twelve bioreactors. The medium for this experiment was commercial SFM-10 medium. The chosen lots of PRIMATONE®, insulin, transferrin and BSA created basal levels of 0.76 μM $Zn^{+2}$, 5.9 μM EDTA, and 0.9 μM $Fe^{+3}$. A matrix of experimental conditions was created by supplementation of $Zn^{+2}$, EDTA, and/or $Fe^{+3}$, as indicated in Table 2.

TABLE 2

Concentrations of Zn + 2, Fe + 3, EDTA, and [EDTA − Fe + 3] in the Twelve Bioreactors of the DOE3 Experiment (concentrations are in μM).

| Bioreactor Arm[a] | [Zn + 2] | [Fe + 3] | [EDTA] | [EDTA − Fe] |
|---|---|---|---|---|
| "Fe: 1 Zn: 1 EDTA: 6" | 0.76 | 0.90 | 5.9 | 5.0 |
| [b]"Fe: 5 Zn: 1 EDTA: 10" | 0.76 | 5.4 | 10.4 | 5.0 |
| "Fe: 1 Zn: 1 EDTA: 12" | 0.76 | 0.90 | 11.6 | 10.7 |
| "Fe: 5 Zn: 1 EDTA: 16" | 0.76 | 5.4 | 16.1 | 10.7 |
| "Fe: 1 Zn: 1 EDTA: 24" | 0.76 | 0.90 | 23.6 | 22.7 |
| "Fe: 5 Zn: 1 EDTA: 28" | 0.76 | 5.4 | 28.1 | 22.7 |
| "Fe: 3 Zn: 2 EDTA: 9" | 1.7 | 3.2 | 9.0 | 5.8 |
| "Fe: 3 Zn: 2 EDTA: 14(A)" | 1.7 | 3.2 | 13.8 | 10.6 |

TABLE 2-continued

Concentrations of Zn + 2, Fe + 3, EDTA, and
[EDTA − Fe + 3] in the Twelve Bioreactors of the
DOE3 Experiment (concentrations are in μM).

| Bioreactor Arm[a] | [Zn + 2] | [Fe + 3] | [EDTA] | [EDTA − Fe] |
|---|---|---|---|---|
| "Fe: 3 Zn: 2 EDTA: 14(B)" | 1.7 | 3.2 | 13.8 | 10.6 |
| "Fe: 3 Zn: 2 EDTA: 14(C)" | 1.7 | 3.2 | 13.8 | 10.6 |
| "Fe: 3 Zn: 2 EDTA: 27" | 1.7 | 3.2 | 26.8 | 23.6 |
| "Fe: 5 Zn: 2 EDTA: 6" | 1.7 | 5.4 | 5.9 | 0.53 |

[a]Bioreactor arms are designated by the approximate concentrations of Fe + 3, Zn + 2 and EDTA (in μM).
[b]Bioreactor "Fe: 5 Zn: 1 EDTA: 10" (M12COO3) experienced a significant deviation in the experimental protocol. Prior to Day 13, the Zn + 2 concentration of the medium was 6.3 μM. On Day 13, the medium was adjusted to the target value of 0.76 μM. That is, this bioreactor was subjected to a very high Zn + 2 concentration in the early period of cell culture.

In the DOE3 experiment, the total Zn+2 concentration ranged from 0.76 to 1.7 μM, the Fe+3 concentration ranged from 0.90 to 5.4 μM, the EDTA concentration ranged from 5.9 to 26.8 μM, and [EDTA-Fe+3] ranged from 0.53 to 23.6 μM.

In the analysis of DOE3 experimental results, the impact of Zn+2 was dominant over the impacts of extracellular [EDTA] and [EDTA-Fe+3]. Thus, it is reasonable in the following presentation of results to group the DOE3 experimental results as a function of the [Zn+2] in each bioreactor; six bioreactors were targeted for [Zn+2] of 0.76 μM and six bioreactors were targeted for [Zn+2] of 1.7 μM.

Figure 8A:
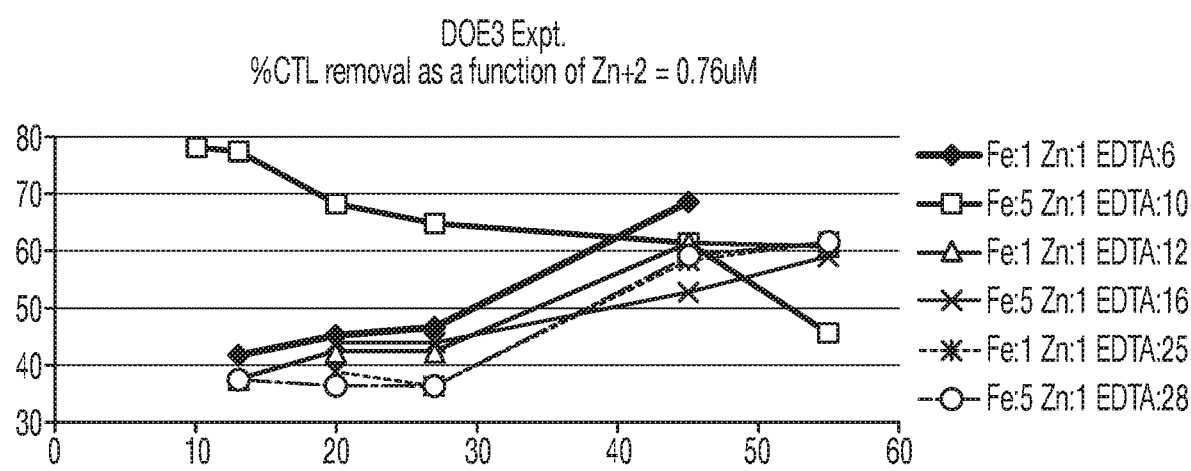
FIG. 8A is a graph of CTL removal (expressed as percentage of des-Lys and computed using the cIEF method from Peak 1 data) as a function of bioreactor age, and shows the effect of varying EDTA concentrations on CTL removal in the presence of 0.76 µM $Zn^{+2}$ (the initial concentration of $Zn^{+2}$ in the bioreactor corresponding to the label "Fe:5 Zn:1 EDTA:10" was 6.3 µM, rather than 0.76 µM; the targeted concentration of 0.76 µM $Zn^{+2}$ was implemented from Day 13 until the end of the experiment). Y-axis: % des1-Lys; X-axis: bioreactor age in days.
Figure 8B:
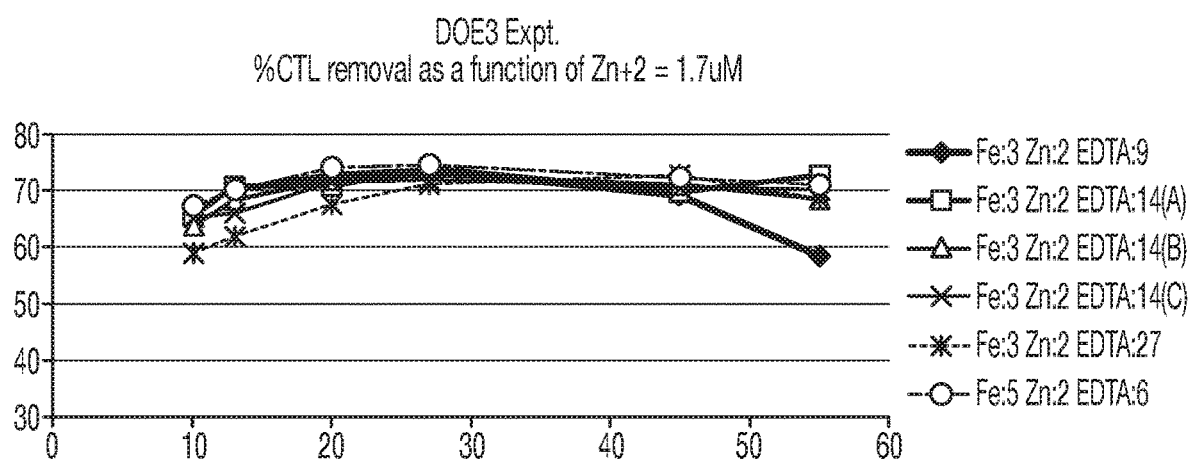
FIG. 8B is a graph of CTL removal (expressed as percentage of des-Lys and computed using the cIEF method from Peak 1 data) as a function of bioreactor age, and shows the effect of varying EDTA concentrations on CTL removal in the presence of 1.7 µM $Zn^{+2}$. Y-axis: % des1-Lys; X-axis: bioreactor age in days.

FIG. 8A is a graph of CTL removal (expressed as percentage of des-Lys and computed using the cIEF method from Peak 1 data) as a function of bioreactor age, and shows the effect of varying EDTA concentrations on CTL removal in the presence of 0.76 μM $Zn^{+2}$ (the initial concentration of $Zn^{+2}$ in the bioreactor corresponding to the label "Fe:5 Zn:1 EDTA:10" was 6.3 μM, rather than 0.76 μM; the targeted concentration of 0.76 μM $Zn^{+2}$ was implemented from Day 13 until the end of the experiment). FIG. 8B is a graph of CTL removal (expressed as percentage of des-Lys and computed using the cIEF method from Peak 1 data) as a function of bioreactor age, and shows the effect of varying EDTA concentrations on CTL removal in the presence of 1.7 μM $Zn^{+2}$. As in the SFM-10.1 experiment, the bioreactors from the DOE3 experiment exhibited a strong relationship between percentage of CTL removal and Zn+2 concentration.

The bioreactors with 0.76 μM Zn+2 exhibited significantly lower percent CTL removal than the bioreactors with 1.7 μM Zn+2. The bioreactors with the higher Zn+2 concentration exhibited 60 to 75% CTL removal at early, middle and late periods of culture. The bioreactors with a lower concentration of Zn+2 exhibited 40% CTL removal at Days 10-20, and the CTL removal gradually rose as a function of culture day, approaching 60% CTL removal at the end of the cultures. These results are consistent with the effect of Zn+2 concentration observed in the SFM-10.1 experiment.

As noted previously, the bioreactor labeled "Fe:5, Zn:1, EDTA:10" experienced a very high Zn+2 concentration of 6.3 μM prior to Day 13, which correlates to 80% CTL removal in the early stages of culture, the highest CTL removal achieved in this study. The percentage of CTL removal in this bioreactor gradually dropped following the correction of its medium concentration to 0.76 Zn+2 on Day 13. With a perfusion rate of approximately 0.7 culture volumes per day, the Zn+2 concentration in the production bioreactor would have fallen to 0.76 μM within 10 days or less. Yet, the percentage of CTL removal remained much higher in this bioreactor than in its sister bioreactors at 0.76 μM Zn+2. That is, the cells seem to have a mechanism that "remembers" past Zn+2 exposure.

Although not wishing to be bound by any particular theory, it is hypothesized that this cellular "memory" relates to the accumulation of Zn+2 inside the cells. This accumulated Zn+2 cannot be reversed by a sudden reduction in extracellular Zn+2 concentration. It is likely that the accumulated Zn+2 per cell can only be reduced by subsequent cell division, in which accumulated Zn+2 is divided between daughter cells. Under the conditions of the DOE3 experiment, the extent of cell division was limited after the cells reached the target cell density on approximately Day 15-20.

The CTL removal at Days 10 and 13 for bioreactor "Fe:5, Zn:1, EDTA:10" is approximately 80%, higher than for the bioreactors at 1.7 μM Zn+2. This suggests that under the experimental conditions of the DOE3 experiment, 1.7 μM Zn+2 is not sufficient to saturate the cells' need for Zn+2.

As noted above, the results of the DOE3 experiment correlated strongly with Zn+2 concentration. However, within the results at a given Zn+2 concentration, there is evidence of an effect of EDTA (or EDTA-Fe+3) on CTL removal. Among the bioreactors with 0.7 μM Zn+2, the two bioreactors with the lowest CTL removal at Days 13, 20, and 28 had the highest [EDTA] and [EDTA-Fe+3] (bioreactors "Fe:1 Zn:1 EDTA:25" and "Fe:5 Zn:1 EDTA:28") (FIG. 8A). Conversely, the bioreactor with the lowest [EDTA] and [EDTA-Fe+3] had the highest CTL removal ("Fe:1 Zn:1 EDTA:6").

Likewise, among the bioreactors with 1.7 μM Zn+2, the bioreactor with the lowest CTL removal at Days 13, 20, and 28 had the highest [EDTA] and [EDTA-Fe+3] ("Fe:3 Zn:2 EDTA:27") (FIG. 8B).

Figure 9A:
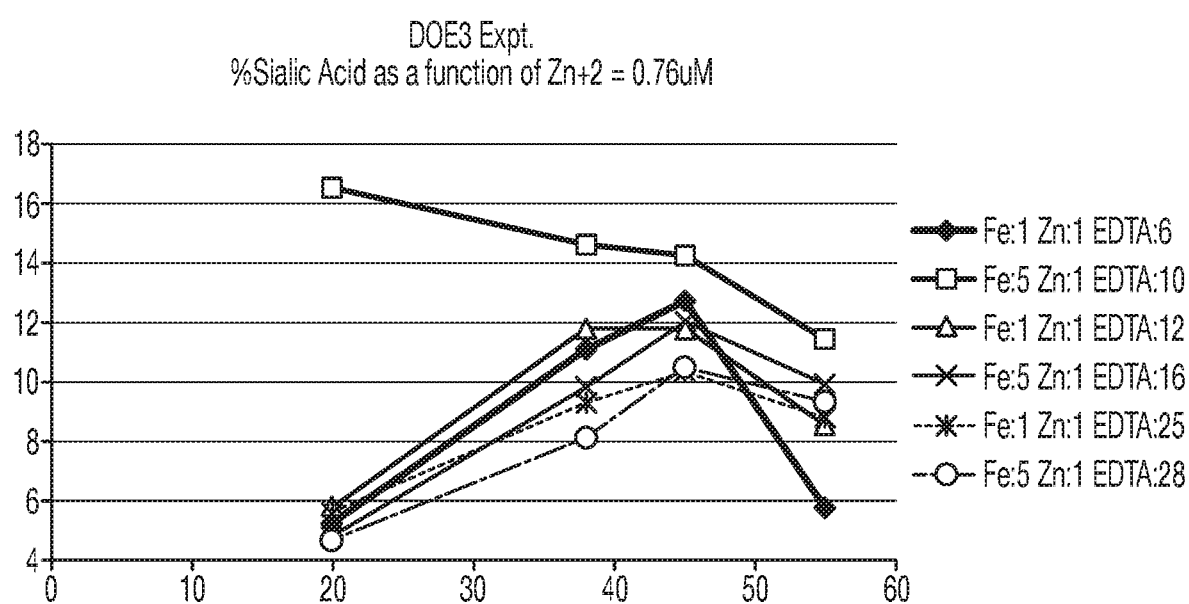
FIG. 9A is a graph of percentage of infliximab oligosaccharides with sialic acid, as determined by the WAX method, as a function of bioreactor age, and shows the effect of varying EDTA concentrations on the percentage of sialic acid in the presence of 0.76 µM $Zn^{+2}$ (the initial concentration of $Zn^{+2}$ in the bioreactor corresponding to the label "Fe:5 Zn:1 EDTA:10" was 6.3 µM, rather than 0.76 µM; the targeted concentration of 0.76 µM $Zn^{+2}$ was implemented from Day 13 until the end of the experiment). Y-axis: % sialic acid; X-axis: bioreactor age in days.
Figure 9B:
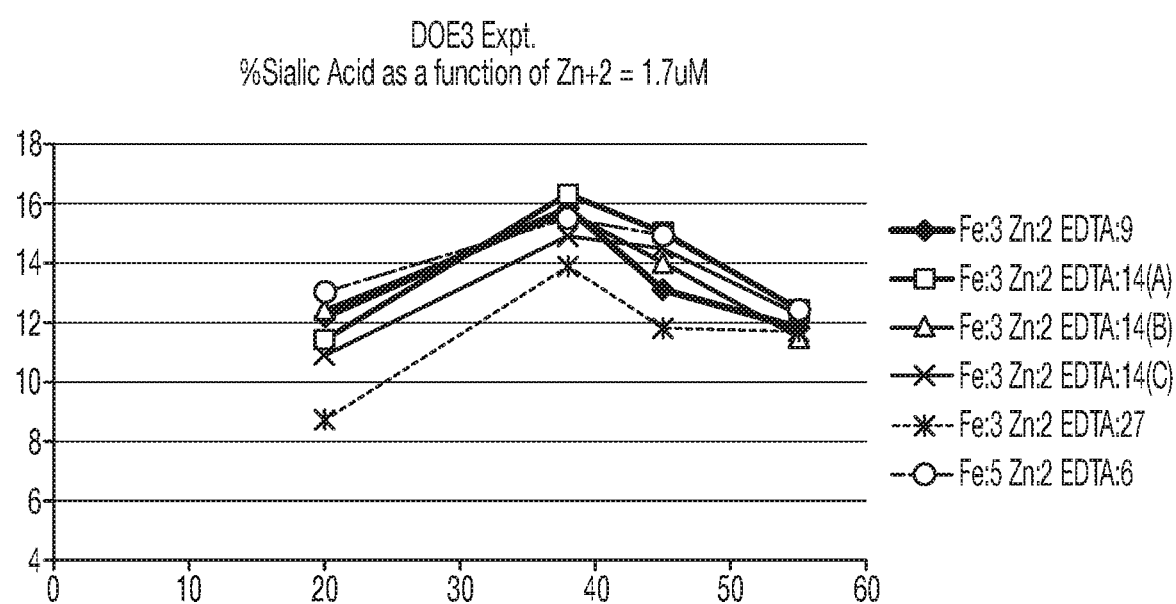
FIG. 9B is a graph of percentage of infliximab oligosaccharides with sialic acid, as determined by the WAX method, as a function of bioreactor age, and shows the effect of varying EDTA concentrations on sialic acid content in the presence of 1.7 µM $Zn^{+2}$. Y-axis: % sialic acid; X-axis: bioreactor age in days.

FIGS. 9A and 9B show that there is a significant difference in sialic acid content as a function of [Zn+2] in the DOE3 experiment. At days 10-20, there is significantly higher sialic acid content in the bioreactors with 1.7 μM Zn+2 (FIG. 9B) than in the bioreactors at 0.76 μM (FIG. 9A). For "late" bioreactor samples, the difference in sialic acid content narrows, but is still higher at 1.7 μM Zn+2 than at 0.76 μM Zn+2.

FIGS. 9A and 9B are also evidence of the cellular "Zn+2 memory" discussed above. In bioreactor "Fe:5, Zn:1, EDTA:10", the sialic acid content was very high at the earliest time point for this bioreactor, and remained much higher than its sister bioreactors having 0.76 μM Zn+2 throughout the culture period, in spite of the fact that the extracellular Zn+2 concentrations in all of the bioreactors would have been the same by approximately Day 20.

The sialic acid content at Days 10 and 13 for bioreactor "Fe:5, Zn:1, EDTA:10" is approximately 18%, significantly higher than for the bioreactors having 1.7 μM Zn+2. This suggests that, under the experimental conditions of the DOE3 experiment, 1.7 μM Zn+2 is not sufficient to saturate the cells need for Zn+2 to support sialic acid addition.

As noted above, the results of the DOE3 experiment correlated strongly with Zn+2 concentration. However, within the results at a given Zn+2 concentration, there is evidence of an effect of [EDTA] (or [EDTA-Fe+3]) on sialic acid addition. FIG. 9A shows that among the bioreactors with 0.7 μM Zn+2, the sialic acid content at Day 38 increases as [EDTA] decreases. FIG. 9B shows that at Days 20 and 38, sialic acid content increases as [EDTA] decreases.

Figure 10:
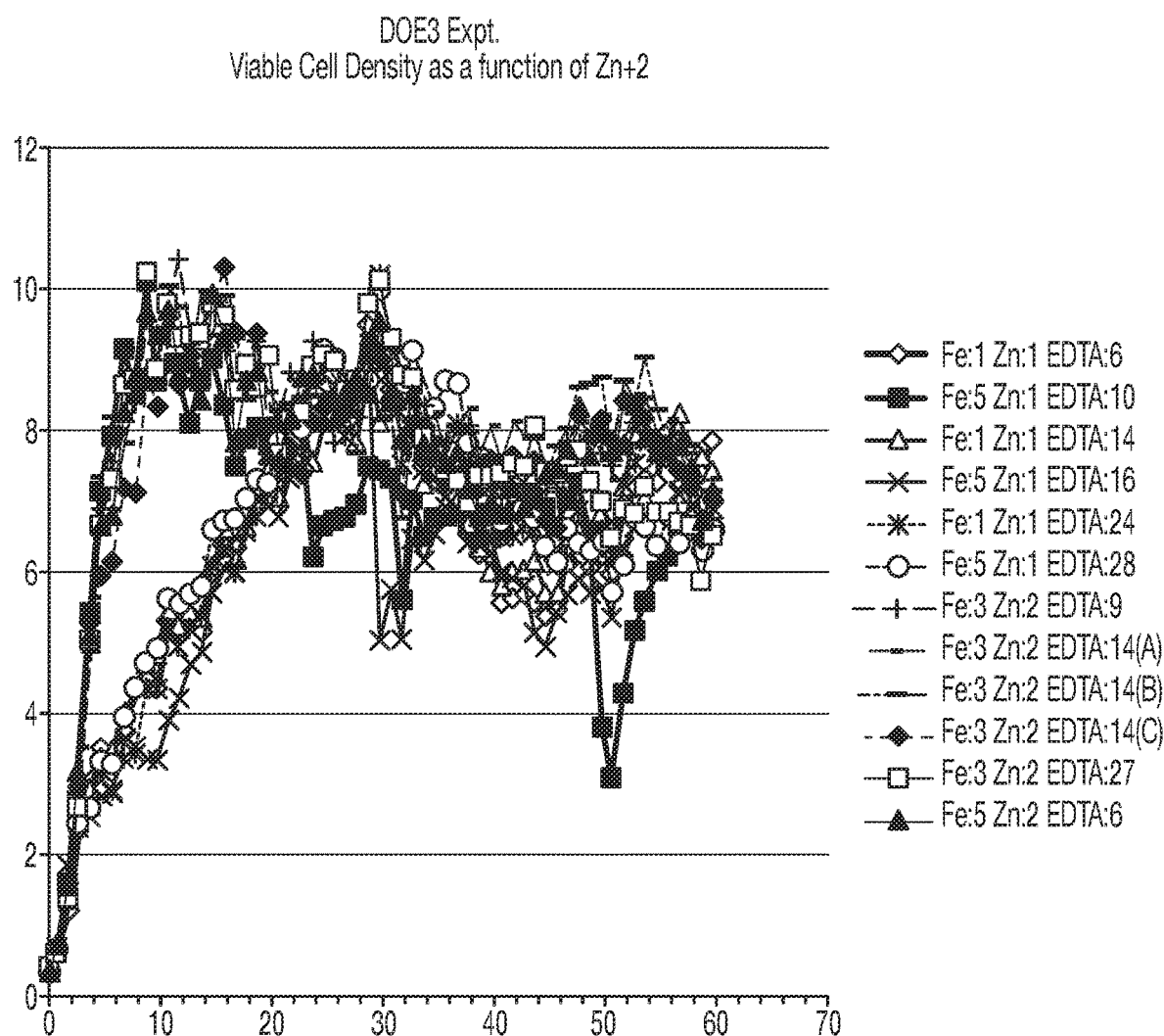
FIG. 10 is a graph of viable cell density as a function of bioreactor age, and shows the effect of varying EDTA concentrations on viable cell density in the presence of 0.76 µM $Zn^{+2}$ or 1.7 µM $Zn^{+2}$ (the initial concentration of $Zn^{+2}$ in the bioreactor corresponding to the label "Fe:5 Zn:1 EDTA:10" was 6.3 µM, rather than 0.76 µM; the targeted concentration of 0.76 µM $Zn^{+2}$ was implemented from Day 13 until the end of the experiment). Y-axis: viable cell density (millions of viable cells/mL); X-axis: bioreactor age in days.

In the DOE3 experiment, the five bioreactors with 0.76 µM Zn+2 had a much lower cell growth rate during the first 20 days (prior to reaching target cell density) than the six bioreactors that had 1.7 µM Zn+2 (FIG. 10). As noted previously, the bioreactor labeled "Fe:5, Zn:1, EDTA:10" experienced a very high Zn+2 concentration of 6.3 µM prior to Day 13. This bioreactor exhibited cell growth behavior in the period prior Day 20 that matched the bioreactors with 1.7 µM Zn+2. These data suggest that an extracellular Zn+2 concentration of 1.7 µM is sufficient to saturate the cells' intracellular needs for Zn+2 for cell division.

Figure 11A:
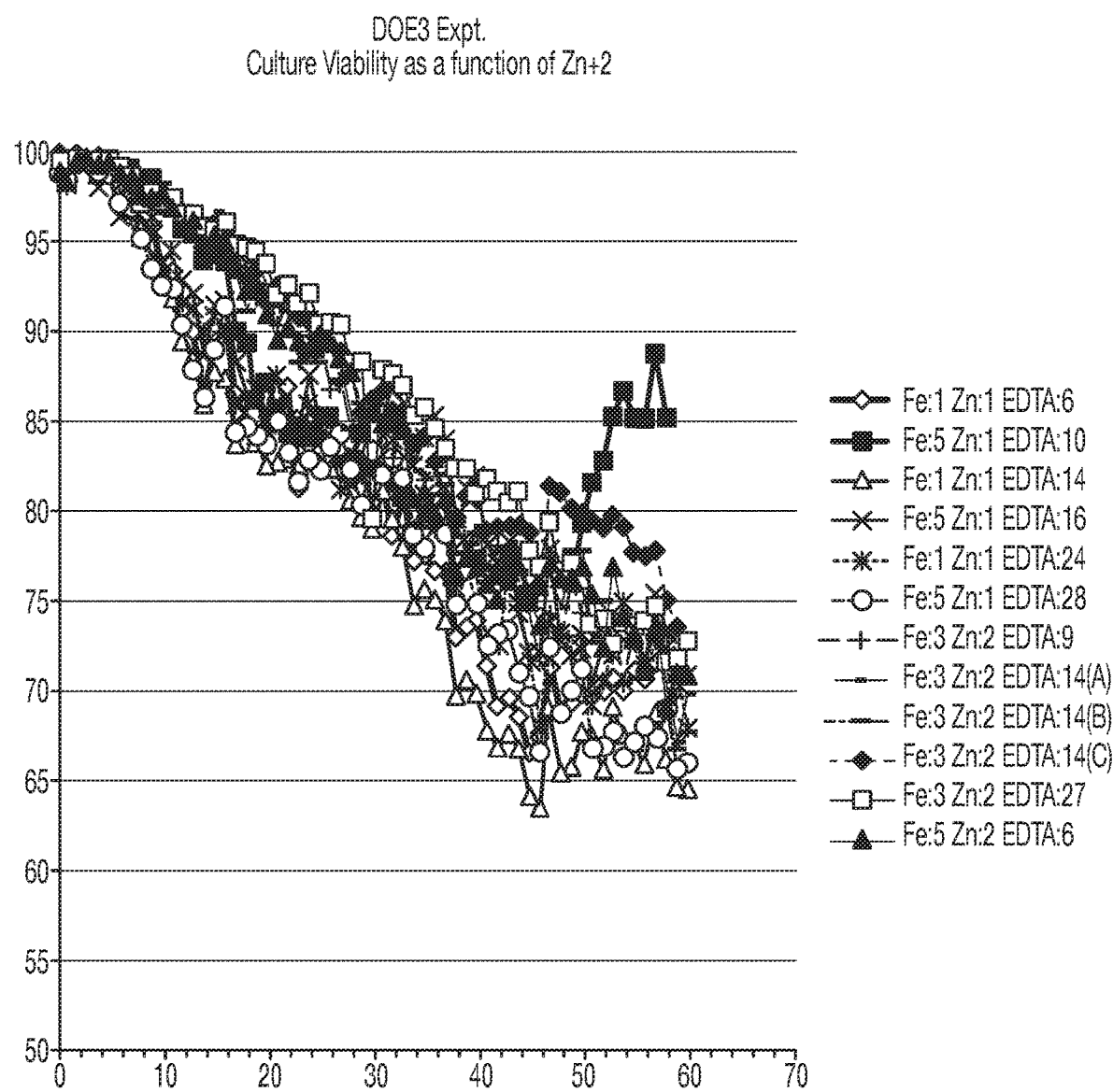
FIG. 11A is a graph of percentage of viable cells as a function of bioreactor age, and shows the effect of varying EDTA concentrations on culture viability in the presence of 0.76 µM $Zn^{+2}$ or 1.7 µM $Zn^{+2}$ (the initial concentration of $Zn^{+2}$ in the bioreactor corresponding to the label "Fe:5 Zn:1 EDTA:10" was 6.3 µM, rather than 0.76 µM; the targeted concentration of 0.76 µM $Zn^{+2}$ was implemented from Day 13 until the end of the experiment). Y axis: % viable cells; X-axis: bioreactor age in days.
Figure 11B:
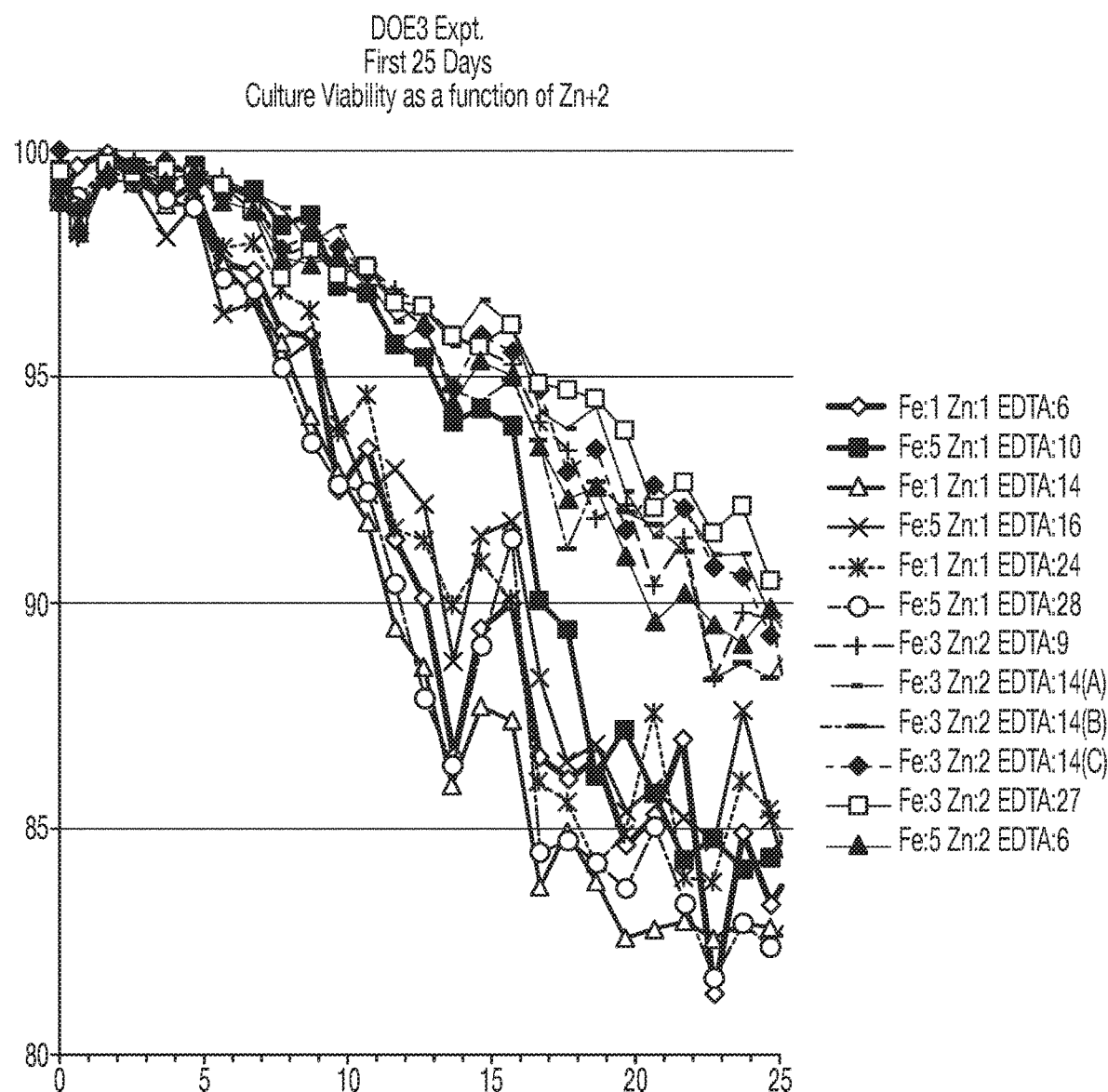
FIG. 11B is an enlargement of Days 0-25 of the graph shown in FIG. 11A. Y-axis: viable cell density (millions of viable cells/mL); X-axis: bioreactor age in days.

FIGS. 11A and 11B show that the culture viability of the five bioreactors with 0.76 µM Zn+2 was lower during the first 30 days than the culture viability of the six bioreactors with 1.7 µM Zn+2. Of particular note, the bioreactor labeled "Fe:5, Zn:1, EDTA:10" exhibited high culture viability at Day 10 and 13, but then reverted to match its sister bioreactor with a Zn+2 concentration of 0.76 µM soon after the Zn+2 concentration was corrected. This supports the hypothesis that culture viability is related to the instantaneous concentration of extracellular Zn+2, not to Zn+2 stores within the cell.

Figure 12A:
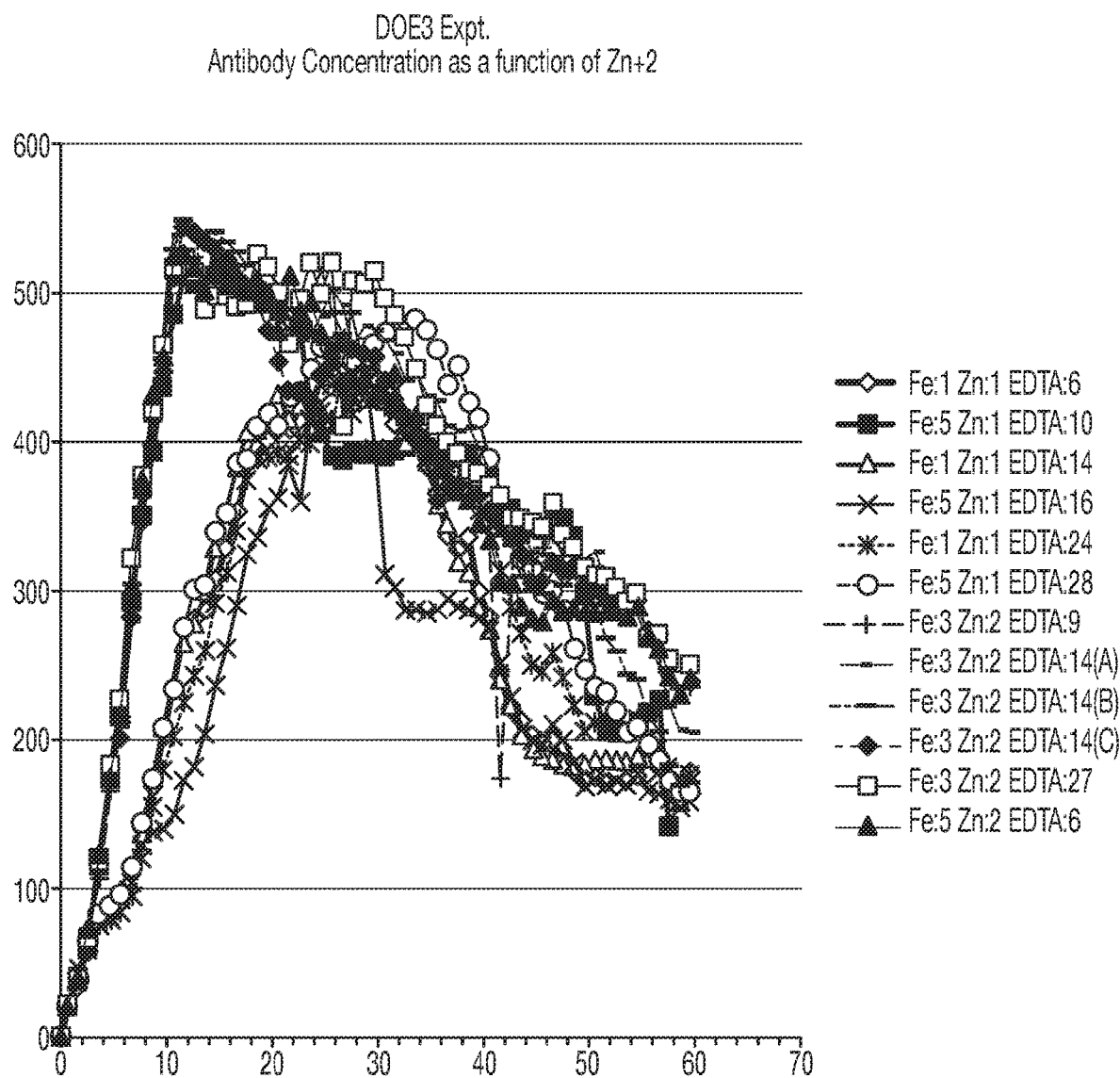
FIG. 12A is a graph of infliximab concentration as a function of bioreactor age, and shows the effect of varying EDTA concentrations on the concentration of infliximab in the presence of 0.76 µM $Zn^{+2}$ or 1.7 µM $Zn^{+2}$ (the initial concentration of $Zn^{+2}$ in the bioreactor corresponding to the label "Fe:5 Zn:1 EDTA:10" was 6.3 µM, rather than 0.76 µM; the targeted concentration of 0.76 µM $Zn^{+2}$ was implemented from Day 13 until the end of the experiment). The y-axis concentration mg/mL as indicated contains a typographical error. The concentration is mg/L. Y-axis: infliximab concentration (mg/L), X-axis: bioreactor age in days.
Figure 12B:
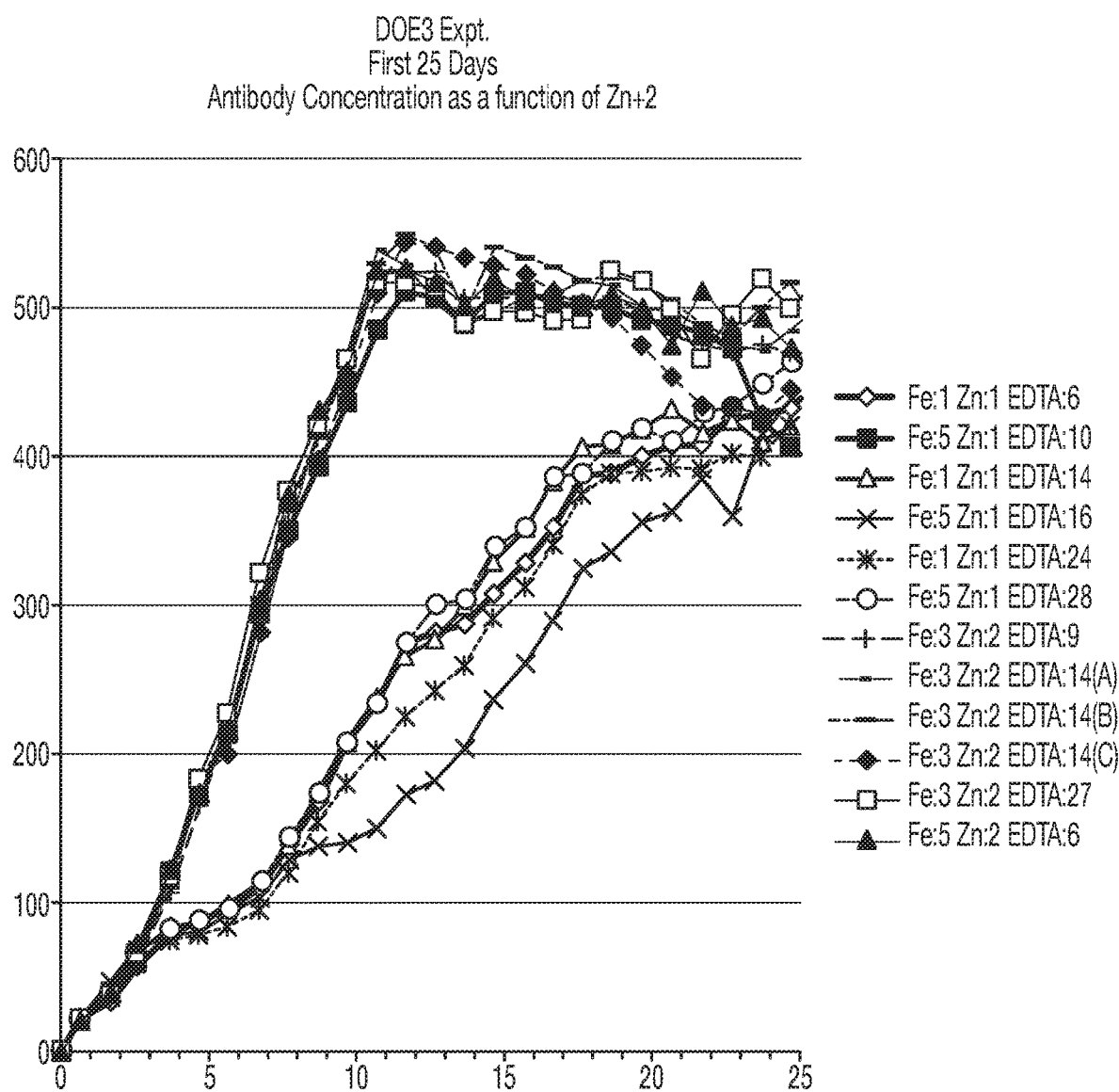
FIG. 12B is an enlargement of Days 0-25 of the graph shown in FIG. 12A. The y-axis concentration mg/mL as indicated contains a typographical error. The concentration is mg/L. Y-axis: infliximab concentration (mg/L), X-axis: bioreactor age in days.

FIGS. 12A and 12B show that the antibody concentration of the five bioreactors with 0.76 µM Zn+2 was lower for the first 20 days than the six bioreactors with 1.7 µM Zn+2. The bioreactor labeled "Fe:5, Zn:1, EDTA:10" exhibited antibody concentration comparable to the bioreactors at 1.7 µM Zn+2, supporting the hypothesis that antibody production is related to accumulated Zn+2 rather than to the instantaneous value of extracellular Zn+2.

FIGS. 10, 11A, 11B, 12A and 12B show that there is no clear correlation between [EDTA] and viable cell density, culture viability and antibody concentration in the DOE3 results.

The DOE3 experiment included a range of [Zn+2], [EDTA], and [EDTA Fe+3]. For example, [EDTA-Fe+3] ranged from 0.5 to 23 µM. However, the dominant factor in the outcome of these experiments was the extracellular concentration of Zn+2, ranging from 0.76 µM to 1.7 µM (and initially 6.3 µM in bioreactor "Fe:5, Zn:1, EDTA:10"). Bioreactors with extracellular Zn+2 of 1.7 µM had significantly higher CTL removal, sialic acid content, initial cell growth, initial culture viability, and initial antibody production than bioreactors with extracellular Zn+2 of 0.76 µM (FIGS. 8A, 8B, 9A, 9B, 10, 11A, 11B, 12A and 12B).

Within the bioreactors at a given Zn+2 concentration, there was some evidence of a secondary impact of [EDTA] (or [EDTA-Fe+3]) on CTL removal and sialic acid addition (FIGS. 8A, 8B, 9A and 9B). The results did not provide evidence of an impact of [EDTA] on cell growth, culture viability and antibody production (FIGS. 10, 11A, 11B, 12A and 12B). The impact of [EDTA] was more fully explored in the BSA Blending Experiments #1 and #2, to be discussed in the next section.

The bioreactor "Fe:5, Zn:1, EDTA:10" experienced a very high Zn+2 concentration of 6.3 µM prior to Day 13, then was returned to the targeted Zn+2 concentration of 0.76 µM. This bioreactor exhibited comparable initial cell growth (FIG. 10), culture viability (FIGS. 11A and 11B) and antibody productivity (FIGS. 12A and 12B) to the bioreactors with 1.7 µM Zn+2. However, this bioreactor exhibited greater initial CTL removal and sialic acid content than the bioreactors at 1.7 µM Zn+2. This bioreactor exhibited a "memory" for the initial high Zn+2 concentration that extended well beyond the correction of extracellular Zn+2 concentration for CTL removal, sialic acid content, cell density and antibody production (FIGS. 8A, 8B, 9A, 9B, 10, 12A and 12B). However, this bioreactor did not exhibit a memory for culture viability; that is, the culture viability corrected without delay as the extracellular Zn+2 concentration fell from 6.3 µM to 0.76 µM (FIGS. 11A and 11B).

Figure 9C:
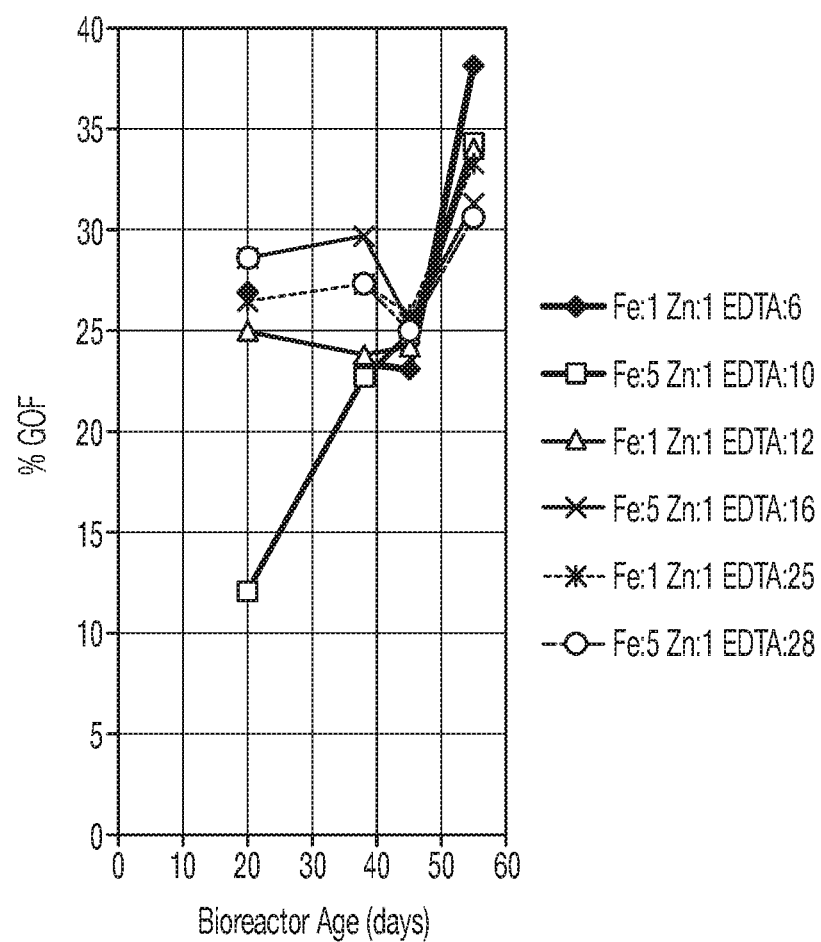
FIG. 9C is a graph of percentage of G0F (WAX Component 1) as a function of bioreactor age, and shows the effect of varying EDTA concentrations on the percentage of non-galactosylated species in the presence of 0.76 µM $Zn^{+2}$ (the initial concentration of $Zn^{+2}$ in the bioreactor corresponding to the label "Fe:5 Zn:1 EDTA:10" was 6.3 µM, rather than 0.76 µM; the targeted concentration of 0.76 µM $Zn^{+2}$ was implemented from Day 13 until the end of the experiment).
Figure 9D:
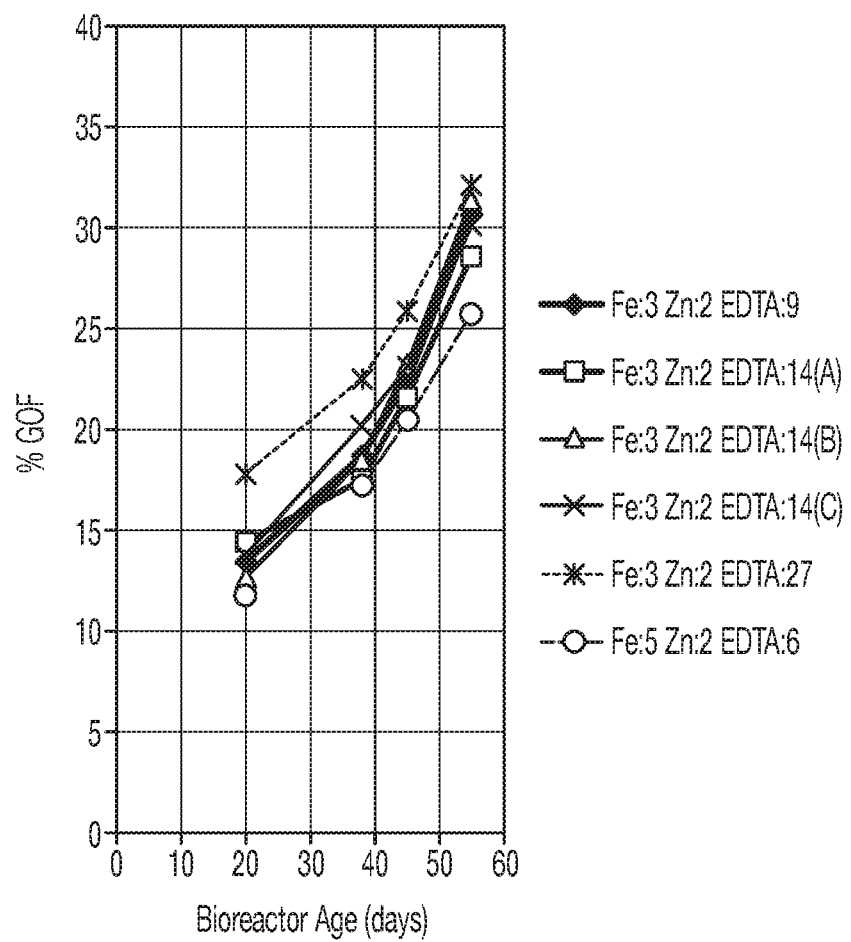
FIG. 9D is a graph percentage of G0F (WAX Component 1) as a function of bioreactor age, and shows the effect of varying EDTA concentrations on the percentage of non-galactosylated species in the presence of 1.7 µM $Zn^{+2}$.

FIGS. 9C and 9D are graphs of percentage of G0F (WAX Component 1) as a function of bioreactor age, and shows the effect of varying EDTA concentrations on the percentage of non-galactosylated species in the presence of 0.76 µM $Zn^{+2}$ and 1.7 µM $Zn^{+2}$.

The results of the DOE3 experiment are consistent with the hypotheses expressed previously for the SFM-10.1 experiment. Additional hypotheses also emerge:

CTL removal, sialic acid addition, cell growth and antibody expression are related to the accumulated amount of intracellular Zn+2, rather than to the current extracellular concentration of Zn+2. The accumulated stores of Zn+2 are based on the past history of extracellular Zn+2, not to the immediate extracellular concentration. This is the basis for a "cellular memory" concerning past extracellular Zn+2.

Culture viability is related to the current extracellular concentration of Zn+2.

Under the conditions of this experiment, an extracellular concentration of 1.7 µM Zn+2 was sufficient to saturate the cells need for Zn+2 to support enzymatic activities related to cell growth and antibody expression. However, 1.7 µM Zn+2 was not sufficient to saturate the cells need for Zn+2 to support CTL removal or sialic acid addition. These hypotheses are supported by the results for bioreactor "Fe:5, Zn:1, EDTA:10," which had a Zn+2 concentration of 6.3 µM prior to Day 13.

Example 6

BSA Blending Experiments No. 1 and No. 2

These two experiments employed SFM-10 medium. In each experiment, the same lots of PRIMATONE® and insulin were employed, assuring constant concentrations of Zn+2 and Fe+3. In BSA Blending Experiments No. 1 and No. 2, the Zn+2 concentrations were 1.1 and 1.2 µM, respectively.

In each experiment, BSA lots containing high and low concentrations of EDTA were identified, then mixed to create a range of EDTA concentrations in the bioreactors. BSA Blending Experiment No. 1 employed eight bioreactors, with duplication bioreactors at four EDTA concentrations. Duplicate bioreactors in BSA Blending Experiment No. 1 are labeled as "A" and "B". BSA Blending Experiment No. 2 employed eight bioreactors, each with a different EDTA concentration. Tables 3 and 4 list the Zn+2, Fe+3, EDTA and EDTA-Fe concentrations in the bioreactors in BSA Blending Experiments No. 1 and No. 2.

TABLE 3

Concentrations of Zn + 2, Fe + 3, EDTA, and [EDTA − Fe + 3] in the Eight Bioreactors of the BSA Blending Experiment No. 1 (concentrations are in µM).

| Bioreactor Arm[a] | [Zn + 2] | [Fe + 3] | [EDTA] | [EDTA − Fe] |
|---|---|---|---|---|
| "EDTA: 6(A)" | 1.2 | 3.1 | 5.9 | 2.8 |
| "EDTA: 6(B)" | 1.2 | 3.1 | 5.9 | 2.8 |
| "EDTA: 11(A)" | 1.2 | 3.1 | 10.8 | 7.7 |
| "EDTA: 11(B)" | 1.2 | 3.1 | 10.8 | 7.7 |
| "EDTA: 13(A)" | 1.2 | 3.1 | 13.2 | 10.1 |

TABLE 3-continued

Concentrations of Zn + 2, Fe + 3, EDTA, and
[EDTA − Fe + 3] in the Eight Bioreactors of the BSA
Blending Experiment No. 1 (concentrations are in µM).

| Bioreactor Arm[a] | [Zn + 2] | [Fe + 3] | [EDTA] | [EDTA − Fe] |
|---|---|---|---|---|
| "EDTA: 13(B)" | 1.2 | 3.1 | 13.2 | 10.1 |
| "EDTA: 16(A)" | 1.2 | 3.1 | 15.7 | 12.5 |
| "EDTA: 16(B)" | 1.2 | 3.1 | 15.7 | 12.5 |

[a]Bioreactor arms are designated by the approximate concentration of EDTA (in µM).

TABLE 4

Concentrations of Zn + 2, Fe + 3, EDTA and
[EDTA − Fe + 3] in the Eight Bioreactors of the
BSA Blending Experiment No. 2 (concentrations are in µM).

| Bioreactor Arm[a] | [Zn + 2] | [Fe + 3] | [EDTA] | [EDTA − Fe] |
|---|---|---|---|---|
| "EDTA: 2.7" | 1.1 | 4.5 | 2.7 | −1.8 |
| "EDTA: 4.5" | 1.1 | 4.5 | 4.5 | 0.0 |
| "EDTA: 4.9" | 1.1 | 4.5 | 4.9 | 0.5 |
| "EDTA: 14.6" | 1.1 | 4.5 | 14.6 | 10.1 |
| "EDTA: 15.5" | 1.1 | 4.5 | 15.5 | 11.0 |
| "EDTA: 15.7" | 1.1 | 4.5 | 15.7 | 11.2 |
| "EDTA: 19.2" | 1.1 | 4.5 | 19.2 | 14.7 |
| "EDTA: 26.5" | 1.1 | 4.5 | 26.5 | 22.0 |

[a]Bioreactor arms are designated by the approximate concentration of EDTA (in µM).

Figure 13A:
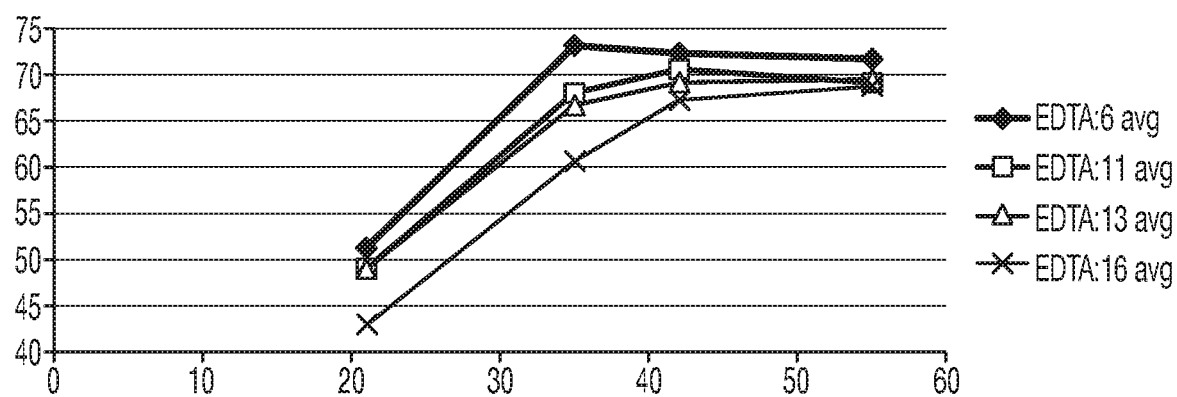
FIG. 13A is a graph of CTL removal (expressed as percentage of des-Lys and computed using the cIEF method from Peak 1 data) as a function of bioreactor age, and shows the effect of varying EDTA concentration (µM) on CTL removal (results are presented as an average from two duplicate bioreactors). Y-axis: % des1-Lys; X-axis: bioreactor age in days.
Figure 14A:
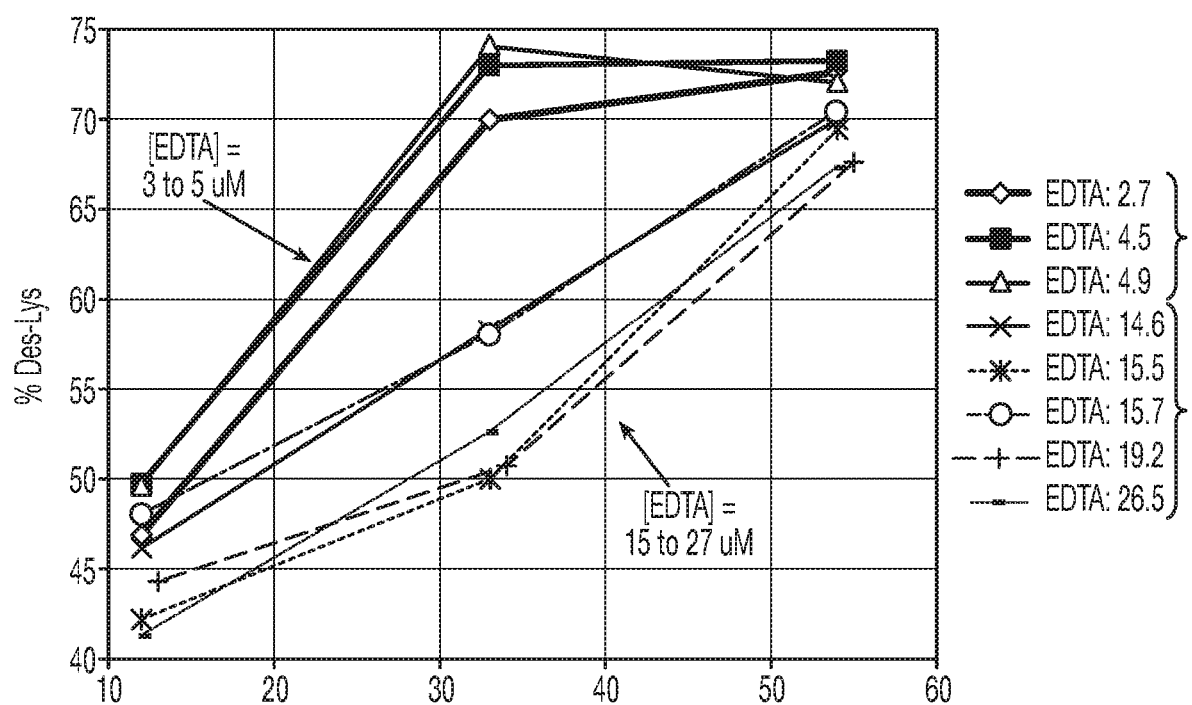
FIG. 14A is a graph of CTL removal (expressed as percentage of des-Lys and computed using the cIEF method from Peak 1 data) as a function of bioreactor age, and shows the effect of varying EDTA concentration (µM) on CTL removal. X-axis: bioreactor age in days.

In both BSA blending experiments, the bioreactors with higher EDTA concentrations experienced less CTL removal, and visa versa—the bioreactors with lower EDTA concentrations experienced increased CTL removal. The effect was most evident at Day 35 in each experiment, then diminished at later culture days (FIGS. 13A and 14A).

Figure 13B:
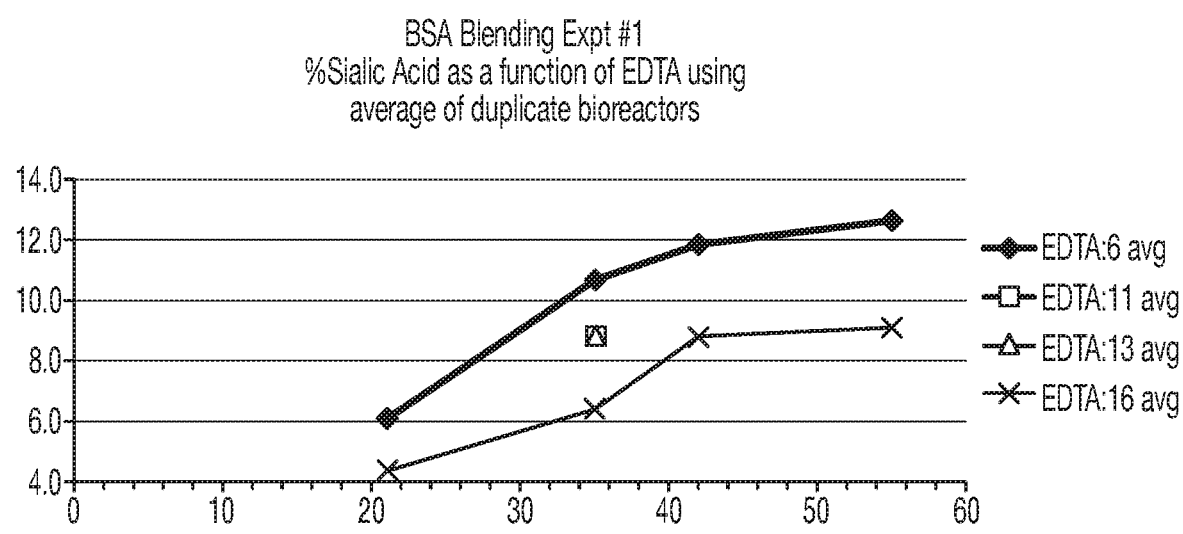
FIG. 13B is a graph of percentage of infliximab oligosaccharides with sialic acid, as determined by the WAX method, as a function of bioreactor age, and shows the effect of varying EDTA concentration (µM) on sialic acid content (results are presented as an average from two duplicate bioreactors). Y-axis: % sialic acid; X-axis: bioreactor age in days.
Figure 14B:
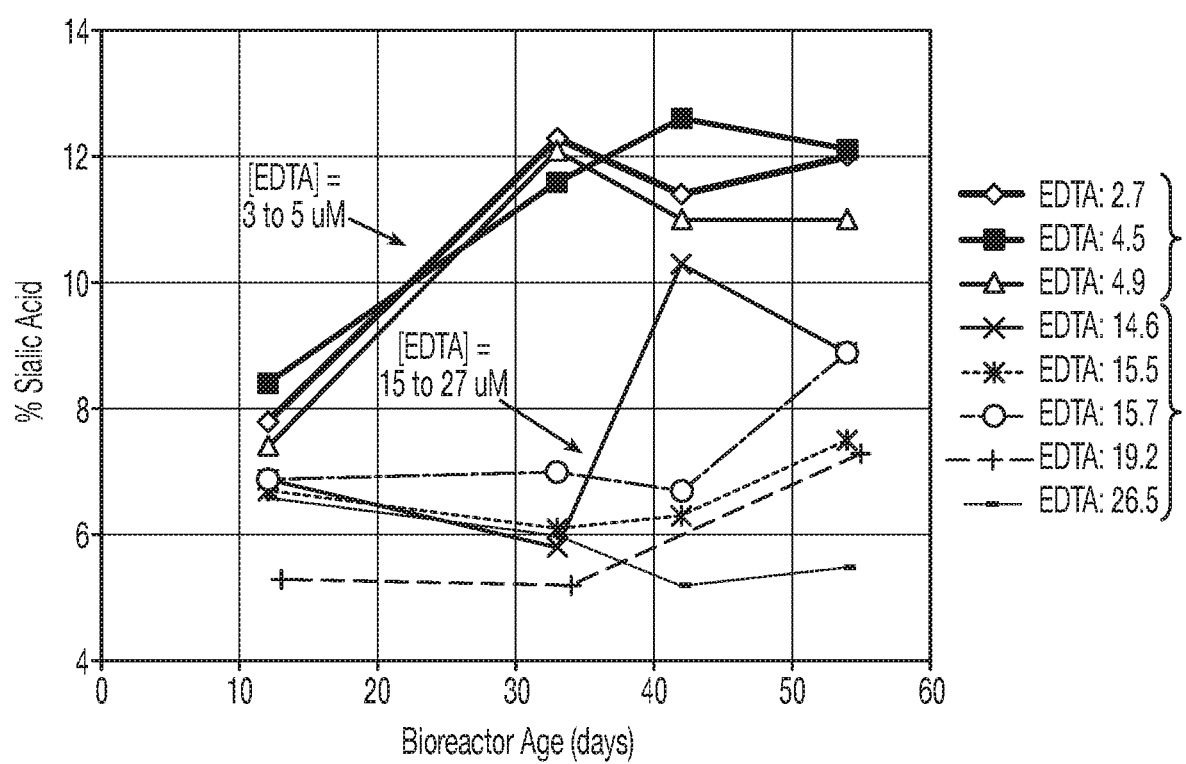
FIG. 14B is a graph of percentage of infliximab oligosaccharides with sialic acid, as determined by the WAX method, as a function of bioreactor age, and shows the effect of varying EDTA concentration (µM) on sialic acid content.

In both BSA blending experiments, the bioreactors with higher EDTA concentrations experienced lower sialic acid content and visa versa—the bioreactors with lower EDTA concentrations experienced higher sialic acid content. The effect was sustained for early, middle and late bioreactor samples (FIGS. 13B and 14B).

Figure 13C:
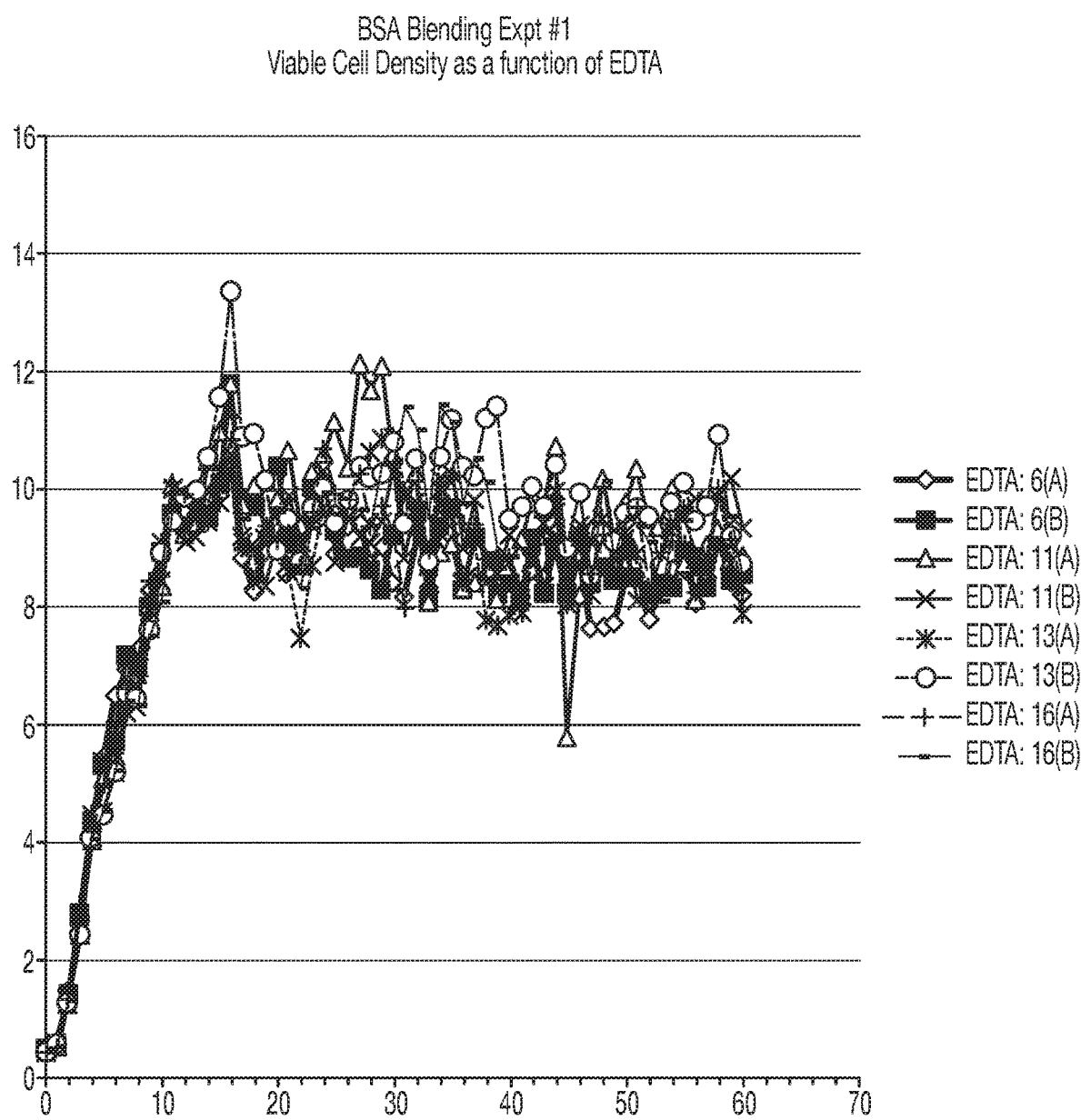
FIG. 13C is a graph of viable cell density as a function of bioreactor age, and shows the effect of varying EDTA concentration (µM) on viable cell density. Y-axis: viable cell density (millions of viable cells/mL); X-axis: bioreactor age in days.
Figure 13D:
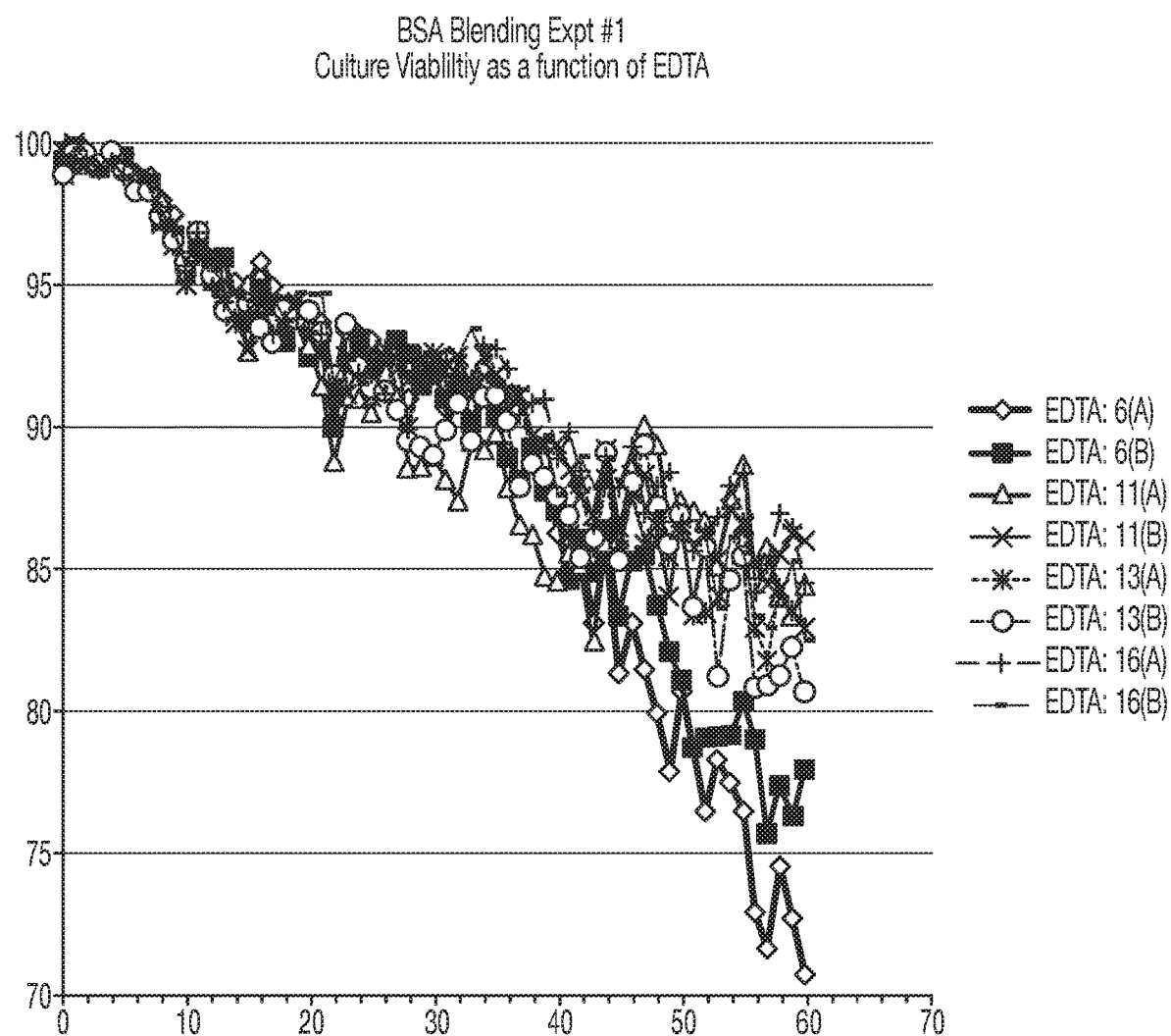
FIG. 13D is a graph of percentage of viable cells as a function of bioreactor age, and shows the effect of varying EDTA concentration (µM) on culture viability. Y-axis: % viable cells; X-axis: bioreactor age in days.
Figure 14C:
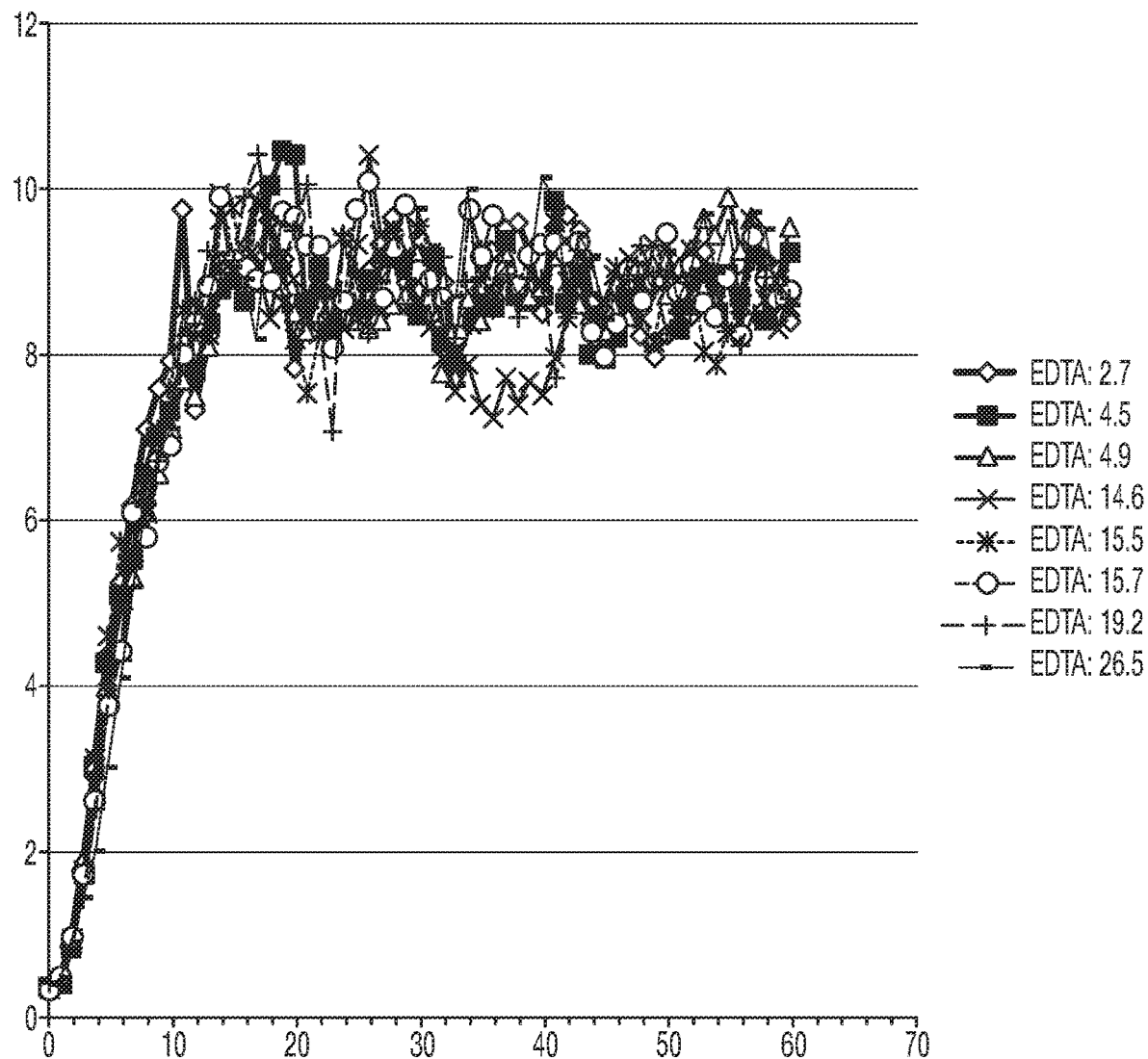
FIG. 14C is a graph of viable cell density as a function of bioreactor age, and shows the effect of varying EDTA concentration (µM) on viable cell density. Y-axis: viable cell density (millions of viable cells/mL); X-axis: bioreactor age in days.
Figure 14D:
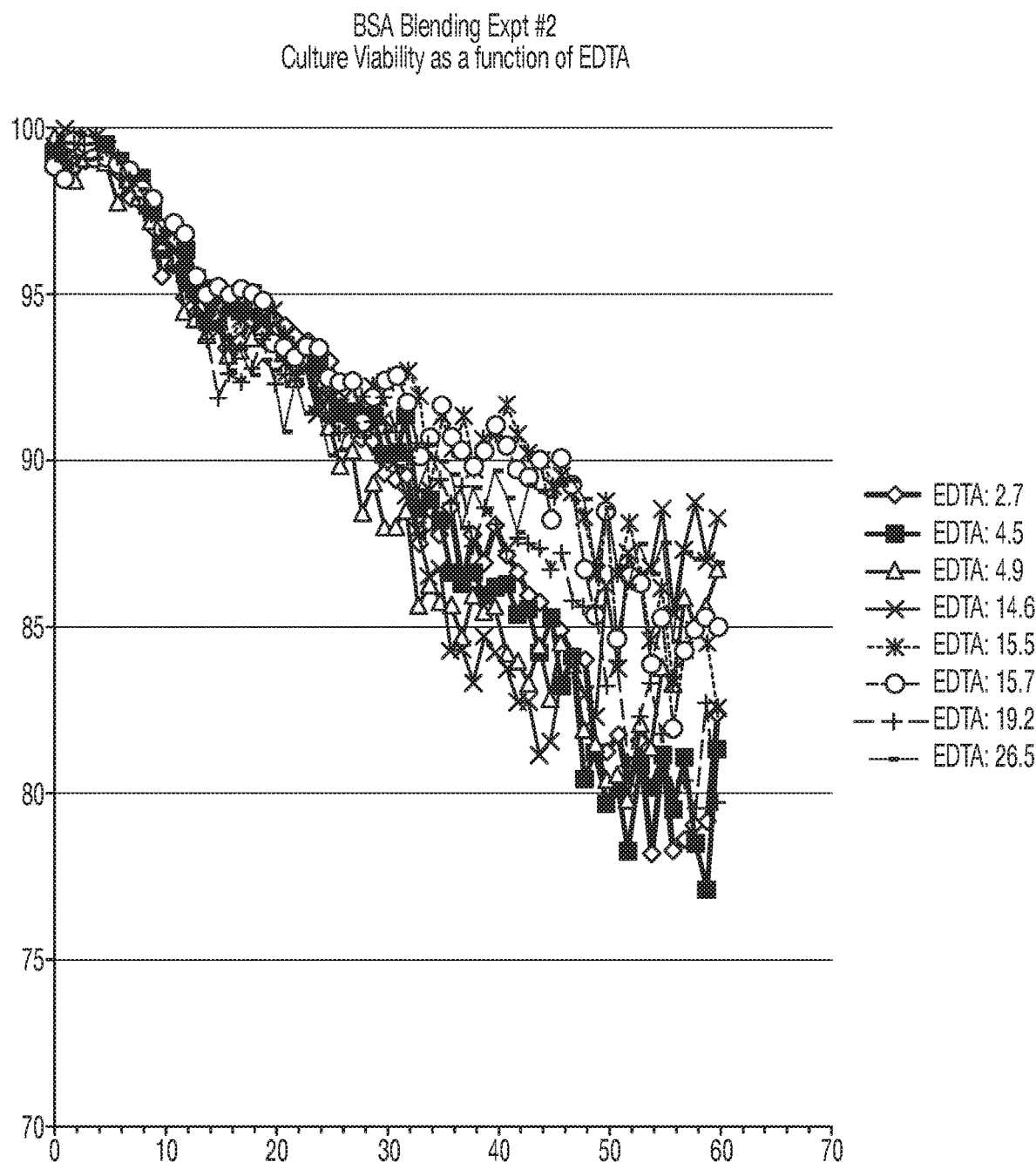
FIG. 14D is a graph of percentage of viable cells as a function of bioreactor age, and shows the effect of varying EDTA concentration (µM) on culture viability. Y-axis: % viable cells; X-axis: bioreactor age in days.

In both BSA blending experiments, the bioreactors with higher EDTA and lower EDTA concentrations exhibited comparable cell growth (FIGS. 13C and 14C) and comparable culture viability (FIGS. 13D and 14D).

Figure 13E:
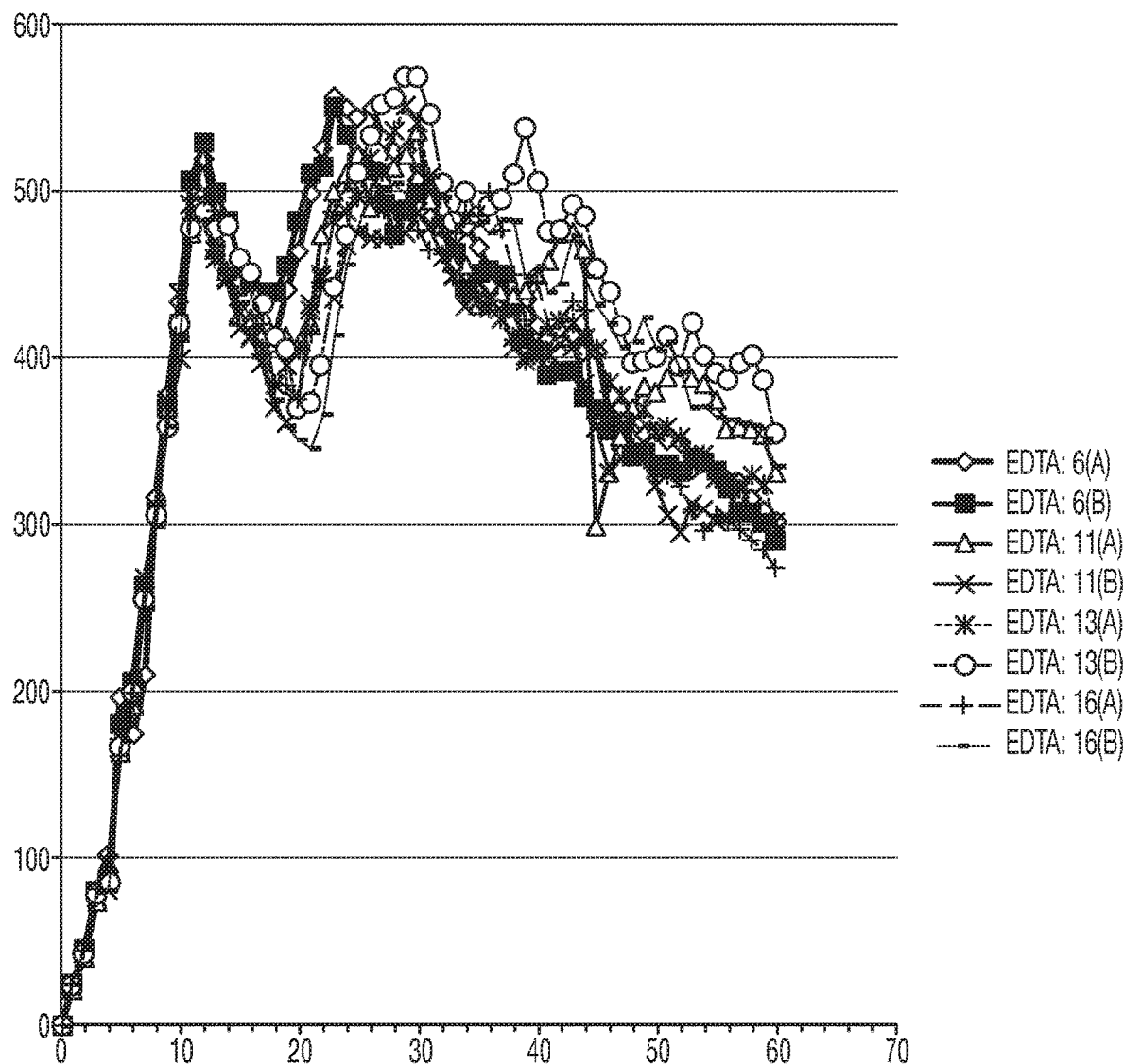
FIG. 13E is a graph of infliximab concentration as a function of bioreactor age, and shows the effect of varying EDTA concentration (µM) on the concentration of infliximab. The y-axis concentration mg/mL as indicated contains a a typographical error. The concentration is mg/L. Y-axis: infliximab concentration (mg/L), X-axis: bioreactor age in days.
Figure 13F:
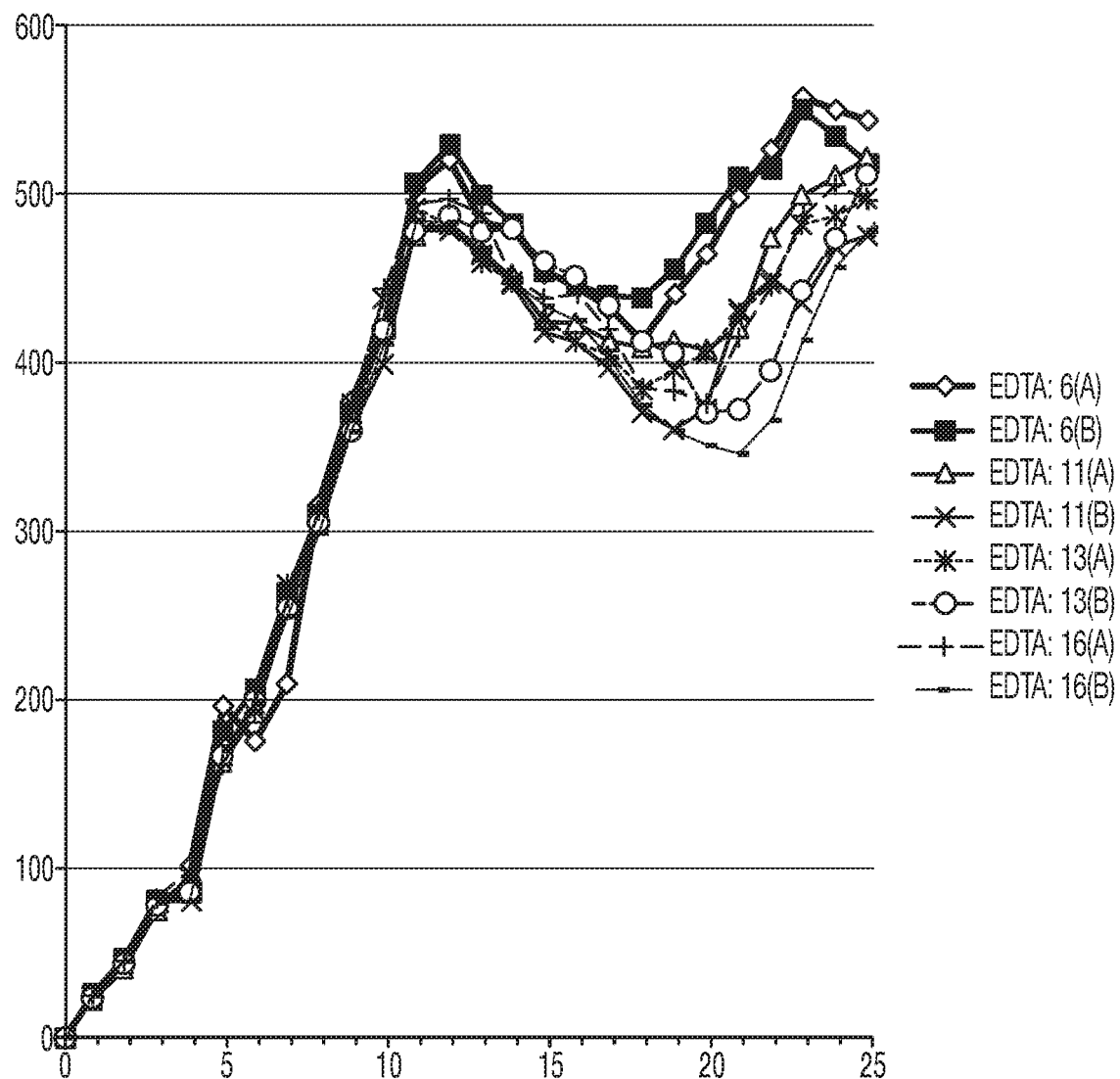
FIG. 13F is an enlargement of Days 0-25 of the graph shown in FIG. 13E. The y-axis concentration mg/mL as indicated contains a typographical error. The concentration is mg/L. Y-axis: infliximab concentration (mg/L), X-axis: bioreactor age in days.
Figure 14E:
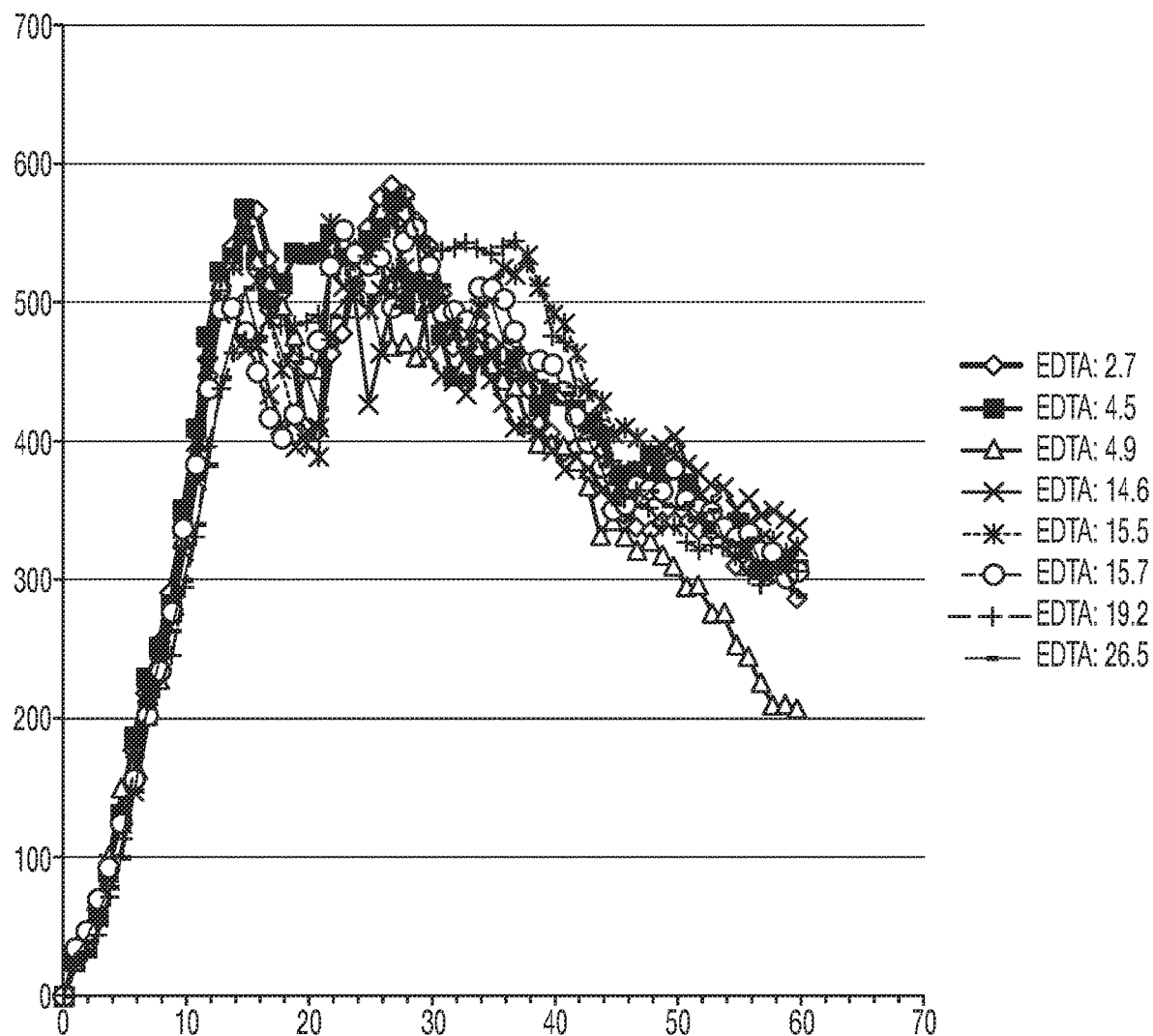
FIG. 14E is a graph of infliximab concentration as a function of bioreactor age, and shows the effect of varying EDTA concentration (µM) on the concentration of infliximab. The y-axis concentration mg/mL as indicated contains a a typographical error. The concentration is mg/L. Y-axis: infliximab concentration (mg/L), X-axis: bioreactor age in days.
Figure 14F:
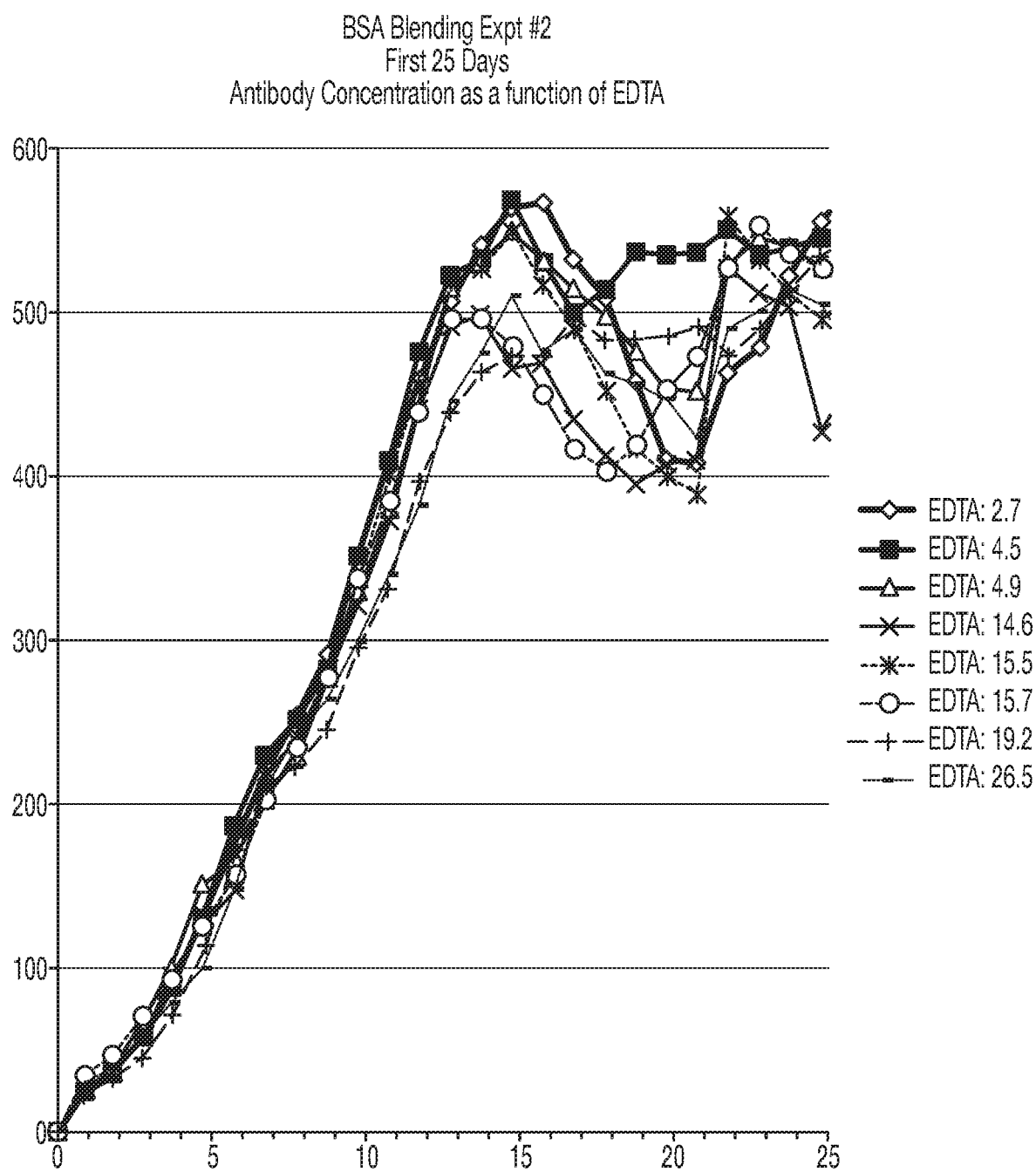
FIG. 14F is an enlargement of Days 0-25 of the graph shown in FIG. 14E. The y-axis concentration mg/mL as indicated contains a typographical error. The concentration is mg/L. Y-axis: infliximab concentration (mg/L), X-axis: bioreactor age in days.

A minor effect of EDTA concentration was noted on antibody production in the BSA blending experiments. In BSA Blending Experiment No. 1, bioreactors with high and low EDTA have comparable antibody production prior to reaching target cell density. During the period just after reaching target cell density (from approximately Days 15 to Day 25) bioreactors with higher EDTA have lower antibody expression than bioreactors with low EDTA (FIGS. 13E and 13F). In BSA Blending Experiment No. 2, a reduction of antibody production was noted for the two highest [EDTA] starting at Day 10, and bioreactors with the lowest [EDTA] exhibited higher antibody production at approximately Day 15 (FIGS. 14E and 14F). However, an effect of [EDTA] on antibody production was not observed in the DOE3 experiment (FIG. 12B).

For bioreactors with extracellular Zn+2 of approximately 1.1 to 1.2 µM, the BSA blending experiments demonstrated that EDTA concentration can have a significant impact on CTL removal and sialic acid addition. In addition, there may be a minor impact of EDTA concentration on antibody production during the period from Day 10 to Day 25, although this effect was not evident in the DOE3 experiment. At these Zn+2 concentrations, EDTA had no discernable impact on cell growth or culture viability.

Because the concentration of Fe+3 was constant in the bioreactors of the BSA blending experiments, the correlations noted above for [EDTA] are equally valid for [EDTA-Fe+3].

Figure 13G:
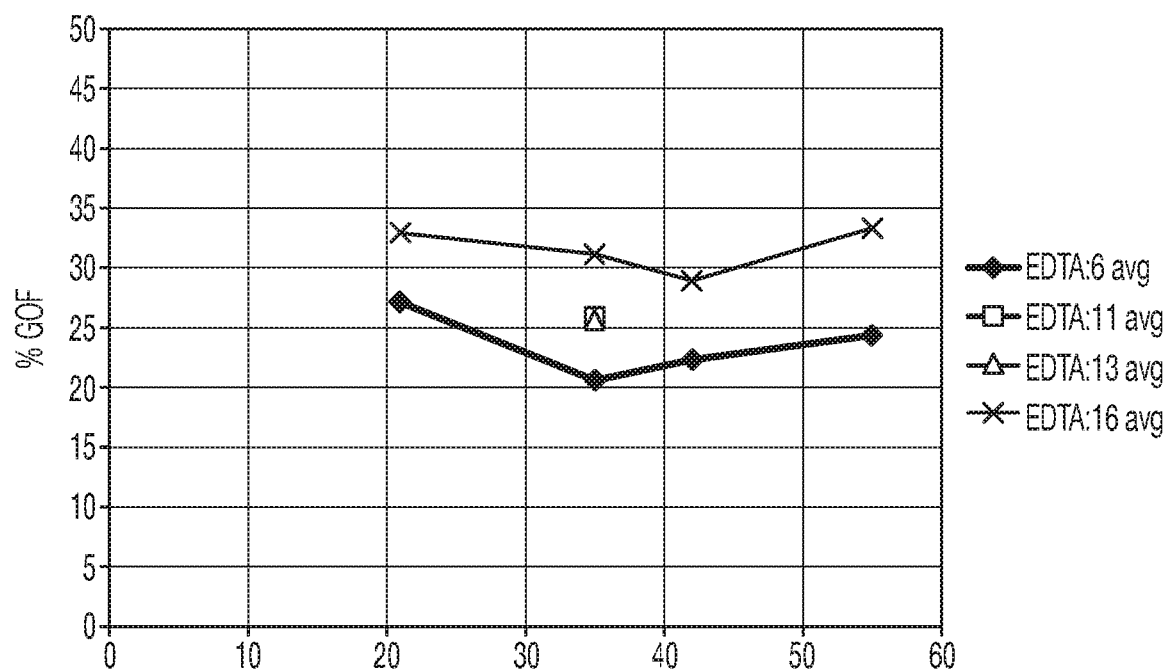
FIG. 13G is a graph of percentage of G0F (WAX Component 1) as a function of bioreactor age, and shows the effect of varying EDTA concentration (µM) on the percentage of infliximab oligosaccharides that lack galactose. X-axis: bioreactor age in days.
Figure 15:
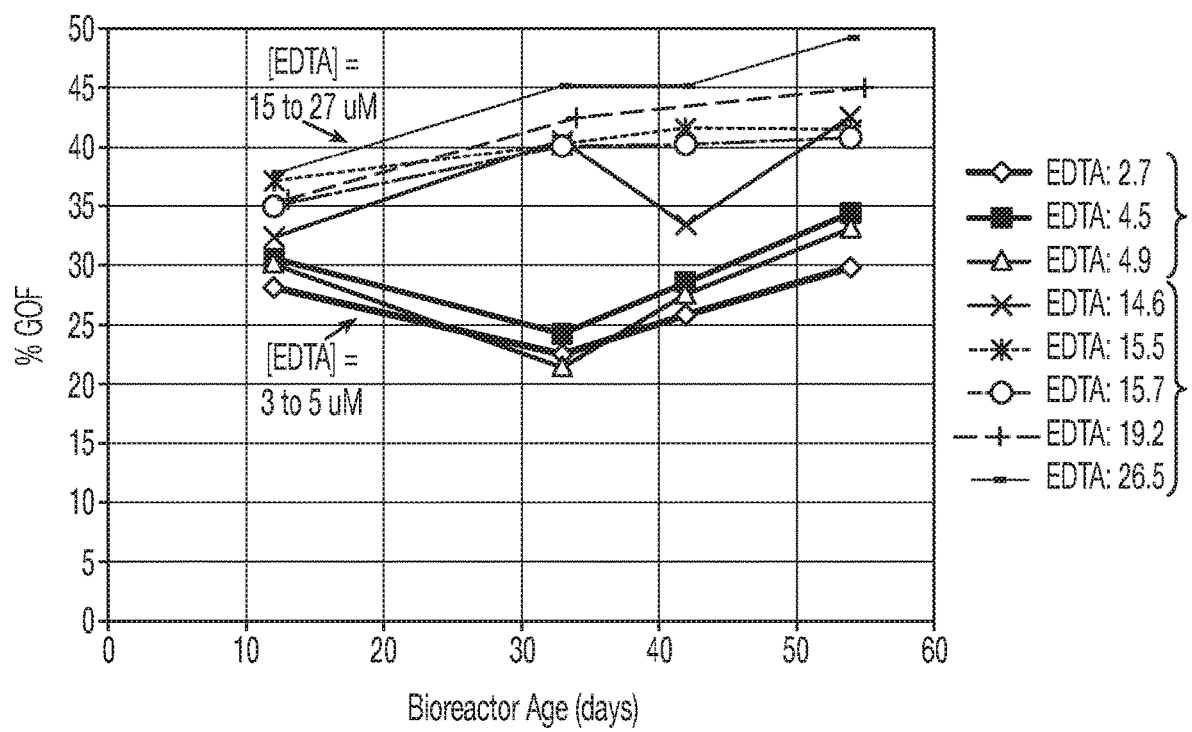
FIG. 15 is a graph of percentage of G0F (WAX Component 1) as a function of bioreactor age, and shows the effect of varying EDTA concentration (µM) on the percentage of infliximab oligosaccharides that lack galactose.

In both BSA blending experiments, decreasing EDTA concentration was shown to lead to a decrease in the percentage of agalactosylated oligosaccharides (FIGS. 13G and 15). Thus, decreasing the concentration of EDTA leads to both more galactose and more sialic acid content.

Although not wishing to be bound by any particular theory, the data from the BSA blending experiments support the following hypotheses:

EDTA (or [EDTA-Fe+3]) can influence the rate of Zn+2 uptake by cells. This effect is likely to be most apparent when the extracellular concentration of Zn+2 is low, and the cells are experiencing intracellular Zn+2 deficiency in support of enzymes that have Zn+2 requirements.

The cells have elaborate intracellular systems for storing and distributing Zn+2, and there are priorities for Zn+2 distribution in periods of Zn+2 limitation. Under conditions of Zn+2 limitation, the cells will place a priority on intracellular processes requiring Zn+2 for cell division. Thus, in BSA Blending Experiments No. 1 and No. 2, there was no impact of EDTA on cell growth because the cells had adequate Zn+2 for cell division under the conditions of this study. Likewise, antibody expression was minimally affected by EDTA under the conditions of this experiment. The intracellular distribution of Zn+2 to support CTL removal and sialic acid addition have a lower intracellular priority than distribution of Zn+2 for cell growth. Thus, under conditions in which EDTA does not affect cell growth, there can be a significant impact of EDTA on CTL removal and sialic acid addition.

Infliximab bioreactors are operated in the first 15-20 days in a manner that resembles fed-batch culture. That is, cells are inoculated to a low initial cell density, and are continuously fed for the next 15 to 20 days with fresh medium to support cell growth and antibody expression. Therefore, the experimental results described herein apply equally to fed-batch and perfusion cultures.

Example 7

Further Analysis of the DOE3 and BSA Blending No. 1 and No. 2

Experiments

The DOE3 and BSA Blending experiments were all conducted in the same laboratory using the same small-scale bioreactor model, and the samples were analyzed by the same assay group. Therefore, it should be possible to compare the results of the DOE3 and BSA Blending No. 1 and No. 2 experiments with one another.

Figure 16:
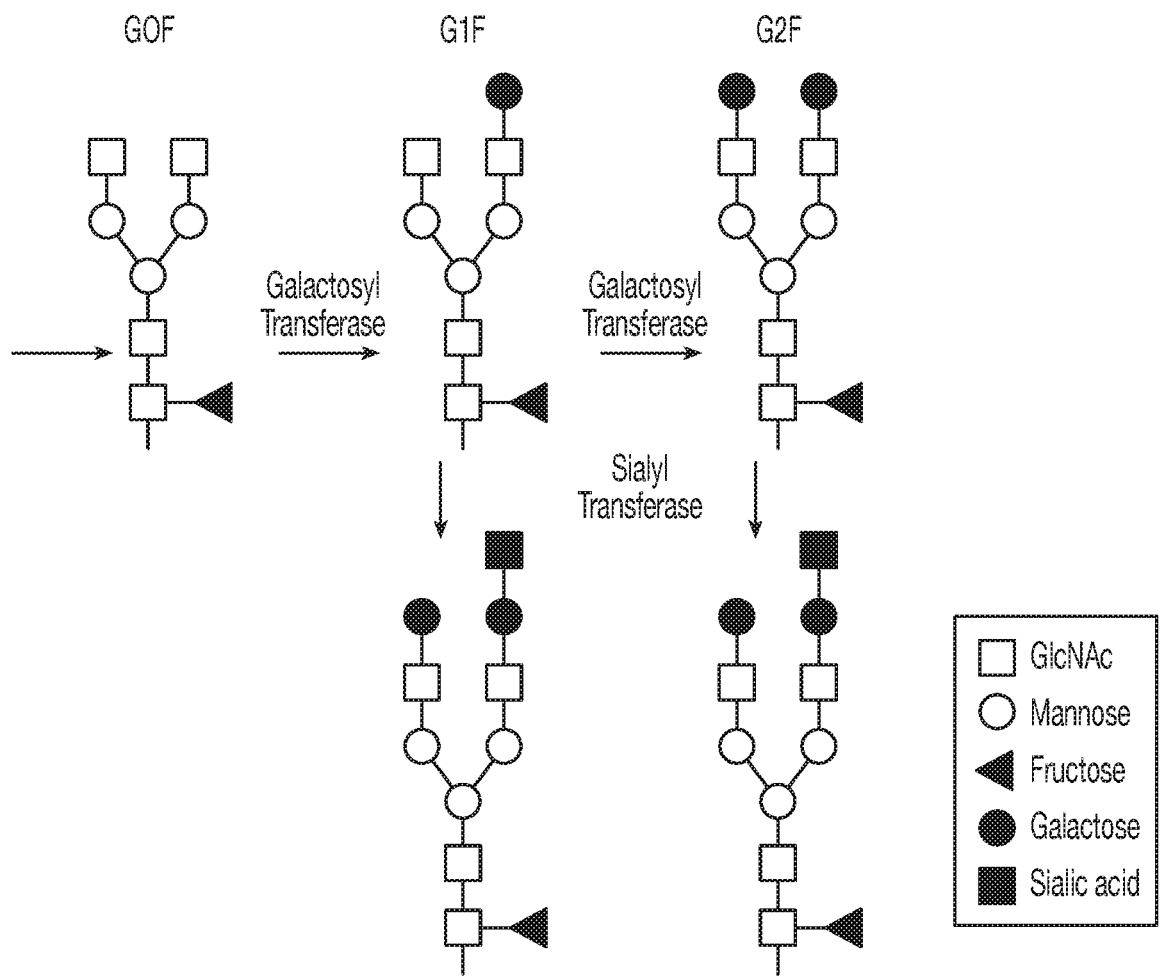
FIG. 16 shows a biosynthetic pathway for the most common neutral oligosaccharides of infliximab, G0F, G1F and G2F, and a biosynthetic pathway from neutral oligosaccharides to sialylated forms.
Figure 17:
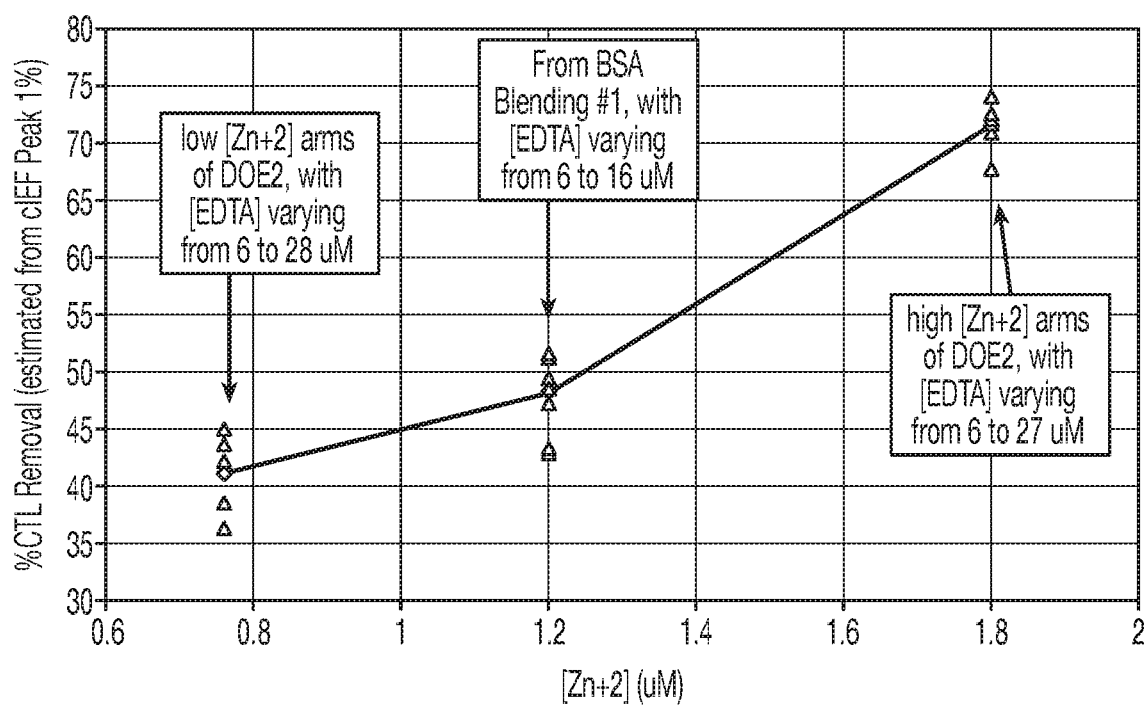
FIG. 17 is a graph of CTL removal (computed using the cIEF method from Peak 1 data) as a function of $Zn^{+2}$ concentration, and shows the percentage of CTL removal at Day 20 for the DOE3 and BSA Blending No. 1 experiments (the blue data points and the line represents the average).
Figure 18:
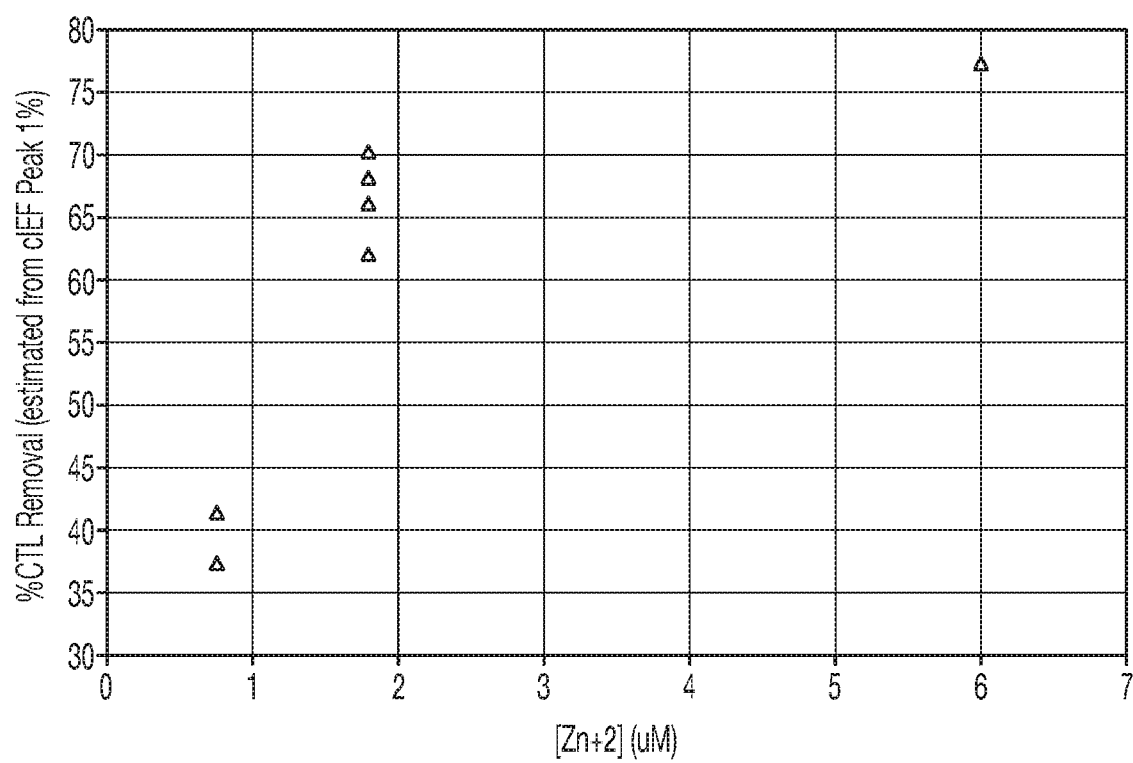
FIG. 18 is a graph of CTL removal (computed using the cIEF method from Peak 1 data) as a function of $Zn^{+2}$ concentration, and shows the percentage of CTL removal at Day 13 for the DOE3 experiment.
Figure 19:
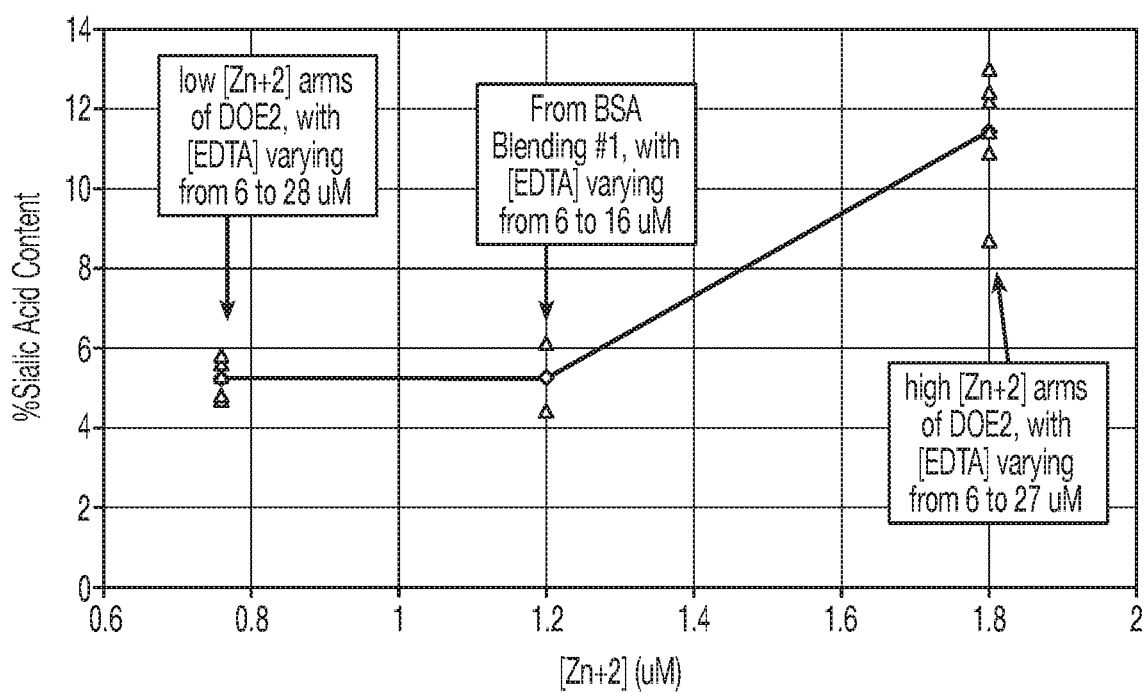
FIG. 19 is a graph of sialic acid content as a function of $Zn^{+2}$ concentration, and shows the percentage of sialic acid at Day 20 for the DOE3 and BSA Blending No. 1 experiments (the line represents the average).
Figure 20:
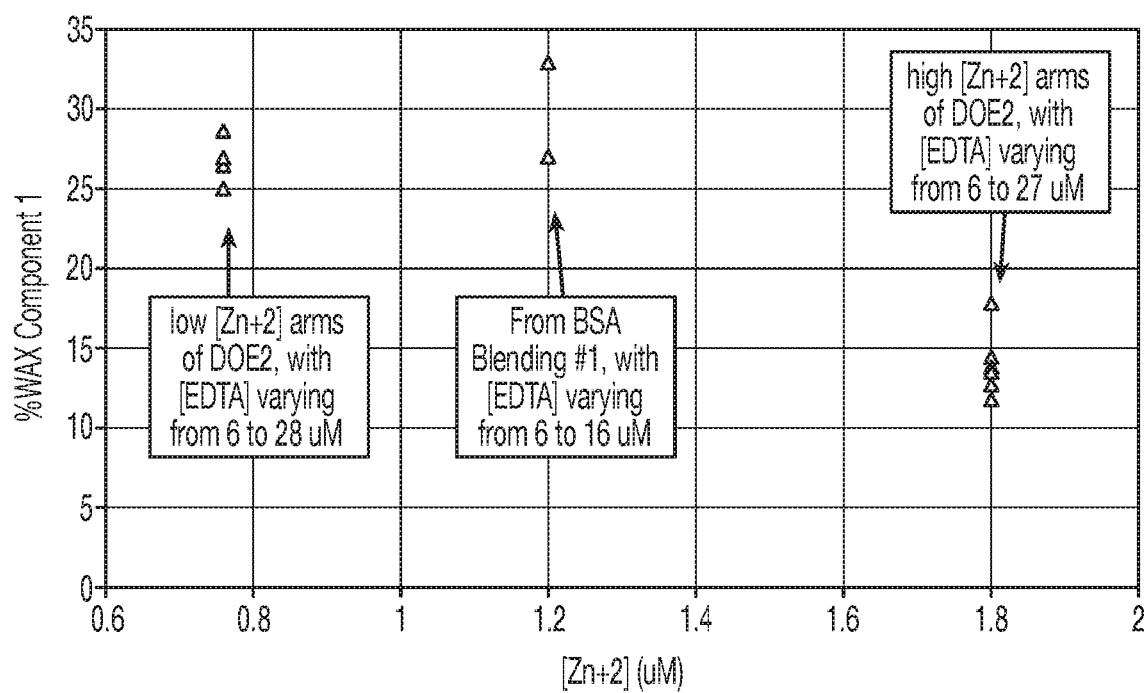
FIG. 20 is a graph of percentage of WAX Component 1 (G0F) as a function of $Zn^{+2}$ concentration, and shows the percentage of infliximab oligosaccharides that lack galactose at Day 20 for the DOE3 and BSA Blending No. 1 experiments.

In the DOE3 experiment and the BSA Blending No. 1 experiment, samples were collected at Day 20, and were analyzed by cIEF and the WAX assay. FIGS. 17, 19, 20 and 21 show the Day 20 data from the DOE3 experiment and the BSA Blending No. 1 experiment plotted together. The results shown in FIGS. 17, 19 and 20 support previous analyses, namely, that CTL removal increases with increasing [Zn+2], sialic acid content increases with increasing [Zn+2], and the percentage of agalactosyl oligosaccharides decreases with increasing [Zn+2]. These latter two results are consistent with promotion of the enzyme reactions for galactose addition and sialic acid addition, as shown in FIG. 16.

Figure 21:
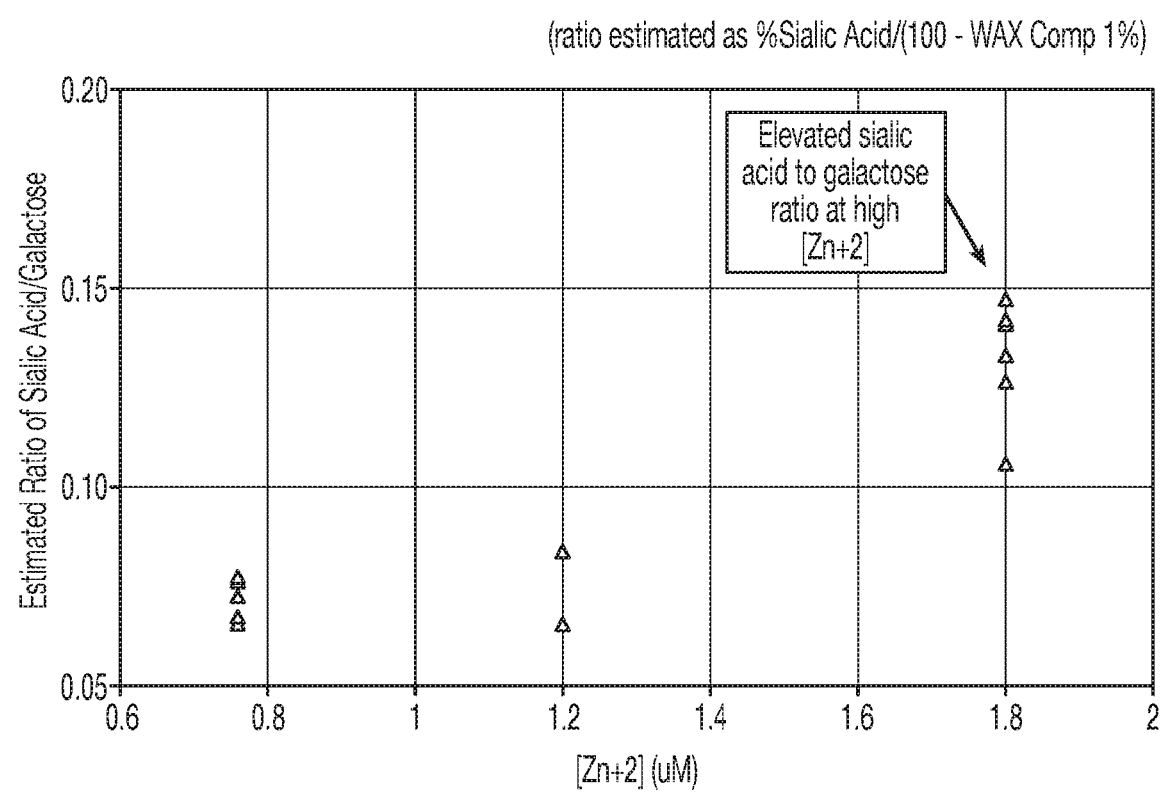
FIG. 21 is a graph of estimated ratio of sialic acid to galactose (estimated as percent sialic acid/(100−percentage of WAX Component 1) as a function of $Zn^{+2}$ concentration, and shows the estimated ratio of sialic acid to galactose at Day 20 for the DOE3 and BSA Blending No. 1 experiments.
Figure 22:
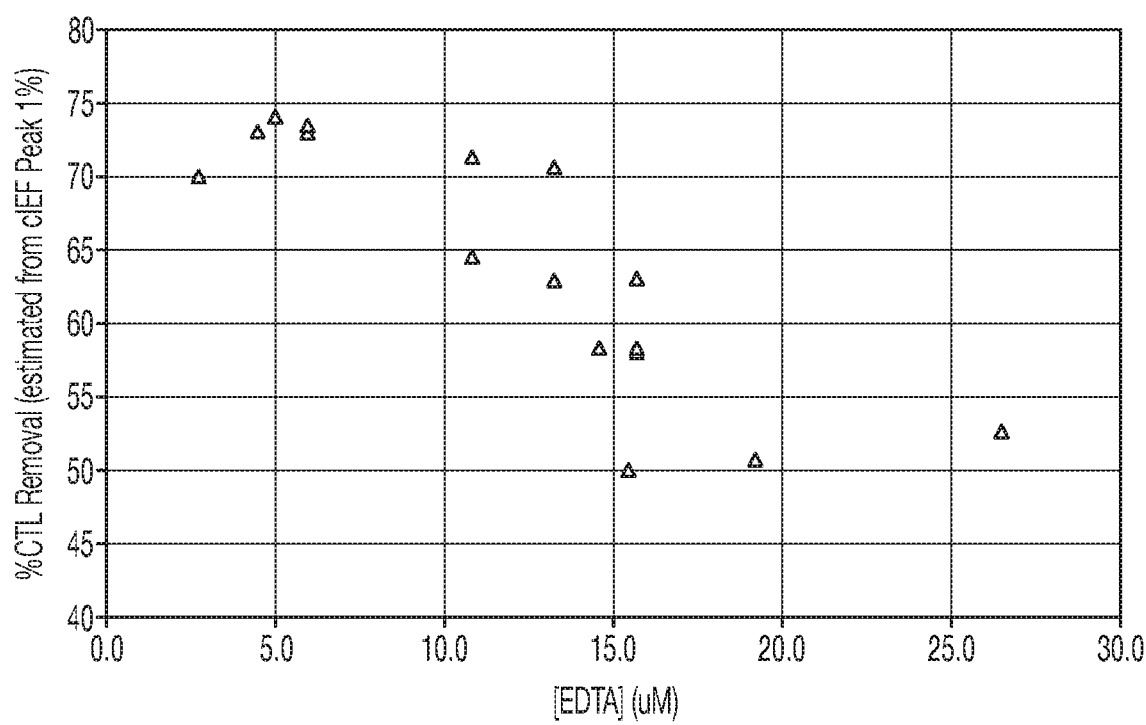
FIG. 22 is a graph of CTL removal (computed using the cIEF method from Peak 1 data) as a function of EDTA concentration, and shows the percent CTL removal in the presence of 1.1-1.2 µM $Zn^{+2}$ at Days 33-35 for Blending No. 1 and No. 2 experiments.
Figure 23:
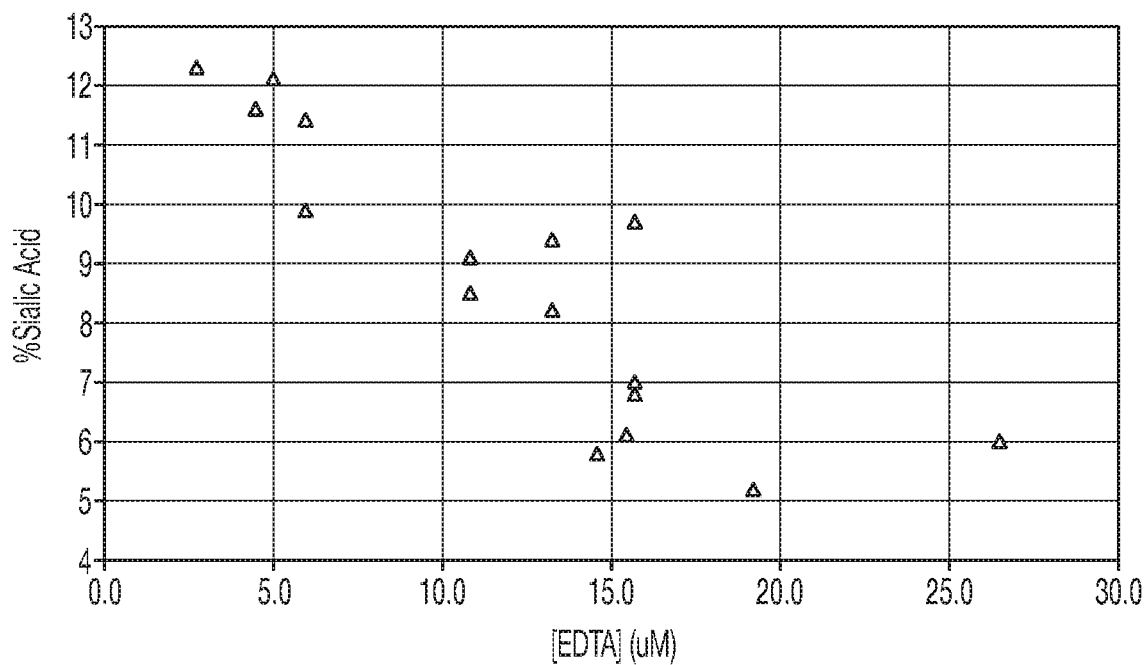
FIG. 23 is a graph of percentage of sialic acid as a function of EDTA concentration, and shows the percent sialic acid in the presence of 1.1-1.2 µM $Zn^{+2}$ at Days 33-35 for Blending No. 1 and No. 2 experiments.
Figure 24:
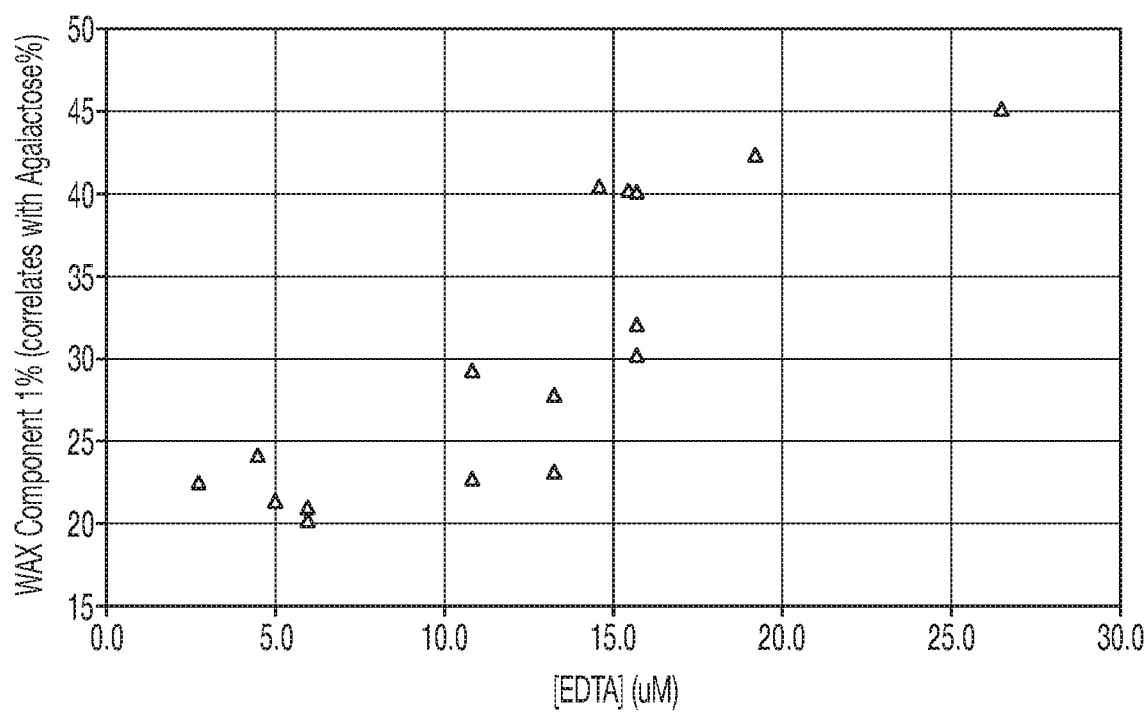
FIG. 24 is a graph of percentage of WAX Component 1 as a function of EDTA concentration, and shows the percentage of infliximab oligosaccharides that lack galactose in the presence of 1.1-1.2 µM $Zn^{+2}$ at Days 33-35 for the Blending No. 1 and No. 2 experiments.
Figure 25:
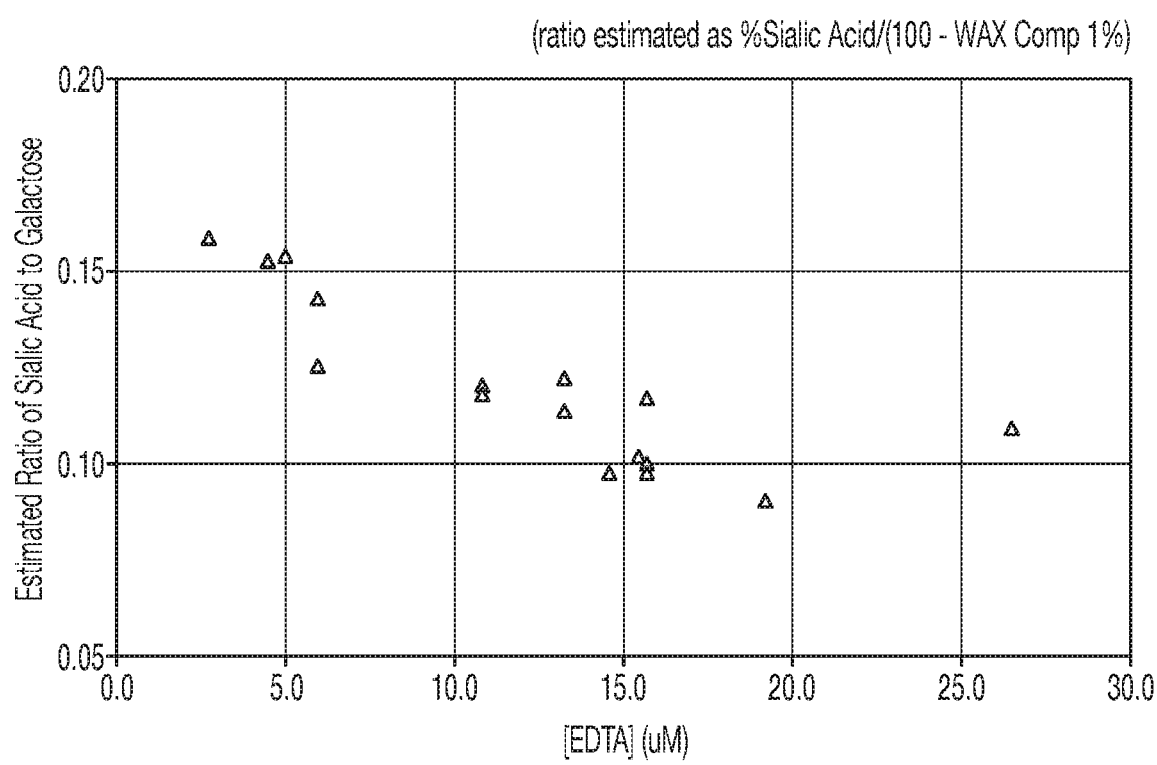
FIG. 25 is a graph of estimated ratio of sialic acid to galactose (estimated as percent sialic acid/(100−percentage of WAX Component 1) as a function of EDTA concentration, and shows the estimated ratio of sialic acid to galactose in the presence of 1.1-1.2 µM $Zn^{+2}$ at Days 33-35 for the Blending No. 1 and No. 2 experiments.

FIG. 21 shows that the ratio of sialic acid to galactose increases with increasing [Zn+2].

Figure 26:
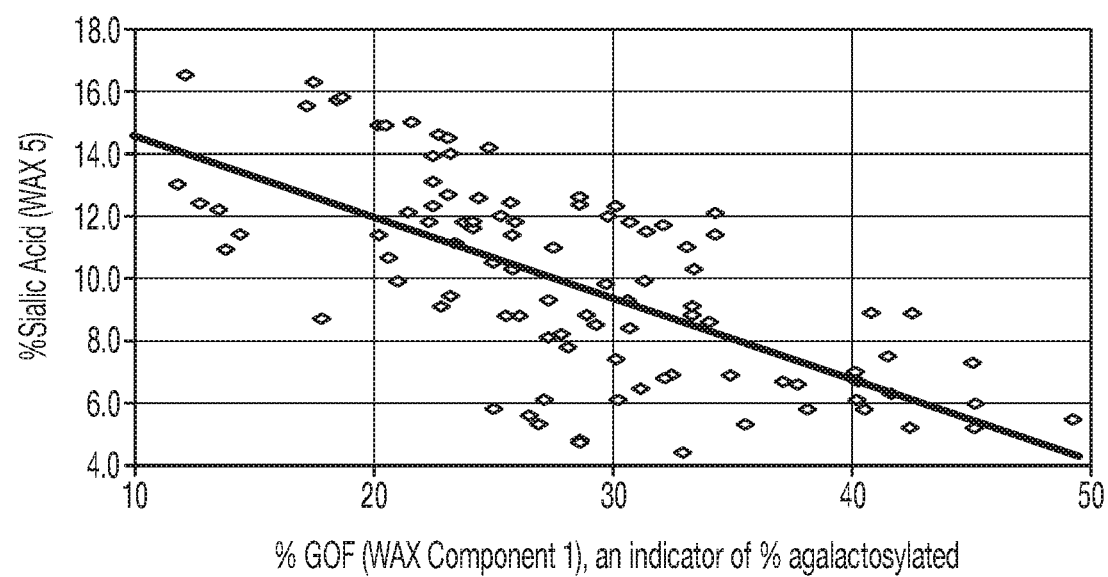
FIG. 26 is a graph of percentage of sialic acid (calculated from WAX Component 5) as a function of percentage of G0F (calculated from WAX Component 1), and shows the inverse relationship between percentage of sialic acid and WAX Component 1, an indicator of infliximab oligosaccharides that lack galactose, for the DOE3 and BSA Blending No. 1 and No. 2 experiments.
Figure 27A:
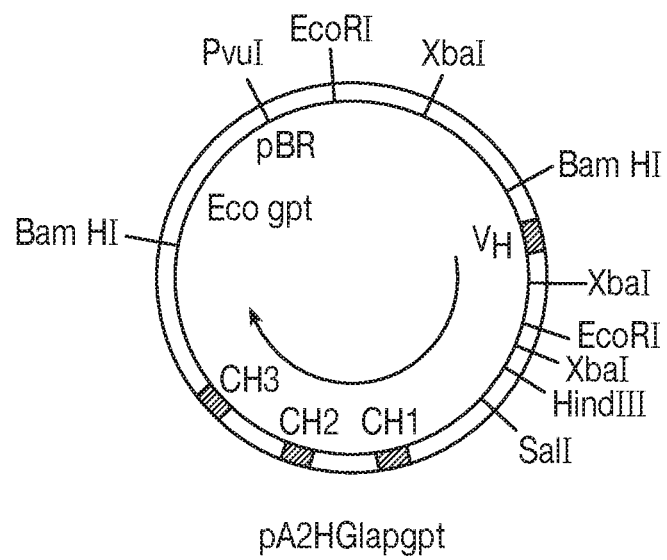
FIGS. 27A and 27B provide schematic diagrams of the plasmids used for expression of the chimeric H (pA2HG1apgpt) and L (pA2HuKapgpt) chains of the chimeric A2 antibody.
Figure 27B:
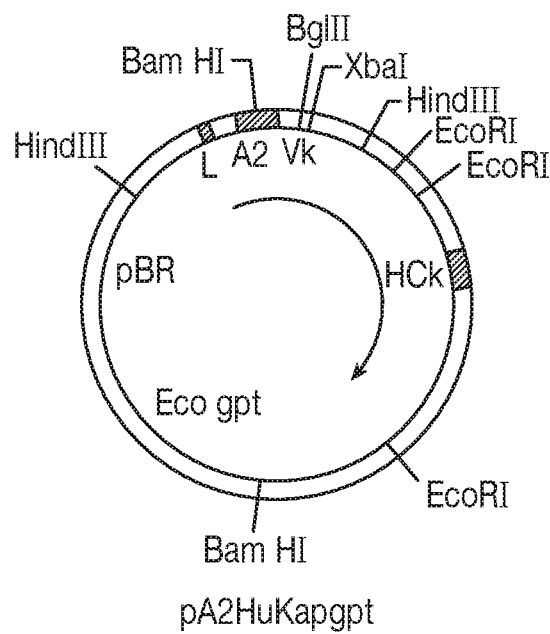

FIG. 26 is a graph of percentage of sialic acid (WAX Component 5) as a function of percentage of G0F (the dominant agalactosyl component of WAX Component 1), and shows the inverse relationship between percentage of sialic acid and the percentage of agalactosyl oligosaccharides, for the DOE3 and BSA Blending No. 1 and No. 2 experiments. FIG. 26 shows that galactose addition and sialic acid addition tend to be coupled in the DOE3 and BSA Blending No. 1 and No. 2 experiments, consistent with a coupling of the reactions catalyzed by galactosyltransferase and sialyltransferase. In other words, factors that enhance these two glycosylation reactions direct more G0F to oligosaccharides containing sialic acid.

The BSA Blending No. 1 and No. 2 experiments both included a sample collected at Days 33-35. FIGS. 22-25 show the Day 33-35 data from the BSA Blending No. 1 and No. 2 experiments. FIGS. 22-25 show that at lower EDTA concentrations, there is higher CTL removal, higher sialic acid content, lower percentage of agalactosyl oligosaccharides, and a higher ratio of sialic acid to galactose.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

---

What is claimed is:

1. A method for producing an antibody sample having a C-terminal lysine content of about 20% to about 70%, and a sialic acid content of about 1% to about 20%, the method comprising:
   culturing a zinc-responsive host cell transfected with deoxyribonucleic acid (DNA) encoding an antibody in a culture medium comprising 0.74 to 2.5 µM zinc; and
   controlling the concentration of zinc in the culture medium to result in a viable cell density of 6 million to 10 million per mL, and producing the antibody sample;
   wherein the antibody is an anti-tumor necrosis factor alpha (anti-TNFα) antibody; and wherein
   a) the light chain of the anti-TNFα antibody comprises the complementarity determining regions (CDRs): CDR1, CDR2 and CDR3 sequences corresponding to amino acid residues 24-34, 50-56 and 89-97 of amino acid sequence SEQ ID NO: 3; and
   b) the heavy chain of the anti-TNFα antibody comprises the CDRs: CDR1, CDR2 and CDR3 corresponding to amino acid residues 31-35, 50-68 and 101-109 of amino acid sequence SEQ ID NO: 5; and
   wherein said anti-TNFα antibody is of immunoglobulin class IgG.

2. The method of claim 1, wherein the C-terminal lysine content of the antibody sample is about 40% to about 70%.

3. The method of claim 2, wherein the C-terminal lysine content of the antibody sample is about 55% to about 65%.

4. The method of claim 3, wherein the C-terminal lysine content of the antibody sample is about 60%.

5. The method of claim 1, wherein the sialic acid content of the antibody sample is about 3% to about 14%.

6. The method of claim 1, wherein the anti-tumor necrosis factor alpha (anti-TNFα) antibody is a human antibody.

7. The method of claim 1, wherein the anti-tumor necrosis factor alpha (anti-TNFα) antibody is a humanized or chimeric antibody.

8. The method of claim 1, wherein the anti-tumor necrosis factor alpha (anti-TNFα) antibody is of immunoglobulin subclass IgG1, IgG2, IgG3, or IgG4.

9. The method of claim 1, wherein the anti-tumor necrosis factor alpha (anti-TNFα) antibody comprises an IgG1 constant region.

10. The method of claim 1, wherein the anti-tumor necrosis factor alpha (anti-TNFα) antibody comprises a non-human variable region comprising an amino acid sequence selected from the group consisting of SEQ ID NO: 3 and SEQ ID NO: 5.

11. The method of claim 10, wherein the light chain of the anti-TNFα antibody comprises a polypeptide encoded by nucleic acid sequence SEQ ID NO: 2 and wherein the heavy chain of the anti-TNFα antibody comprises a polypeptide encoded by nucleic acid sequence SEQ ID NO: 4.

12. The method of claim 1, wherein the anti-tumor necrosis factor alpha (anti-TNFα) antibody is monoclonal antibody cA2.

13. The method of claim 1, wherein the culture medium further comprises total Ethylenediaminetetraacetic acid (EDTA) in a concentration range of about 2.5 µM to about 30 µM, and the method further comprises controlling the concentration of iron-free EDTA in the culture medium.

14. The method of claim 13, wherein the culture medium further comprises iron-free Ethylenediaminetetraacetic acid (EDTA) in a concentration range of about 5 µM to about 16 µM.

15. The method of claim 1, further comprising recovering the antibody.

16. The method of claim 15, wherein the concentration of zinc is controlled until the antibody is recovered.

17. The method of claim 1, wherein the concentration of zinc is controlled during an exponential growth phase of the zinc-responsive host cells.

18. The method of claim 1, wherein controlling the concentration of zinc comprises monitoring the concentration of zinc in the culture medium, and regulating the concentration of zinc in the culture medium, such that the concentration of zinc in the culture medium is 0.74 to 2.5 µM.

19. The method of claim 1, wherein the antibody sample has a galactose content of about 50% to about 90%.

20. The method of claim 19, wherein the antibody sample has a galactose content of about 45% to about 85%.

21. The method of claim 1, wherein the antibody sample has a ratio of sialic acid to galactose of about 0.05 to about 0.20.

22. The method of claim 1, wherein the zinc-responsive host cell is an SP2/0 cell.

23. The method of claim 1, wherein a viable cell density of 6 million to 10 million per mL is attained at 10 or more days in a bioreactor.

24. A method for controlling C-terminal lysine content of an antibody sample having a C-terminal lysine content of about 20% to about 70%, in a process for biosynthesizing an antibody in a culture medium, the method comprising:
   monitoring a level of zinc in the culture medium during biosynthesis of the antibody; and
   regulating the level of zinc in the culture medium during biosynthesis of the antibody such that the culture medium comprises 0.74 to 2.5 µM zinc to result in a viable cell density of 6 million to 10 million per mL, and producing the antibody sample;
   wherein the antibody is an anti-tumor necrosis factor alpha (anti-TNFα) antibody; and wherein
   a) the light chain of the anti-TNFα antibody comprises the complementarity determining regions (CDRs): CDR1, CDR2 and CDR3 sequences corresponding to amino acid residues 24-34, 50-56 and 89-97 of amino acid sequence SEQ ID NO: 3; and
   b) the heavy chain of the anti-TNFα antibody comprises the CDRs: CDR1, CDR2 and CDR3 corresponding to amino acid residues 31-35, 50-68 and 101-109 of amino acid sequence SEQ ID NO: 5; and wherein said anti-TNFα antibody is of immunoglobulin class IgG.

25. The method of claim 24, wherein a viable cell density of 6 million to 10 million per mL is attained at 10 or more days in a bioreactor.

26. A method for controlling sialic acid content of an antibody sample having a sialic acid content of about 1% to about 20% in a process for biosynthesizing an antibody in a culture medium, the method comprising:
   monitoring a level of zinc in the culture medium during biosynthesis of the antibody; and
   regulating the level of zinc in the culture medium during biosynthesis of the antibody such that the culture medium comprises 0.74 to 2.5 µM zinc to result in a viable cell density of 6 million to 10 million per mL, and producing the antibody sample;
   wherein the antibody is an anti-tumor necrosis factor alpha (anti-TNFα) antibody; and wherein
   a) the light chain of the anti-TNFα antibody comprises the complementarity determining regions (CDRs): CDR1, CDR2 and CDR3 sequences corresponding to amino acid residues 24-34, 50-56 and 89-97 of amino acid sequence SEQ ID NO: 3; and
   b) the heavy chain of the anti-TNFα antibody comprises the CDRs: CDR1, CDR2 and CDR3 corresponding to amino acid residues 31-35, 50-68 and 101-109 of amino acid sequence SEQ ID NO: 5; and
   wherein said anti-TNFα antibody is of immunoglobulin class IgG.

27. The method of claim 26, wherein the antibody is monoclonal antibody cA2.

28. The method of claim 27, wherein the antibody is biosynthesized by an SP2/0 cell line.

29. The method of claim 26, wherein a viable cell density of 6 million to 10 million per mL is attained at 10 or more days in a bioreactor.

30. A method for controlling galactose content of an antibody sample having a galactose content of about 50% to about 90% in a process for biosynthesizing an antibody in a culture medium, the method comprising:
   monitoring a level of zinc in the culture medium during biosynthesis of the antibody; and
   regulating the level of zinc in the culture medium during biosynthesis of the antibody such that the culture medium comprises 0.74 to 2.5 µM zinc to result in a viable cell density of 6 million to 10 million per mL, and producing the antibody sample;
   wherein the antibody is an anti-tumor necrosis factor alpha (anti-TNFα) antibody; and wherein
   a) the light chain of the anti-TNFα antibody comprises the complementarity determining regions (CDRs): CDR1, CDR2 and CDR3 sequences corresponding to amino acid residues 24-34, 50-56 and 89-97 of amino acid sequence SEQ ID NO: 3; and
   b) the heavy chain of the anti-TNFα antibody comprises the CDRs: CDR1, CDR2 and CDR3 corresponding to amino acid residues 31-35, 50-68 and 101-109 of amino acid sequence SEQ ID NO: 5; and
   wherein said anti-TNFα antibody is of immunoglobulin class IgG.

31. The method of claim 30, wherein a viable cell density of 6 million to 10 million per mL is attained at 10 or more days in a bioreactor.

32. A method for controlling the ratio of sialic acid to galactose in an antibody sample having a ratio of sialic acid to galactose of about 0.05 to about 0.20 in a process for biosynthesizing the antibody in a culture medium, the method comprising:
   monitoring a level of zinc in the culture medium during biosynthesis of an antibody; and
   regulating the level of zinc in the culture medium during biosynthesis of the antibody such that the culture medium comprises 0.74 to 2.5 µM zinc to result in a viable cell density of 6 million to 10 million per mL, and producing the antibody sample;
   wherein the antibody is an anti-tumor necrosis factor alpha (anti-TNFα) antibody; and wherein
   a) the light chain of the anti-TNFα antibody comprises the complementarity determining regions (CDRs): CDR1, CDR2 and CDR3 sequences corresponding to amino acid residues 24-34, 50-56 and 89-97 of amino acid sequence SEQ ID NO: 3; and
   b) the heavy chain of the anti-TNFα antibody comprises the CDRs: CDR1, CDR2 and CDR3 corresponding to amino acid residues 31-35, 50-68 and 101-109 of amino acid sequence SEQ ID NO: 5; and
   wherein said anti-TNFα antibody is of immunoglobulin class IgG.

33. The method of claim 32, wherein a viable cell density of 6 million to 10 million per mL is attained at 10 or more days in a bioreactor.

* * * * *

UNITED STATES PATENT AND TRADEMARK OFFICE
CERTIFICATE OF CORRECTION

PATENT NO. : 11,149,085 B2
APPLICATION NO. : 14/757691
DATED : October 19, 2021
INVENTOR(S) : Marcel Flikweert et al.

Page 1 of 1

It is certified that error appears in the above-identified patent and that said Letters Patent is hereby corrected as shown below:

On the Title Page

Item (71), Applicants, please delete "Janssen Biologies B.V." and insert -- Janssen Biologics B.V. --

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 7

<210> SEQ ID NO 1
<211> LENGTH: 157
<212> TYPE: PRT
<213> ORGANISM: Homo sapiens

<400> SEQUENCE: 1

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 2
<211> LENGTH: 321
<212> TYPE: DNA
<213> ORGANISM: Unknown
<220> FEATURE:
<221> NAME/KEY: CDS
<222> LOCATION: (1)...(321)
<220> FEATURE:
<223> OTHER INFORMATION: Mouse

<400> SEQUENCE: 2

```
gac atc ttg ctg act cag tct cca gcc atc ctg tct gtg agt cca gga     48
Asp Ile Leu Leu Thr Gln Ser Pro Ala Ile Leu Ser Val Ser Pro Gly
1               5                   10                  15
```

```
gaa aga gtc agt ttc tcc tgc agg gcc agt cag ttc gtt ggc tca agc       96
Glu Arg Val Ser Phe Ser Cys Arg Ala Ser Gln Phe Val Gly Ser Ser
            20                  25                  30 atc cac tgg tat cag caa aga aca aat ggt tct cca agg ctt ctc ata      144
Ile His Trp Tyr Gln Gln Arg Thr Asn Gly Ser Pro Arg Leu Leu Ile
        35                  40                  45 aag tat gct tct gag tct atg tct ggg atc cct tcc agg ttt agt ggc      192
Lys Tyr Ala Ser Glu Ser Met Ser Gly Ile Pro Ser Arg Phe Ser Gly
    50                  55                  60 agt gga tca ggg aca gat ttt act ctt agc atc aac act gtg gag tct      240
Ser Gly Ser Gly Thr Asp Phe Thr Leu Ser Ile Asn Thr Val Glu Ser
65                  70                  75                  80 gaa gat att gca gat tat tac tgt caa caa agt cat agc tgg cca ttc      288
Glu Asp Ile Ala Asp Tyr Tyr Cys Gln Gln Ser His Ser Trp Pro Phe
                85                  90                  95 acg ttc ggc tcg ggg aca aat ttg gaa gta aaa                          321
Thr Phe Gly Ser Gly Thr Asn Leu Glu Val Lys
            100                 105

<210> SEQ ID NO 3
<211> LENGTH: 107
<212> TYPE: PRT
<213> ORGANISM: Unknown
<220> FEATURE:
<223> OTHER INFORMATION: Mouse

<400> SEQUENCE: 3

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys
            100                 105

<210> SEQ ID NO 4
<211> LENGTH: 357
<212> TYPE: DNA
<213> ORGANISM: Unknown
<220> FEATURE:
<221> NAME/KEY: CDS
<222> LOCATION: (1)...(357)
<220> FEATURE:
<223> OTHER INFORMATION: Mouse

<400> SEQUENCE: 4 gaa gtg aag ctt gag gag tct gga gga ggc ttg gtg caa cct gga gga      48
Glu Val Lys Leu Glu Glu Ser Gly Gly Gly Leu Val Gln Pro Gly Gly
1               5                   10                  15 tcc atg aaa ctc tcc tgt gtt gcc tct gga ttc att ttc agt aac cac      96
Ser Met Lys Leu Ser Cys Val Ala Ser Gly Phe Ile Phe Ser Asn His
            20                  25                  30 tgg atg aac tgg gtc cgc cag tct cca gag aag ggg ctt gag tgg gtt     144
Trp Met Asn Trp Val Arg Gln Ser Pro Glu Lys Gly Leu Glu Trp Val
```

```
                     35                  40                  45
gct gaa att aga tca aaa tct att aat tct gca aca cat tat gcg gag      192
Ala Glu Ile Arg Ser Lys Ser Ile Asn Ser Ala Thr His Tyr Ala Glu
 50                  55                  60 tct gtg aaa ggg agg ttc acc atc tca aga gat gat tcc aaa agt gct      240
Ser Val Lys Gly Arg Phe Thr Ile Ser Arg Asp Asp Ser Lys Ser Ala
 65                  70                  75                  80 gtc tac ctg caa atg acc gac tta aga act gaa gac act ggc gtt tat      288
Val Tyr Leu Gln Met Thr Asp Leu Arg Thr Glu Asp Thr Gly Val Tyr
                 85                  90                  95 tac tgt tcc agg aat tac tac ggt agt acc tac gac tac tgg ggc caa      336
Tyr Cys Ser Arg Asn Tyr Tyr Gly Ser Thr Tyr Asp Tyr Trp Gly Gln
                100                 105                 110 ggc acc act ctc aca gtc tcc                                          357
Gly Thr Thr Leu Thr Val Ser
        115

<210> SEQ ID NO 5
<211> LENGTH: 119
<212> TYPE: PRT
<213> ORGANISM: Unknown
<220> FEATURE:
<223> OTHER INFORMATION: Mouse

<400> SEQUENCE: 5

Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Ile Phe Ser Asn His
                20                  25                  30

Trp Met Asn Trp Val Arg Gln Ser Pro Glu Lys Gly Leu Glu Trp Val
            35                  40                  45

Ala Glu Ile Arg Ser Lys Ser Ile Asn Ser Ala Thr His Tyr Ala Glu
 50                  55                  60

Ser Val Lys Gly Arg Phe Thr Ile Ser Arg Asp Asp Ser Lys Ser Ala
 65                  70                  75                  80

Val Tyr Leu Gln Met Thr Asp Leu Arg Thr Glu Asp Thr Gly Val Tyr
                 85                  90                  95

Tyr Cys Ser Arg Asn Tyr Tyr Gly Ser Thr Tyr Asp Tyr Trp Gly Gln
                100                 105                 110

Gly Thr Thr Leu Thr Val Ser
        115

<210> SEQ ID NO 6
<211> LENGTH: 22
<212> TYPE: PRT
<213> ORGANISM: Homo sapiens

<400> SEQUENCE: 6

Tyr Ser Gln Val Leu Phe Lys Gly Gln Gly Cys Pro Ser Thr His Val
 1               5                  10                  15

Leu Leu Thr His Thr Ile
                20

<210> SEQ ID NO 7
<211> LENGTH: 22
<212> TYPE: PRT
<213> ORGANISM: Homo sapiens
```

```
<400> SEQUENCE: 7

Tyr Gln Thr Lys Val Asn Leu Leu Ser Ala Ile Lys Ser Pro Cys Gln
1               5                   10                  15

Arg Glu Thr Pro Glu Gly
                20
```